(12) United States Patent
Keicher

(10) Patent No.: US 7,524,825 B2
(45) Date of Patent: Apr. 28, 2009

(54) TRICYCLIC-NUCLEOSIDE COMPOUNDS FOR TREATING VIRAL INFECTIONS

(75) Inventor: Jesse Daniel Keicher, San Carlos, CA (US)

(73) Assignee: SmithKline Beecham Corporation, Philadelphia, PA (US)

(*) Notice: Subject to any disclaimer, the term of this patent is extended or adjusted under 35 U.S.C. 154(b) by 319 days.

(21) Appl. No.: 11/365,321

(22) Filed: Feb. 28, 2006

(65) Prior Publication Data

US 2006/0252715 A1    Nov. 9, 2006

Related U.S. Application Data

(60) Provisional application No. 60/657,463, filed on Feb. 28, 2005.

(51) Int. Cl.
  A01N 43/04    (2006.01)
  A61K 31/70    (2006.01)
  C07H 19/00    (2006.01)
  C07H 19/056   (2006.01)

(52) U.S. Cl. ............ 514/43; 536/27.1; 536/28.1; 536/28.7

(58) Field of Classification Search .......... None
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 5,597,691 A | 1/1997 | Houghton et al. | |
| 5,738,985 A | 4/1998 | Miles et al. | |
| 5,739,002 A | 4/1998 | De Francesco et al. | |
| 5,759,795 A | 6/1998 | Jubin | |
| 5,861,267 A | 1/1999 | Su | |
| 6,030,785 A | 2/2000 | Katze et al. | |
| 6,228,576 B1 | 5/2001 | DelVecchio | |
| 7,268,119 B2* | 9/2007 | Cook et al. | 514/43 |
| 2005/0090463 A1 | 4/2005 | Roberts et al. | |
| 2006/0079468 A1 | 4/2006 | Roberts et al. | |
| 2006/0194749 A1 | 8/2006 | Keicher et al. | |

FOREIGN PATENT DOCUMENTS

| WO | WO 97/12033 A1 | 4/1997 |
|---|---|---|
| WO | WO 98/43991 A1 | 10/1998 |
| WO | WO 01/90121 A2 | 11/2001 |
| WO | WO 02/18404 A2 | 3/2002 |
| WO | WO 02/057287 A2 | 7/2002 |
| WO | WO 02/057425 A2 | 7/2002 |
| WO | WO 03/061385 A1 | 7/2003 |
| WO | WO 2004/014313 A2 | 2/2004 |
| WO | WO 2004/014852 A2 | 2/2004 |
| WO | WO 2005/003147 A2 | 1/2005 |
| WO | WO 2005/021568 A2 | 3/2005 |
| WO | WO 2005/042556 A1 | 5/2005 |

OTHER PUBLICATIONS

U.S. Appl. No. 11/816,581, filed Feb. 28, 2006, Roberts et al.
U.S. Appl. No. 11/839,380, filed Feb. 28, 2006, Keicher et al.
Bartholomeusz, et al., "Hepatitis C Virus (HCV) RNA polymerase assay using cloned HCV non-structural proteins." Antiviral Therapy, 1996, 1 (supp. 4), 18-24.

(Continued)

Primary Examiner—Traviss C McIntosh, III
(74) Attorney, Agent, or Firm—Junrui Yang

(57) ABSTRACT

Disclosed are compounds represented by formulae I, II, and III, and the compositions and methods thereof for treating viral infections caused by a Flaviviridae family virus.

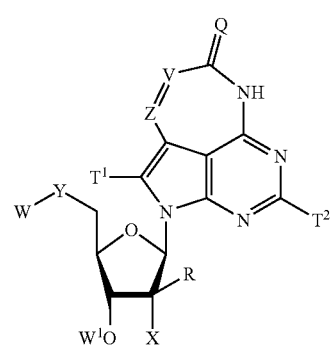

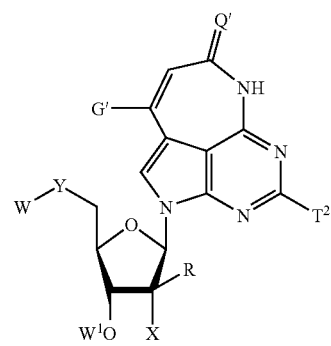

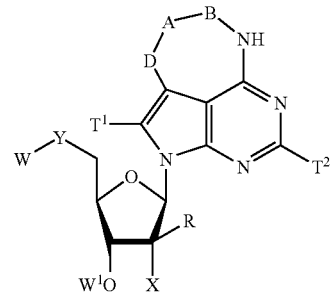

8 Claims, No Drawings

OTHER PUBLICATIONS

Beaulieu, P.L. and Tsantrizos, Y.S., "Inhibitors of the HCV NS5B polymerase: new hope for the treatment of hepatitis C infections." Curr. Opin. Investig. Drugs 2004, 5, 838-850.

Cooperwood, et al., "Nucleoside and Nucleotide prodrugs" in Ed(s) Chu, C. K. Recent Advances in Nucleosides 2002, 92-147.

Cruickshank, et al., "Oligonucleotide labeling: A concise synthesis of a modified thymidine phosphoramidite." Tet. Lett., 1988, 29(41), 5221-5224.

Ferrari et al., "Characterization of soluble hepatitis C virus RNA-dependent RNA polymerase expressed in *Escherichia coli*." J. Virol., 1999, 73, 1649-1654.

Fried, et al., "Peginterferon alfa-2a plus ribavirin for chronic hepatitis C virus infection." N. Engl. J. Med., 2002, 347, 975-982.

Griffith, et al., "HCV Antiviral Agents." Ann. Rep. Med. Chem. 2004, 39, 223-237.

Harper et al., "Potent inhibitors of subgenomic hepatitis C virus RNA replication through optimization of indole-N-acetamide allosteric inhibitors of the viral NS5B polymerase." J. Med. Chem., 2005, 48, 4547-4557.

Hoofnagle, "Hepatitis C: the clinical spectrum of disease." Hepatology 1997, 26, 15S-20S.

Horsmans, et al., "Isatoribine, an agonist of TLR7, reduces plasma virus concentration in chronic hepatitis C infection." Hepatology, 2005, 42, 724-731.

Hutchinson, D.W. (Ed. Leroy B. Townsend) "The Synthesis, Reaction and Properties of Nucleoside Mono-, Di-, and Triphosphates, and Nucleosides with Changes in the Phosphoryl Residue" Chemistry of Nucleosides and Nucleotides, Plenum Press, 1991, 2.

Ishii et al., "Expression of hepatitis C virus NS5B protein: characterization of its RNA polymerase activity and RNA binding." Hepatology, 1999, 29, 1227-1235.

Lohmann et al., "Selective Stimulation of Hepatitis C Virus and Pestivirus NS5B RNA Polymerase Activity by GTP." J. Bio. Chem., 1999, 274, 10807-10815.

Lohmann, et al., "Replication of subgenomic hepatitis C virus RNAs in a hepatoma cell line." Science, 1999, 285, 110-113.

Love et al., "Crystallographic identification of a noncompetitive inhibitor binding site on the hepatitis C virus NS5B RNA polymerase enzyme." J. Virol. 2003, 77, 7575-7581.

Mandal, S.B., et al., "Stereospecific-β-glycosidation and synthesis of 4,7-anhydro-5,6-isopropylidene-4(S), 5(S), 6(R), 7(R)-tetrahydroxyoxocan-2-one" Synth. Commun., 1993, 9, 1239-1244.

Meier, et al., "Pro-Nucleotides-recent advances in the design of efficient tools for the delivery of biologically active nucleoside monophosphates" Synlett 1998, 3, 233-242.

Moriishi and Matsuura, "Mechanisms of hepatitis C virus infection." Antivir. Chem. Chemother. 2003, 14, 285-297.

Ni, Z. J. and Wagman, A. S., "Progress and development of small molecule HCV antivirals." Curr. Opin. Drug Discov. Devel. 2004, 7, 446-459.

Ning, et al., "Syntheses and reactions of 5-O-acetyl-1,2-anhydro-3-O-benzyl-alpha-D-ribofuranose and beta-D-lyxofuranose, 5-O-acetyl-1,2-anhydro-3,6-di-O-benzyl- and 1,2-anhydro-5,6-di-O-benzoyl-3-O-benzyl-beta-D-mannofuranose, and 6-O-acetyl-1,2-anhydro-3,4-di-O-benzyl-alpha-D-glucopyranose and-beta-D-talopyranose." Carbohydr. Res., 2001, 330, p. 165-75.

Olsen et al., "A 7-deaza-adenosine analog is a potent and selective inhibitor of hepatitis C virus replication with exceilent pharmacokinetic properties" Antimicrob. Agents Chemother. 2004, 48, 3944-3953.

Sarisky R.T., "Non-nucleoside inhibitors of the HCV polymerase." J Antimicrob Chemother. 2004, 54, 14-16.

Saunders and Raybuck, "Inosine Monophosphate Dehydrogenase: Consideration of Structure, Kinetics and Therapeutic Potential." Ann. Rep. Med. Chem., 2000, 35, 201-210.

Seela, Frank et al., "7-substituted-7-deaza-2'-deoxyadenosines and 8-aza-7-deaza-2'-deoxyadenosines: fluorescence of DNA-base analogs induced by the 7-alkynyl side chain" Helvetica Chimica Acta, 2000, 83(5), 910-927.

Szabo, et al., "Viral hepatitis: new data on hepatitis C infection." Pathol. Oncol. Res. 2003, 9, 215-221.

Thomson, BJ and Finch, RG, "Hepatitis C virus infection" Clin Microbial Infect. 2005, 11, 86-94.

Wagner, et al., "Pronucleotides: Toward the in vivo delivery of antiviral and anticancer nucleotides." Medicinal Research Reviews 2000, 20(6), 417-451.

Watashi, et al., "Cyclophilin B is a functional regulator of hepatitis C virus RNA polymerase." Molecular Cell, 2005, 19, 111-122.

Witty, D.R., et al., "Ring contraction of 2-o-trifluoromethanesulphonates of α-hydroxy-γ-lactones to oxetane carboxylic esters." Tet. Lett, 1990, 31, 4787-4790.

Yamashita et al., "RNA-dependent RNA Polymerase Activity of the Soluble Recombinant Hepatitis C Virus NS5B Protein Truncated at the C-terminal Region." J. Bio. Chem., 1998, 273, 15479-15186.

Zemlicka, et al., "Lipophilic phosphoramidates as antiviral pronucleotides." Biochimica et Biophysica Acta 2002, 1587(2-3), 276-286.

\* cited by examiner

TRICYCLIC-NUCLEOSIDE COMPOUNDS FOR TREATING VIRAL INFECTIONS

CROSS-REFERENCE TO RELATED APPLICATION

This application claims the benefit under 35 U.S.C. 119(e) to provisional application U.S. Ser. No. 60/657,463 filed on Feb. 28, 2005, which is incorporated herein by reference in its entirety.

BACKGROUND OF THE INVENTION

1. Field of the Invention

The invention relates to the field of pharmaceutical chemistry, in particular to compounds, compositions and methods for treating viral infections in mammals mediated, at least in part, by a virus in the Flaviviridae family of viruses.

REFERENCES

The following publications, patents, and patent applications are cited in this application as superscript numbers:

1. Szabo, et al., *Pathol. Oncol. Res.* 2003, 9:215-221.
2. Hoofnagle J H, *Hepatology* 1997, 26:15S-20S.
3. Thomson B J and Finch R G, *Clin Microbial Infect.* 2005, 11:86-94.
4. Moriishi K and Matsuura Y, *Antivir. Chem. Chemother.* 2003, 14:285-297.
5. Fried, et al. *N. Engl. J. Med* 2002, 347:975-982.
6. Ni, Z. J. and Wagman, A. S. *Curr. Opin. Drug Discov. Devel.* 2004, 7, 446-459.
7. Beaulieu, P. L. and Tsantrizos, Y. S. *Curr. Opin. Investig. Drugs* 2004, 5, 838-850.
8. Griffith, et al., *Ann. Rep. Med. Chem.* 39, 223-237, 2004.
9. Sommadossi, et al., International Patent Application Publication No. WO 01/90121, published May 23, 2001
10. Olson et al., *Antimicrob. Agents Chemother.* 2004, 48:3944-53
11. Sarisky R. T. *J Antimicrob Chemother.* 2004, 54:14-6
12. Love et al., *J Virol.* 2003, 77:7575-81
13. Harper et al., *J Med Chem.* 2005, 48:4547-57
14. Hiromasa et al., U.S. Pat. No. 6,770,666 issued Aug. 3, 2004
15. Watashi, et al., *Molecular Cell,* 19, 111-122, 2005
16. Horsmans, et al., *Hepatology,* 42, 724-731, 2005
17. Carroll, S. S., et al., International Patent Application Publication No. WO 02/057287, published 25 Jul., 2002;
18. Carroll, S. S., et al., International Patent Application Publication No. WO 02/057425, published 25 Jul., 2002.

All of the above publications, patents, and patent applications are herein incorporated by reference in their entirety to the same extent as if each individual publication or application was specifically and individually indicated to be incorporated by reference in its entirety.

2. State of the Art

Chronic infection with HCV is a major health problem associated with liver cirrhosis, hepatocellular carcinoma and liver failure. An estimated 170 million chronic carriers worldwide are at risk of developing liver disease.[1,2] In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured. While the pathology of HCV infection affects mainly the liver, the virus is found in other cell types in the body including peripheral blood lymphocytes.[3,4]

At present, the standard treatment for chronic HCV is interferon alpha (IFN-alpha) in combination with ribavirin and this requires at least six (6) months of treatment. IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load [5] and there is a clear need for more effective antiviral therapy of HCV infection.

A number of approaches are being pursuit to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5b RNA-dependent RNA polymerase are considered the most promising viral targets for new drugs.[6-8]

The NS5b RNA-dependent RNA polymerase in particular has been shown to be amenable to small-molecule inhibition. Besides several nucleoside inhibitors, [9,10] at least three allosteric sites have been described, [7] along with multiple inhibitor scaffolds. [11-14]

Besides targeting viral genes and their transcription and translation products, antiviral activity can also be achieved by targeting host cell proteins that are necessary for viral replication. For example, Watashi et al. [15] show how antiviral activity can be achieved by inhibiting host cell cyclophilins. Alternatively, a potent TLR7 agonist has been shown to reduce HCV plasma levels in humans. [16]

However, none of the compounds described above have progressed beyond clinical trials. [6,8]

In view of the worldwide epidemic level of HCV and other members of the Flaviviridae family of viruses, and further in view of the limited treatment options, there is a strong need for new effective drugs for treating infections cause by these viruses.

SUMMARY OF THE INVENTION

This invention is directed to novel compounds that are useful in the viral infections in mammals, mediated at least in part by a virus in the Flaviviridae family of viruses. In one of its composition aspects, the present invention encompasses compounds of Formula I:

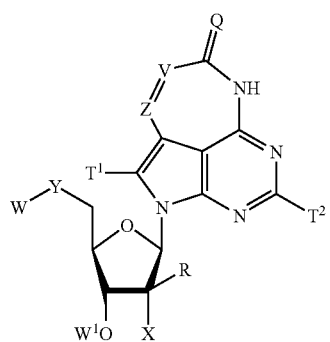

I wherein:
R is selected from the group consisting of hydrogen and $C^1$-$C_3$ alkyl;
X is selected from the group consisting of hydrogen, halo, and $OW^2$;
Y is selected from the group consisting of a bond, O, and $CH_2$;
Q is absent or is selected from the group consisting of O, S, and NH, provided that when Q is absent, V and NH are both attached to a $CH_2$ group;
V is selected from the group consisting of N and C-G;
Z is selected from the group consisting of N and C-G';
G and G' are independently selected from the group consisting of hydrogen, amino, aminocarbonyl, methylamino, dimethylamino, acylamino, alkoxyamino, —$SO_3H$, —$SO_2NH_2$, aminocarbonylamino, oxycarbonylamino, HR'NCHR"C(O)NH—, azido, cyano, halo, hydroxyamino, and hydrazino where R' is hydrogen and R" is a side-chain of an amino acid or where R' and R" together with the nitrogen and carbon bound to each group respectively form a pyrrolidinyl group;
provided that V and Z are not identical;
provided that when V is C—H, Z is N;
$T^1$ and $T^2$ are independently selected from the group consisting of hydrogen, hydroxyl, $C^1$-$C_4$-alkoxy, $C^1$-$C_4$-thioalkoxy, amino, substituted amino, and halo; and
each of W, $W^1$, and $W^2$ is independently selected from the group consisting of hydrogen, $C^1$-$C_4$ alkyl, and a prodrug group; or a pharmaceutically acceptable salt, a tautomer, or a pharmaceutically acceptable salt of a tautomer thereof.

In one aspect, the present invention encompasses compounds of formula I represented by formula Ia, Ib, and Ic:

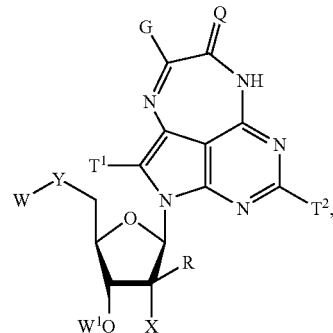

Ia

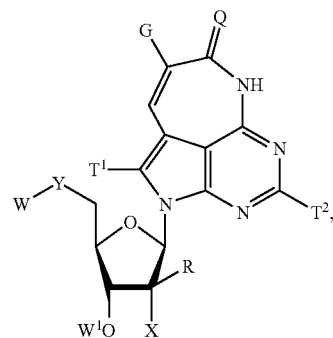

Ib

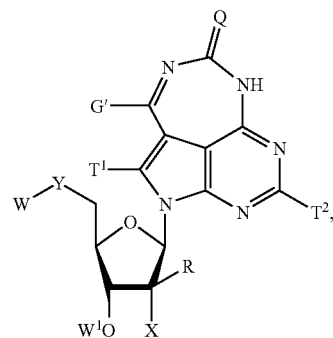

Ic wherein Q, G, G', $T^1$, $T^2$, W, $W^1$, X, Y, and R are previously defined for formula I, and G for formula Ib is selected from the group consisting of amino, aminocarbonyl, methylamino, dimethylamino, acylamino, alkoxyamino, —$SO_3H$, —$SO_2NH_2$, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group.

In another of its composition aspects, the present invention encompasses compounds of formula II

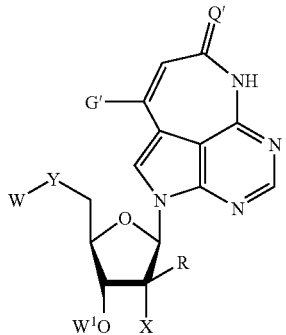

II

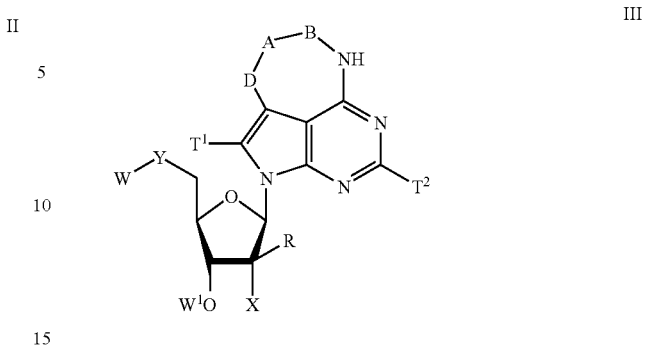

III wherein:

R is $C^1$-$C_3$ alkyl;

X is selected from the group consisting of hydrogen, halo, and $OW^2$;

Q' is selected from the group consisting of NH, O, and S;

G' is selected from the group consisting of amino, aminocarbonyl, methylamino, dimethylamino, acylamino, —$SO_3H$, —$SO_2NH_2$, alkoxyamino, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group;

Y is selected from the group consisting of a bond, O, and $CH_2$; and each of W, $W^1$, and $W^2$ is independently selected from the group consisting of hydrogen, $C^1$-$C_4$ alkyl, and a prodrug group; or a pharmaceutically acceptable salt, a tautomer, or a pharmaceutically acceptable salt of a tautomer thereof.

In one aspect, the present invention encompasses compounds of formula II represented by formula IIa:

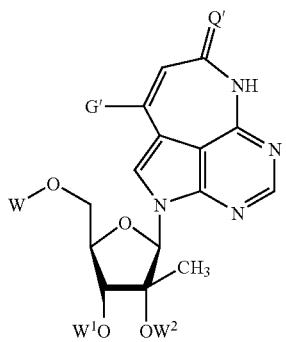

IIa wherein:

Q', G', W, $W^1$, and $W^2$ are previously described for formula II.

In another of its composition aspects, the present invention encompasses compounds of formula III:

wherein:

A and B are independently selected from the group consisting of C=Q, NH, and methylene optionally substituted with 1 to 2 halo groups, provided that A and B are not both NH;

D is NH, or -D-A-B- together form a —N=CH—NH—, —(C=Q)-$CH_2$—(C=Q)-, —(C=Q)-NH—(C=Q)-, —(CX')=(CX')—(C=Q)-, or —CH=CH—NH— group where X' is halo;

each Q is independently selected from the group consisting of O, S, and NH;

R is selected from the group consisting of hydrogen and $C^1$-$C_3$ alkyl;

X is selected from the group consisting of hydrogen, halo, and $OW^2$;

$T^1$ and $T^2$ are independently selected from the group consisting of hydrogen, hydroxyl, $C^1$-$C_4$-alkoxy, $C^1$-$C_4$-thioalkoxy, amino, substituted amino, and halo;

Y is selected from the group consisting of a bond, O, and $CH_2$; and each of W, $W^1$, and $W^2$ is independently selected from the group consisting of hydrogen, $C^1$-$C_4$ alkyl, and a prodrug group; or a pharmaceutically acceptable salt, a tautomer, or a pharmaceutically acceptable salt of a tautomer thereof.

The present invention also encompasses pharmaceutical compositions comprising compounds of formula I, Ia, Ib, Ic, II, IIa, and III and methods of using these compounds for treating viral diseases mediated at least in part by a virus in the Flaviviridae family of viruses.

DETAILED DESCRIPTION OF THE INVENTION

Throughout this application, the text refers to various embodiments of the present compounds, compositions, and methods. The various embodiments described are meant to provide a variety illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Definitions

As used herein, the following definitions shall apply unless otherwise indicated.

"Alkyl" refers to monovalent saturated hydrocarbyl groups having from 1 to 6 carbon atoms and preferably 1 to 2 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Alkoxyamino" refers to the group "alkyl-O—NH—". Examples of alkoxyamino include methoxyamino and ethoxyamino.

"Substituted alkoxy" refers to the group "substituted alkyl-O—".

"Acyl" refers to the groups alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Aminoacyl" refers to the group —C(O)NR$_4$R$_4$ where each R$_4$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$_4$ is joined to form together with the nitrogen atom a heterocyclic or substituted heterocyclic ring.

"Aminocarbonyl" refers to the group —C(O)NH$_2$ and is a specific example of an aminoacyl group.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Oxyacyl" refers to the groups alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

"Alkenyl" refers to monovalent hydrocarbyl groups having from 2 to 6 carbon atoms and preferably 2 to 4 carbon atoms and having at least 1 and preferably from 1-2 sites of vinyl (>C=C<) unsaturation. Such groups are exemplified by vinyl(ethen-1-yl), allyl, but-3-en-1-yl, and the like. Included within this term are the cis and trans isomers or mixtures of these isomers.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom. Preferred substituted alkenyl groups are selected from, but not limit to, 2,2-difluoroethen-1-yl, 2-methoxyethen-1-yl, and the like.

It is understood that the term "substituted alkenyl" includes both E (cis) and Z (trans) isomers as appropriate. The isomers can be pure isomeric compounds or mixtures of E and Z components.

"Alkynyl" refers to branched or unbranched monovalent, hydrocarbyl groups having at least 1 site of acetylenic (—C≡C—) unsaturation and having from 2 to 6 carbon atoms and more preferably 2 to 4 carbon atoms. Preferred alkynyl groups are selected from but not limit to ethyn-1-yl, propyn-1-yl, propyn-2-yl, 1-methylprop-2-yn-1-yl, butyn-1-yl, butyn-2-yl, butyn-3-yl, and the like.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic with the proviso that any hydroxyl substitution is not attached to an acetylenic carbon atom. Preferred substituted alkynyl groups are selected from but not limit to 2-fluoroethyn-1-yl, 3,3,3-trifluoropropyn-1-yl, 3-aminopropyn-1-yl, 3-hydroxypropyn-1-yl, and the like.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. Substituted amino groups include methylamino (—NHCH$_3$) and dimethylamino (—N(CH$_3$)$_2$).

"Acylamino" refers to the groups —NR$^5$C(O)alkyl, —NR$^5$C(O)substituted alkyl, —NR$^5$C(O)cycloalkyl, —NR$^5$C(O)substituted cycloalkyl, —NR$^5$C(O)alkenyl, —NR$^5$C(O)substituted alkenyl, —NR$^5$C(O)alkynyl, —NR$^5$C(O)substituted alkynyl, —NR$^5$C(O)aryl, —NR$^5$C(O)substituted aryl, —NR$^5$C(O)heteroaryl, —NR$^5$C(O)substituted heteroaryl, —NR$^5$C(O)heterocyclic, and —NR$^5$C(O)substituted heterocyclic where R$^5$ is hydrogen or alkyl.

"Aminocarbonylamino" refers to the group —NR$^a$(C=O) NR$^b$R$_c$ wherein R$^a$, R$^b$, and R$^c$ are independently selected from the group consisting of hydrogen and C$^1$-C$_6$ alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl", including "substituted phenyl" refers to aryl groups or phenyl groups which are substituted with from 1 to 3 substituents, and preferably 1 to 2 substituents, selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl ester, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Azido" refers to the group —$N_3$.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

"Cyano" refers to the group —CN.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Formyl" refers to the —C(O)H group.

"Halo" or "halogen" refers to fluoro, chloro, bromo and iodo and preferably is fluoro or chloro.

"Heteroaryl" refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms, such as N(O), S(O) and $S(O)_2$. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridyl, pyrrolyl, thienyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, S(O), and $S(O)_2$ within the ring wherein, in fused ring systems, one or more the rings can be cycloalkyl, aryl or heteroaryl provided that the point of attachment is through the heterocyclic ring.

"Substituted heterocyclic" or "substituted heterocycloalkyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Hydroxyamino" refers to the group —NHOH.

"Hydrazino" refers to the group —$NHNH_2$.

"Oxycarbonylamino" refers to —$NR^a(C=O)$—O—$R^d$ wherein $R^a$ and $R^d$ are independently selected from the group consisting of hydrogen and $C^1$-$C_6$ alkyl.

"Pyrrolidinyl" refers to a saturated five membered ring having one ring nitrogen atom. The heterocyclic ring of the amino acid proline is an example of a pyrrolidinyl group.

"Prodrug", "prodrugs", and "pharmaceutically acceptable prodrugs" refer to a derivative of an active compound (drug) that undergoes a transformation under the conditions of use, such as within the body, to release an active drug or an active metabolite thereof. Prodrugs are frequently, but not necessarily, pharmacologically inactive until converted into the active drug or an active metabolite thereof. Prodrugs are typically obtained by masking one or more functional groups in the drug believed to be in part required for activity with a prodrug group (defined below) to form a prodrug moiety which undergoes a transformation, such as cleavage, under the specified conditions of use to release the functional group, and hence the active drug. The cleavage of the prodrug moiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature or pH. The agent may be endogenous to the conditions of use, such as an enzyme present in the cells to which the prodrug is administered or the acidic conditions of the stomach, or it may be supplied exogenously.

A wide variety of prodrug groups, as well as the resultant prodrug moieties, suitable for masking functional groups in active compounds to yield prodrugs are well-known in the art. For example, a hydroxyl functional group may be masked as a sulfonate, ester or carbonate prodrug moiety, which may be hydrolyzed in vitro to provide the hydroxyl group. An amino functional group may be masked as an amide, imine, phosphinyl, phosphonyl, phosphoryl or sulfenyl promoiety, which may be hydrolyzed in vivo to provide the amino group. A carboxyl group may be masked as an ester (including silyl esters and thioesters), amide or hydrazide prodrug moiety, which may be hydrolyzed in vivo to provide the carboxyl group. Other specific examples of suitable prodrug groups and their respective prodrug moieties will be apparent to those of skill in the art.

"Prodrug group" refers to a type of protecting group that, when used to mask a functional group within an active drug to form a prodrug moiety, converts the drug into a prodrug. Prodrug groups are typically attached to the functional group of the drug via bonds that are cleavable under specified conditions of use. Thus, a prodrug group is that portion of a prodrug moiety that cleaves to release the functional group under the specified conditions of use. As a specific example, an amide prodrug moiety of the formula —NH—C(O)CH$_3$ comprises the prodrug group —C(O)CH$_3$.

"Phosphate" refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood, of course, that the initial oxygen of the mono-, di- and triphosphate (phospho, diphospho and triphospho) includes the oxygen atom at, for example, the 5-position of the ribose sugar.

"Phosphate esters" refers to the mono-, di- and tri-phosphate groups described above wherein one or more of the hydroxyl groups is replaced by an alkoxy group.

"Phosphonate" refers to the groups —OP(O)(R$^6$)(OH) or —OP(O)(R$^6$)(OR$^{6'}$) or salts thereof including partial salts thereof, wherein R$^6$ is independently selected from hydrogen, alkyl, and substituted alkyl, and R$^{6'}$ is independently selected from hydrogen, alkyl, substituted alkyl, carboxylic acid, and carboxyl ester. It is understood, of course, that the initial oxygen of the phosphonate includes the oxygen atom at, for example, the 5-position of the ribose sugar.

"Phosphorodiamidate" refers to the group:

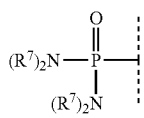

where each R$^7$ may be the same or different and each is hydrogen, alkyl, substituted alkyl, cycloalkyl, or substituted cycloalkyl. A particularly preferred phosphorodiamidate is the following group:

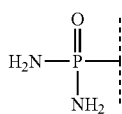

"Phosphoramidate monoester" refers to the group below, where R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a side-chain of an amino acid; and R$^8$ is hydrogen or alkyl. In a preferred embodiment R$^3$ is derived from an L-amino acid.

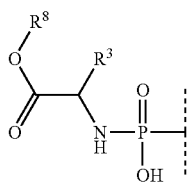

"Phosphoramidate diester" refers to the group below, where R$^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic, and R$^3$ and R$^8$ are as defined above. In a preferred embodiment R$^3$ is derived from an L-amino acid.

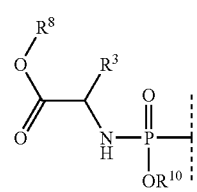

"Cyclic phosphoramidate" refers to the group below, where n is 1 to 3, more preferably n is 1 to 2.

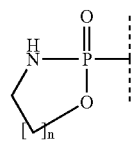

"Cyclic phosphorodiamidate" refers to the group below, where n is 1 to 3, more preferably n is 1 to 2.

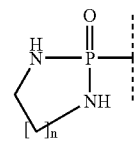

"Phosphonamidate" refers to the group below, where R$^{11}$ is hydrogen, alkyl, substituted alkyl, cycloalkyl, or substituted cycloalkyl.

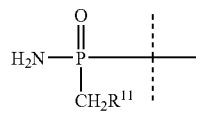

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thiocycloalkyl" refers to the groups —S-cycloalkyl and "substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

The term "amino acid side-chain" refers to the R$^3$ substituent of α-amino acids of the formula R$^{13}$NHCH(R$^3$)COOH where R$^3$ is selected from the group consisting of hydrogen, alkyl, substituted alkyl and aryl and R$^{13}$ is hydrogen or together with R³ and the nitrogen and carbon atoms bound thereto respectively form a heterocyclic ring. Preferably, the α-amino acid side-chain is the side-chain one of the twenty naturally occurring L amino acids. Such side chains include hydrogen (glycine), methyl (alanine), isopropyl (valine), sec-butyl (leucine), 1-methylprop-1-yl (isoleucine), benzyl (phenylalanine), 4-hydroxybenzyl (tyrosine), indol-3-ylmethylene (tryptophan), 2-(methylthio)eth-1-yl (methionine), hydroxymethyl (serine), 1-hydroxyeth-1-yl (threonine), thiomethyl (cysteine), $H_2NC(O)CH_2$— (asparagine), $H_2NC(O)CH_2CH_2$— (glutamine), $HOOCCH_2$— (aspartic acid), $HOOCCH_2CH_2$— (glutamic acid), 4-amino-n-but-1-yl (lysine), 3-guanadinoprop-1-yl (arginine), imidazol-4-ylmethyl (histidine) and where $R^{13}$ and $R^3$ form a pyrrolidinyl ring (proline).

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkyl-ammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable partial salts" refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The equilibrium between tautomers is rapid under normal conditions and often strongly favors one of the isomers (acetone, for example, is 99.999% keto tautomer). Even in such one-sided equilibria, evidence for the presence of the minor tautomer comes from the chemical behavior of the compound. Tautomeric equilibria are catalyzed by traces of acids or bases that are generally present in most chemical samples. Some examples of tautomers of the present invention are shown below:

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

Accordingly, the present invention encompasses a compound represented by formula I

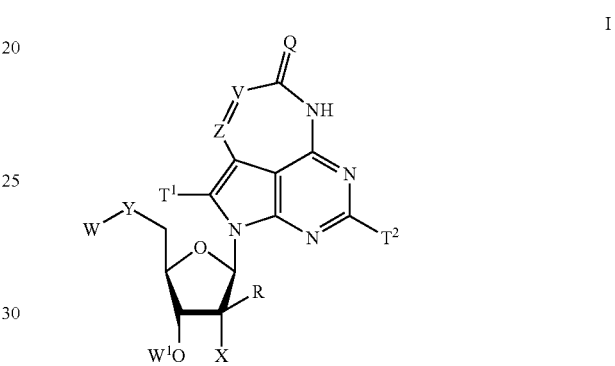

I wherein:
R is selected from the group consisting of hydrogen and $C^1$-$C_3$ alkyl;

X is selected from the group consisting of hydrogen, halo, and $OW^2$;

Y is selected from the group consisting of a bond, O, and $CH_2$;

Q is absent or is selected from the group consisting of O, S, and NH, provided that when Q is absent, V and NH are both attached to a $CH_2$ group;

V is selected from the group consisting of N and C-G;

Z is selected from the group consisting of N and C-G';

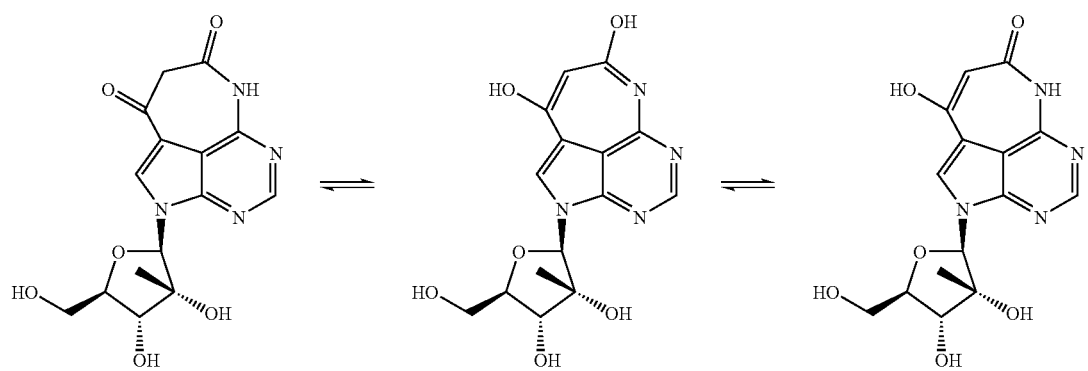

G and G' are independently selected from the group consisting of hydrogen, amino, aminocarbonyl, methylamino, dimethylamino, acylamino, alkoxyamino, —SO$_3$H, —SO$_2$NH$_2$, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group;

provided that V and Z are not identical;

provided that when V is C—H, Z is N;

T$^1$ and T$^2$ are independently selected from the group consisting of hydrogen, hydroxyl, C$^1$-C$_4$-alkoxy, C$^1$-C$_4$-thioalkoxy, amino, substituted amino, and halo; and each of W, W$^1$, and W$^2$ is independently selected from the group consisting of hydrogen, C$^1$-C$_4$ alkyl, and a prodrug group; or a pharmaceutically acceptable salt, a tautomer, or a pharmaceutically acceptable salt of a tautomer thereof.

In some embodiments of the compounds of formula I, R is methyl. In some aspects Y is O. In other aspects X is OW$^2$ and W$^1$, W$^2$, and W$^3$ are hydrogen. In still other aspects T$^1$ and T$^2$ are hydrogen. In some aspects Q is O.

In some embodiments of the compounds of formula I, X is fluoro.

In one embodiment, a compound of formula I is represented by formula Ia:

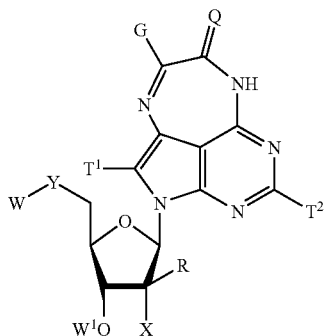

Ia wherein:

Q, G, T$^1$, T$^2$, Y, W, W$^1$, X, and R are as described for formula I.

In some embodiments of the compounds of formula Ia or in combination with any of the formula Ia embodiments, G is azido, amino, acylamino, cyano, hydrogen, and halo. In some aspects G is hydrogen. In other aspects, G is halo. In some aspects, G is fluorine.

In some embodiments of the compounds of formula Ia or in combination with any of the formula Ia embodiments, Q is O.

In some embodiments of the compounds of formula Ia or in combination with any of the formula Ia embodiments, Q is absent.

In some embodiments of the compounds of formula Ia or in combination with any of the formula Ia embodiments, R is methyl. In some aspects Y is O. In other aspects X is OW$^2$ and W$^1$, W$^2$, and W$^3$ are hydrogen. In still other aspects T$^1$ and T$^2$ are hydrogen.

In some embodiments of the compounds of formula Ia or in combination with any of the formula Ia embodiments, X is fluoro.

In some embodiments of the compounds of formula Ia or in combination with any of the formula Ia embodiments, one of W$^1$ or W$^2$ is a prodrug group.

In another embodiment, a compound of formula I is represented by formula Ib

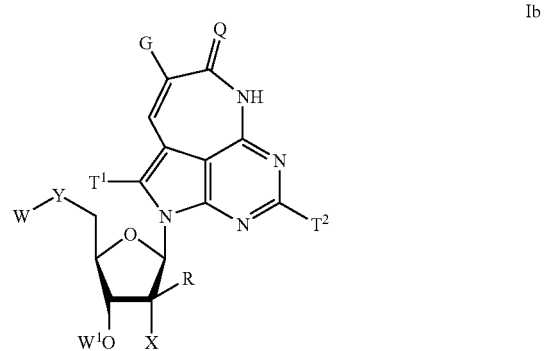

Ib wherein:

G is selected from the group consisting of amino, aminocarbonyl, methylamino, dimethylamino, acylamino, alkoxyamino, —SO$_3$H, —SO$_2$NH$_2$, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group; and Q, T$^1$, T$^2$, Y, W, W$^1$, X, and R are as described for formula I.

In some embodiments of the compounds of formula Ib or in combination with any of the formula Ib embodiments, G is azido, amino, acylamino, cyano, and halo. In some aspects G is halo. In some aspects, G is fluorine. In other aspects G is amino.

In some embodiments of the compounds of formula Ib or in combination with any of the formula Ib embodiments, Q is O.

In some embodiments of the compounds of formula Ib or in combination with any of the formula Ib embodiments, Q is absent.

In some embodiments of the compounds of formula Ib or in combination with any of the formula Ib embodiments, R is methyl. In some aspects Y is O. In other aspects X is OW$^2$ and W$^1$, W$^2$, and W$^3$ are hydrogen. In still other aspects T$^1$ and T$^2$ are hydrogen.

In some embodiments of the compounds of formula Ib or in combination with any of the formula Ib embodiments, X is fluoro.

In some embodiments of the compounds of formula Ib or in combination with any of the formula Ib embodiments, one of W$^1$ or W$^2$ is a prodrug group.

In another embodiment, a compound of formula I is represented by formula Ic:

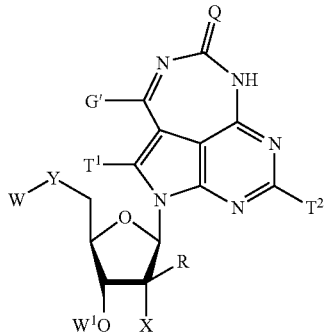

Ic wherein:

Q, G', $T^1$, $T^2$, Y, W, $W^1$, X, and R are as described for formula I.

In some embodiments of the compounds of formula Ic or in combination with any of the formula Ic embodiments, Q is O.

In some embodiments of the compounds of formula Ic or in combination with any of the formula Ic embodiments, Q is absent.

In some embodiments of the compounds of formula Ic or in combination with any of the formula Ic embodiments, G' is selected from the group consisting of azido, amino, aminocarbonyl, acylamino, alkoxyamino, cyano, halo, hydroxyamino, hydrogen, and hydrazino.

In some embodiments of the compounds of formula Ic or in combination with any of the formula Ic embodiments, G' is selected from the group consisting of azido, amino, acylamino, cyano, hydrogen, and halo.

In some embodiments of the compounds of formula Ic or in combination with any of the formula Ic embodiments, G' is selected from the group consisting of fluoro, chloro, iodo, methoxyamino, hydroxyamino, —NH(CO)H, —NH(CO)CH$_3$, hydrazino, amino, aminocarbonyl, and cyano. In some aspects G' is selected from the group consisting of fluoro, chloro, iodo, —NH(CO)H, —NH(CO)CH$_3$, amino, and cyano.

In some embodiments of the compounds of formula Ic or in combination with any of the formula Ic embodiments, R is methyl. In some aspects Y is O. In other aspects X is $OW^2$ and $W^1$, $W^2$, and $W^3$ are hydrogen. In still other aspects $T^1$ and $T^2$ are hydrogen.

In some embodiments of the compounds of formula Ic or in combination with any of the formula Ic embodiments, X is fluoro.

In some embodiments of the compounds of formula Ic or in combination with any of the formula Ic embodiments, one of $W^1$ or $W^2$ is a prodrug group.

The present invention also encompasses a compound of formula II:

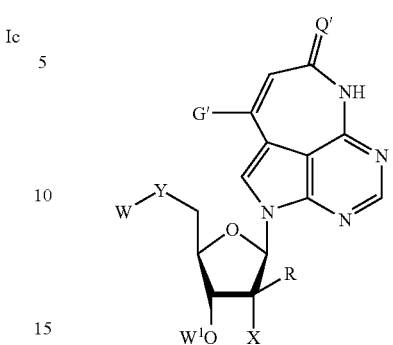

II wherein:

R is $C^1$-$C_3$ alkyl;

X is selected from the group consisting of hydrogen, halo, and $OW^2$;

Q' is selected from the group consisting of NH, O, and S;

G' is selected from the group consisting of amino, aminocarbonyl, methylamino, dimethylamino, acylamino, —SO$_3$H, —SO$_2$NH$_2$, alkoxyamino, aminocarbonylamino, oxycarbonylamino, HR'NCHR"C(O)NH—, azido, cyano, halo, hydroxyamino, and hydrazino, where R' is hydrogen and R" is a side-chain of an amino acid or where R' and R" together with the nitrogen and carbon bound to each group respectively form a pyrrolidinyl group;

Y is selected from the group consisting of a bond, O, and CH$_2$; and each of W, $W^1$, and $W^2$ is independently selected from the group consisting of hydrogen, $C^1$-$C_4$ alkyl, and a prodrug group; or a pharmaceutically acceptable salt, a tautomer, or a pharmaceutically acceptable salt of a tautomer thereof.

In some embodiments of the compounds of formula II or in combination with any of the formula II embodiments, Q' is O.

In some embodiments of the compounds of formula II or in combination with any of the formula II embodiments, G' is selected from the group consisting of azido, amino, aminocarbonyl, acylamino, alkoxyamino, cyano, halo, hydroxyamino, and hydrazino.

In some embodiments of the compounds of formula II or in combination with any of the formula II embodiments, G' is selected from the group consisting of azido, amino, acylamino, cyano, and halo.

In some embodiments of the compounds of formula II or in combination with any of the formula II embodiments, G' is selected from the group consisting of fluoro, chloro, iodo, methoxyamino, hydroxyamino, —NH(CO)H, —NH(CO)CH$_3$, hydrazino, amino, and cyano. In some aspects G' is selected from the group consisting of fluoro, chloro, iodo, —NH(CO)H, —NH(CO)CH$_3$, amino, and cyano.

In some embodiments of the compounds of formula II or in combination with any of the formula II embodiments, R is methyl. In some aspects Y is O. In other aspects X is $OW^2$ and $W^1$, $W^2$, and $W^3$ are hydrogen. In still other aspects $T^1$ and $T^2$ are hydrogen.

In some embodiments of the compounds of formula II or in combination with any of the formula II embodiments, X is fluoro.

In some embodiments of the compounds of formula II or in combination with any of the formula II embodiments, one of $W^1$ or $W^2$ is a prodrug group.

In another embodiment, a compound of formula II is represented by formula IIa:

IIa wherein:
Q', G', W, W$^1$, and W$^2$ are as described for formula II.

In some embodiments of the compounds of formula Ia or in combination with any of the formula IIa embodiments, Q' is O.

In some embodiments of the compounds of formula IIa or in combination with any of the formula IIa embodiments, G' is selected from the group consisting of azido, amino, aminocarbonyl, acylamino, alkoxyamino, cyano, halo, hydroxyamino, and hydrazino.

In some embodiments of the compounds of formula IIa or in combination with any of the formula Ia embodiments, G' is selected from the group consisting of azido, amino, acylamino, cyano, and halo.

In some embodiments of the compounds of formula IIa or in combination with any of the formula IIa embodiments, G' is selected from the group consisting of fluoro, chloro, iodo, methoxyamino, hydroxyamino, —NH(CO)H, —NH(CO)CH$_3$, hydrazino, amino, aminocarbonyl, and cyano. In some aspects G' is selected from the group consisting of fluoro, chloro, iodo, —NH(CO)H, —NH(CO)CH$_3$, amino, and cyano.

In some embodiments of the compounds of formula Ia or in combination with any of the formula IIa embodiments, Y is O.

In some embodiments of the compounds of formula Ia or in combination with any of the formula Ia embodiments, W, W$^1$, and W$^2$ are hydrogen.

In some embodiments of the compounds of formula IIa or in combination with any of the formula Ia embodiments, one of W$^1$ or W$^2$ is a prodrug group.

The present invention also encompasses a compound of formula III:

III wherein:
A and B are independently selected from the group consisting of C=Q, NH, and methylene optionally substituted with 1 to 2 halo groups, provided that A and B are not both NH;
D is NH, or -D-A-B-together form a —N=CH—NH—, —(C=Q)-CH$_2$—(C=Q)-, —(C=Q)-NH—(C=Q)-, —(CX')=(CX')—(C=Q)-, or —CH=CH—NH— group where X' is halo;
each Q is independently selected from the group consisting of O, S, and NH;
R is selected from the group consisting of hydrogen and C$^1$-C$_3$ alkyl;
X is selected from the group consisting of hydrogen, halo, and OW$^2$;
T$^1$ and T$^2$ are independently selected from the group consisting of hydrogen, hydroxyl, C$^1$-C$_4$-alkoxy, C$^1$-C$_4$-thioalkoxy, amino, substituted amino, and halo;
Y is selected from the group consisting of O and CH$_2$; and
each of W, W$^1$, and W$^2$ is independently selected from the group consisting of hydrogen, C$^1$-C$_4$ alkyl, and a prodrug group; or
a pharmaceutically acceptable salt, a tautomer, or a pharmaceutically acceptable salt of a tautomer thereof.

In some embodiments of the compounds of formula III or in combination with any of the formula III embodiments, A is C=O.

In some embodiments of the compounds of formula III or in combination with any of the formula III embodiments, B is methylene.

In some embodiments of the compounds of formula III or in combination with any of the formula III embodiments, Y is O.

In some embodiments of the compounds of formula III or in combination with any of the formula III embodiments, R is methyl.

In some embodiments of the compounds of formula III or in combination with any of the formula III embodiments, T$^1$ and T$^2$ are hydrogen.

In some embodiments of the compounds of formula III or in combination with any of the formula III embodiments, -D-A-B- together form a —N=CH—NH—, —(C=O)—CH$_2$—(C=O)—, —(C=O)—NH—(C=O)—, —(CF)=(CF)—(C=O)—, or a —CH=CH—NH— group.

In some embodiments of the compounds of formula III or in combination with any of the formula III embodiments, -D-A-B- together form a —N=CH—NH—, —(CX')=(CX')—(C=Q)-, or —CH=CH—NH— group.

In some embodiments of the compounds of formula III or in combination with any of the formula III embodiments, X is fluoro.

In some embodiments of the compounds of formula III or in combination with any of the formula III embodiments, W, W$^1$, and W$^2$ are hydrogen.

In some embodiments of the compounds of formula III or in combination with any of the formula III embodiments, one of W$^1$ or W$^2$ is a prodrug group.

In one embodiment the compounds of formula I, Ia, Ib, Ic, II, IIa, and III, X is O—W$^2$ and each of W, W$^1$, and W$^2$ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^3$NHR$^3$, where R$^{13}$ is hydrogen and R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a side-chain of an amino acid; or $R^3$ and $R^{13}$ together with the carbon and nitrogen atoms bound thereto respectively form a heterocyclic ring. Preferably, W is hydrogen, phospho, diphospho, or triphospho.

In another embodiment compounds of formula I, Ia, Ib, Ic, II, IIa, and III, X is O—$W^2$ and one of W, $W^1$, and $W^2$ is hydrogen. In another embodiment, W and $W^1$ are H, or W and $W^2$ are H, or $W^2$ and $W^1$ are H. In yet another embodiment each of W, $W^1$, and $W^2$ is hydrogen.

In another embodiment compounds of formula I, Ia, Ib, Ic, II, IIa, and III, X is O—$W^2$ and W is represented by the formula:

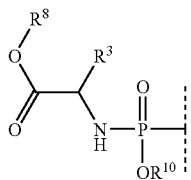

wherein $R^3$ is a side-chain of an amino acid; $R^8$ is hydrogen or alkyl; and $R^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic. Preferably one of $W^1$ and $W^2$ is hydrogen. More preferably $W^1$ and $W^2$ are hydrogen.

In another embodiment compounds of formula I, Ia, Ib, Ic, II, IIa, and III, X is O—$W^2$ and $W^1$ is represented by the formula:

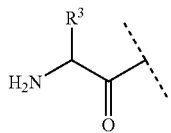

where $R^3$ is a side-chain of an amino acid. Preferably one of W and $W^2$ is hydrogen. More preferably W and $W^2$ are hydrogen.

In one embodiment In another embodiment compounds of formula I, Ia, Ib, Ic, II, and III, X is halo, preferably fluoro, and each of W and $W^1$ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^3$NHR$^{13}$, where R$^{13}$ is hydrogen and R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a side-chain of an amino acid; or R$^3$ and R$^{13}$ together with the carbon and nitrogen atoms bound thereto respectively form a heterocyclic ring. W is preferably hydrogen, phospho, diphospho, or triphospho.

In another embodiment In another embodiment compounds of formula I, Ia, Ib, Ic, II, and III, X is halo, preferably fluoro, and W is represented by the formula:

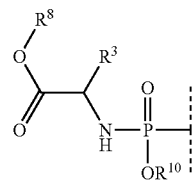

wherein $R^3$ is a side-chain of an amino acid; $R^8$ is hydrogen or alkyl; and $R^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic. Preferably $W^1$ is hydrogen.

In another embodiment In another embodiment compounds of formula I, Ia, Ib, Ic, II, and III, X is halo, preferably fluoro, and $W^1$ is represented by the formula:

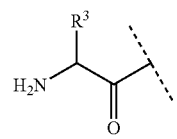

where $R^3$ is a side-chain of an amino acid. Preferably, W is hydrogen.

In one embodiment In another embodiment compounds of formula I, Ia, Ib, Ic, II, IIa, and III, X is O—$W^2$, $W^2$ is $C^{1-4}$alkyl, preferably methyl, and each of W and $W^1$ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^3$NHR$^{13}$, where R$^{13}$ is hydrogen and R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a side-chain of an amino acid; or R$^3$ and R$^{13}$ together with the carbon and nitrogen atoms bound thereto respectively form a heterocyclic ring. Preferably W is hydrogen, phospho, diphospho, or triphospho. More preferably, one of W and $W^1$ is hydrogen. Even more preferably W and $W^1$ are hydrogen.

In one embodiment In another embodiment compounds of formula I, Ia, Ib, Ic, II, IIa, and III, X is O—$W^2$, $W^1$ is $C^{1-4}$alkyl, preferably methyl, and each W and $W^2$ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^3$NHR$^3$, where R$^{13}$ is hydrogen and R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a side-chain of an amino acid; or R$^3$ and R$^{13}$ together with the carbon and nitrogen atoms bound thereto respectively form a heterocyclic ring. Preferably W is hydrogen, phospho, diphospho, or triphospho. More preferably, one of W and $W^2$ is hydrogen. Even more preferably W and $W^2$ are hydrogen.

In one embodiment In another embodiment compounds of formula I, Ia, Ib, Ic, II, IIa, and III, X is O—$W^2$, W is $C^{1-4}$alkyl, preferably methyl, and each of $W^1$ and $W^2$ is independently hydrogen or a pharmaceutically acceptable prodrug group selected from the group consisting of acyl, oxyacyl, phosphonate, phosphate esters, phosphate, phosphonamidate, phosphorodiamidate, phosphoramidate monoester, cyclic phosphoramidate, cyclic phosphorodiamidate, phosphoramidate diester, and —C(O)CHR$^3$NHR$^{13}$, where R$^{13}$ is hydrogen and R$^3$ is selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic and a side-chain of an amino acid; or R$^3$ and R$^{13}$ together with the carbon and nitrogen atoms bound thereto respectively form a heterocyclic ring. More preferably, one of $W^1$ and $W^2$ is hydrogen. Even more preferably $W^1$ and $W^2$ are hydrogen.

In another embodiment In another embodiment compounds of formula I, Ia, Ib, Ic, II, IIa, and III, X is O—W$^2$ and W is represented by the formula:

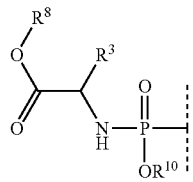

wherein R$^3$ is a side-chain of an amino acid; R$^8$ is hydrogen or alkyl; and R$^{10}$ is selected from the group consisting of alkyl, substituted alkyl, aryl, substituted aryl, cycloalkyl, substituted cycloalkyl, heteroaryl, substituted heteroaryl, heterocyclic and substituted heterocyclic. In another embodiment $W^1$ is hydrogen and $W^2$ is $C^{1-4}$alkyl, preferably methyl. In yet another embodiment $W^2$ is hydrogen and $W^1$ is $C^{1-4}$alkyl, preferably methyl.

In another embodiment compounds of formula I, Ia, Ib, Ic, II, IIa, and III, X is O—W$^2$ and $W^1$ is represented by the formula:

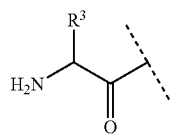

where R$^3$ is a side-chain of an amino acid. In another embodiment W is hydrogen and W$^2$ is methyl. In still another embodiment W$^2$ is hydrogen and W is methyl.

In another embodiment, the present invention encompasses a compound or a pharmaceutically acceptable salt, a tautomer, or a pharmaceutically acceptable salt of a tautomer thereof selected from Table I.

TABLE I

| Cmpd. No. | Structure | Compound Name |
|---|---|---|
| 306 | 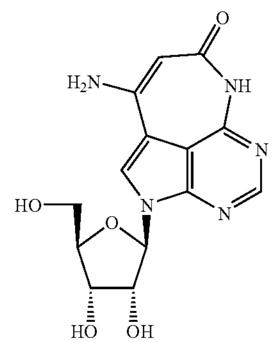 | 9-amino-2-(β-D-ribofuranosyl)-2,6-dihydro-2,3,5,6-tetraaza-benzo[cd]azulen-7-one |
| 307 | 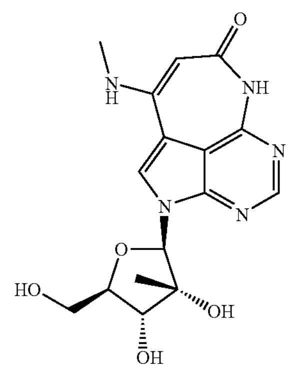 | 2-(2'-methyl-β-D-ribofuranosyl)-9-methylamino-2,6-dihydro-2,3,5,6-tetraaza-benzo[cd]-azulen-7-one |
| 308 | 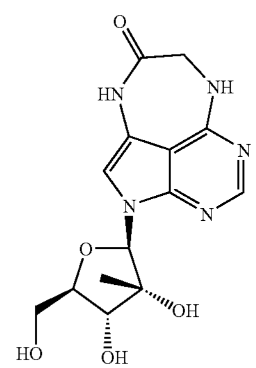 | 2-(2'-methyl-β-D-ribofuranosyl)-2,6,7,9-tetrahydro-2,3,5,6,9-pentaaza-benzo[cd]azulen-8-one |
| 309 | 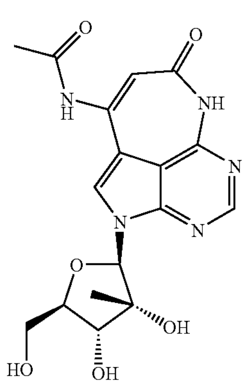 | 9-acetamido-2-(2'-methyl-β-D-ribofuranosyl)-2,6-dihydro-2,3,5,6-tetraaza-benzo[cd]azulen-7-one |

TABLE I-continued

| Cmpd. No. | Structure | Compound Name |
|---|---|---|
| 310 | 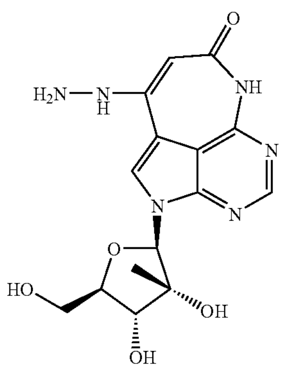 | 9-hydrazino-2-(2'-methyl-β-D-ribofuranosyl)-2,6-dihydro-2,3,5,6-tetraaza-benzo[cd]azulen-7-one |
| 311 | 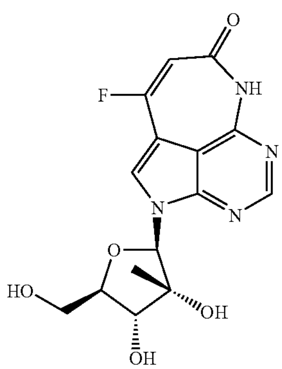 | 9-fluoro-2-(2'-methyl-β-D-ribofuranosyl)-2,6-dihydro-2,3,5,6-tetraaza-benzo[cd]azulen-7-one |
| 312 | 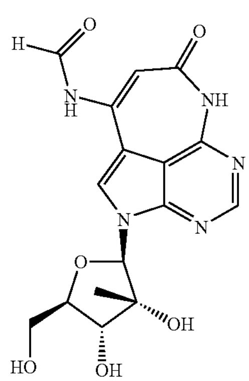 | 9-formamido-2-(2'-methyl-β-D-ribofuranosyl)-2,6-dihydro-2,3,5,6-tetraaza-benzo[cd]azulen-7-one |
| 313 | 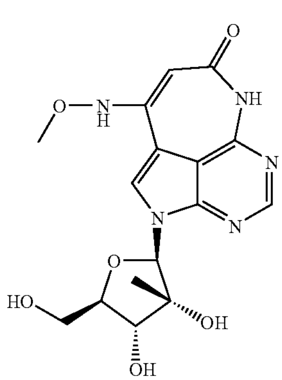 | 9-methoxyamino-2-(2'-methyl-β-D-ribofuranosyl)-2,6-dihydro-2,3,5,6-tetraaza-benzo[cd]azulen-7-one |
| 314 | | 9-amino-2-(2'-methyl-β-D-ribofuranosyl)-2,6-dihydro-2,3,5,6-tetraaza-benzo[cd]azulen-7-one |
| 315 | | 9-hydroxyamino-2-(2'-methyl-β-D-ribofuranosyl)-2,6-dihydro-2,3,5,6-tetraaza-benzo[cd]azulen-7-one |
| 316 | | 8-fluoro-2-(2'-methyl-β-D-ribofuranosyl)-2,6-dihydro-2,3,5,6-tetraaza-benzo[cd]azulen-7-one |
| 317 | | 9-amino-2-(2'-methyl-β-D-ribofuranosyl)-2,6-dihydro-2,3,5,6,8-pentaaza-benzao[cd]azulen-7-one |

TABLE I-continued

| Cmpd. No. | Structure | Compound Name |
|---|---|---|
| 318 | 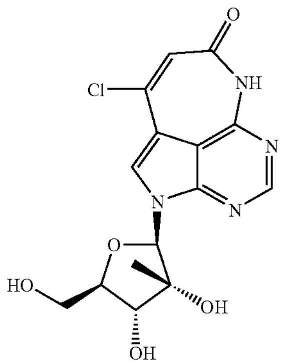 | 9-chloro-2-(2'-methyl-β-D-ribofuranosyl)-2,6-dihydro-2,3,5,6-tetraaza-benzo[cd]-azulen-7-one |
| 319 | 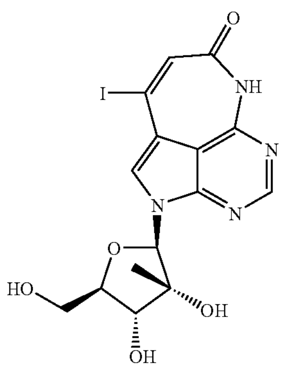 | 9-iodo-2-(2'-methyl-β-D-ribofuranosyl)-2,6-dihydro-2,3,5,6-tetraaza-benzo[cd]-azulen-7-one |
| 320 | 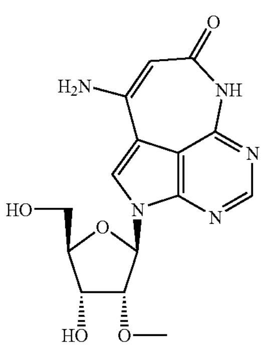 | 9-amino-2-(2'-O-methyl-β-D-ribofuranosyl)-2,6-dihydro-2,3,5,6-tetraaza-benzo[cd]azulen-7-one |
| 321 | 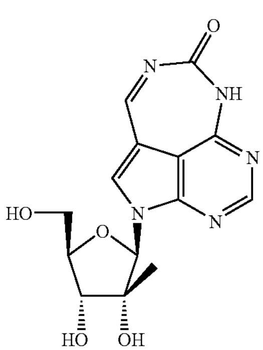 | 2-(2'-methyl-β-D-ribofuranosyl)-2,6-dihydro-2,3,5,6,8-pentaaza-benzao-[cd]azulen-7-one |
| 322 | | 2-(2'-methyl-β-D-ribofuranosyl)-2,6,7,9-tetrahydro-2,3,5,6,7,9-hexaaza-benzo[cd]-azulen-8-one |
| 323 | | 2-(2'-methyl-β-D-ribofuranosyl)-2,9-dihydro-6H-2,3,5,6,9-pentaaza-benzo[cd]azulene-7,8-dione |
| 324 | | 9-cyano-2-(2'-methyl-β-D-ribofuranosyl)-2,6-dihydro-2,3,5,6-tetraaza-benzo[cd]-azulen-7-one |
| 325 | | 9-amino-8-fluoro-2-(2'-methyl-β-D-ribofuranosyl)-2,6-dihydro-2,3,5,6-tetraaza-benzo[cd]azulen-7-one |

TABLE I-continued

| Cmpd. No. | Structure | Compound Name |
|---|---|---|
| 326 | 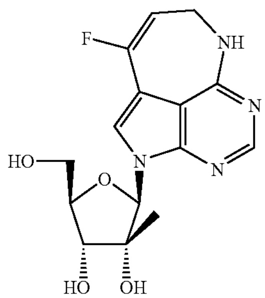 | 9-fluoro-2-(2'-methyl-β-D-ribofuranosyl)-6,7-dihydro-2,3,5,6-tetraaza-benzo[cd]azulene |
| 327 | 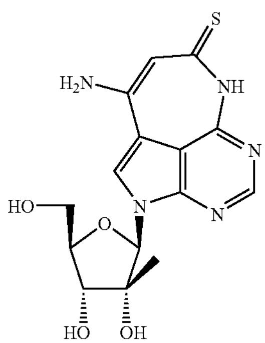 | 9-amino-2-(2'-methyl-β-D-ribofuranosyl)-2,6-dihydro-2,3,5,6-tetraaza-benzo[cd]azulene-7-thione |
| 328 | 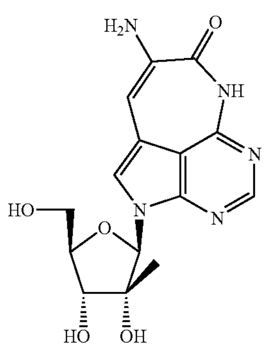 | 8-amino-2-(2'-methyl-β-D-ribofuranosyl)-2,6-dihydro-2,3,5,6-tetraaza-benzo[cd]azulen-7-one |
| 329 | 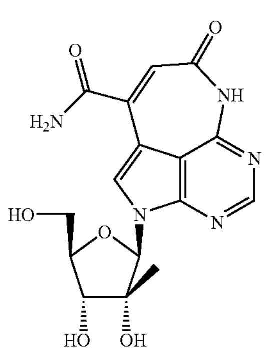 | 9-carbamoyl-2-(2'-methyl-β-D-ribofuranosyl)-2,6-dihydro-2,3,5,6-tetraaza-benzo[cd]azulen-7-one |
| 330 | | 8-cyano-2-(2'-methyl-β-D-ribofuranosyl)-2,6-dihydro-2,3,5,6-tetraaza-benzo[cd]azulen-7-one |
| 331 | | 8-carbamoyl-2-(2'-methyl-β-D-ribofuranosyl)-2,6-dihydro-2,3,5,6-tetraaza-benzo[cd]azulen-7-one |
| 332 | | 2-(2'-methyl-β-D-ribofuranosyl)-6,7-Dihydro-2,3,5,6,7-pentaaza-benzao[cd]azulene |
| 333 | | 2-(2'-methyl-β-D-ribofuranosyl)-6,7-Dihydro-2,3,5,6,7,9-hexaaza-benzao[cd]azulene |

TABLE I-continued

| Cmpd. No. | Structure | Compound Name |
|---|---|---|
| 334 | 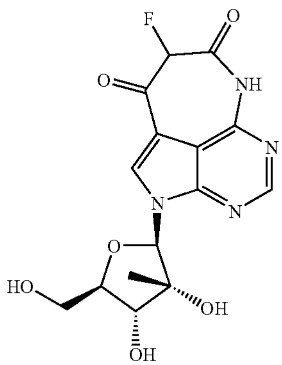 | 8-fluoro-2-(2'-methyl-β-D-ribofuranosyl)-2,6-dihydro-2,3,5,6,-trtraaza-benzo[cd]azulene-7,9-dione |
| 335 | 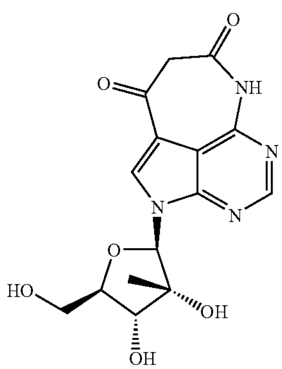 | 2-(2'-methyl-β-D-ribofuranosyl)-2,6-dihydro-2,3,5,6,-trtraaza-benzo[cd]azulene-7,9-dione |
| 336 | 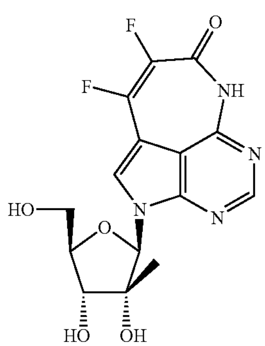 | 8,9-difluoro-2-(2'-methyl-β-D-ribofuranosyl)-2,6-dihydro-2,3,5,6-tetraaza-benzo[cd]azulen-7-one |
| 337 | 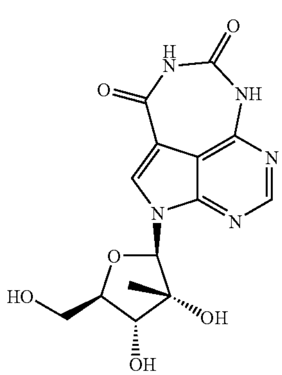 | 2-(2'-methyl-β-D-ribofuranosyl)-2,6-dihydro-2,3,5,6,8-pentaaza-benzao[cd]azulene-7,9-dione |
| 338 | | 9-fluoro-2-(2'-methyl-β-D-ribofuranosyl)-2,6-dihydro-2,3,5,6,8-pentaaza-benzo[cd]azulen-7-one |
| 339 | | 9-fluoro-2-(2'-methyl-]β-D-ribofuranosyl)-6,7-dihydro-2,3,5,6-tetraaza-benzo[cd]-azulene |

In other embodiments, present invention ecompasses the 5' mono-, di-, and triphosphates of the compounds of Table 1.

In one embodiment, the 5' monophosphates are selected from the group consisting of 9-amino-2-(5'-phospho-β-D-ribofuranosyl)-2,6-dihydro-2,3,5,6-tetraaza-benzo[cd]azulen-7-one;

2-(2'-methyl-5'-phospho-β-D-ribofuranosyl)-9-methylamino-2,6-dihydro-2,3,5,6-tetraaza-benzo[cd]azulen-7-one;

2-(2'-methyl-5'-phospho-β-D-ribofuranosyl)-2,6,7,9-tetrahydro-2,3,5,6,9-pentaaza-benzo[cd]azulen-8-one;

9-acetamido-2-(2'-methyl-5'-phospho-β-D-ribofuranosyl)-2,6-dihydro-2,3,5,6-tetraaza-benzo[cd]azulen-7-one;

9-hydrazino-2-(2'-methyl-5'-phospho-β-D-ribofuranosyl)-2,6-dihydro-2,3,5,6-tetraaza-benzo[cd]azulen-7-one;

9-fluoro-2-(2'-methyl-5'-phospho-β-D-ribofuranosyl)-2,6-dihydro-2,3,5,6-tetraaza-benzo[cd]azulen-7-one;

9-formamido-2-(2'-methyl-5'-phospho-β-D-ribofuranosyl)-2,6-dihydro-2,3,5,6-tetraaza-benzo[cd]azulen-7-one;

9-methoxyamino-2-(2'-methyl-5'-phospho-β-D-ribofuranosyl)-2,6-dihydro-2,3,5,6-tetraaza-benzo[cd]azulen-7-one;

9-amino-2-(2'-methyl-5'-phospho-β-D-ribofuranosyl)-2,6-dihydro-2,3,5,6-tetraaza-benzo[cd]azulen-7-one;

9-hydroxyamino-2-(2'-methyl-5'-phospho-β-D-ribofuranosyl)-2,6-dihydro-2,3,5,6-tetraaza-benzo[cd]azulen-7-one;

8-fluoro-2-(2'-methyl-5'-phospho-β-D-ribofuranosyl)-2,6-dihydro-2,3,5,6-tetraaza-benzo[cd]azulen-7-one;

9-amino-2-(2'-methyl-5'-phospho-β-D-ribofuranosyl)-2,6-dihydro-2,3,5,6,8-pentaaza-benzo[cd]azulen-7-one;

9-chloro-2-(2'-methyl-5'-phospho-β-D-ribofuranosyl)-2,6-dihydro-2,3,5,6-tetraaza-benzo[cd]azulen-7-one;

9-iodo-2-(2'-methyl-5'-phospho-β-D-ribofuranosyl)-2,6-dihydro-2,3,5,6-tetraaza-benzo[cd]azulen-7-one;

9-amino-2-(2'-O-methyl-5'-phospho-β-D-ribofuranosyl)-2,
6-dihydro-2,3,5,6-tetraaza-benzo[cd]azulen-7-one; and
2-(2'-methyl-5'-phospho-β-D-ribofuranosyl)-2,6-dihydro-2,
3,5,6,-trtraaza-benzo[cd]azulene-7,9-dione.

In one embodiment, the 5' diphosphates are selected from the group consisting of
9-amino-2-(5'-diphospho-β-D-ribofuranosyl)-2,6-dihydro-2,3,5,6-tetraaza-benzo[cd]azulen-7-one;
2-(2'-methyl-5'-diphospho-β-D-ribofuranosyl)-9-methylamino-2,6-dihydro-2,3,5,6-tetraaza-benzo[cd]azulen-7-one;
2-(2'-methyl-5'-diphospho-β-D-ribofuranosyl)-2,6,7,9-tetrahydro-2,3,5,6,9-pentaaza-benzo[cd]azulen-8-one;
9-acetamido-2-(2'-methyl-5'-diphospho-β-D-ribofuranosyl)-2,6-dihydro-2,3,5,6-tetraaza-benzo[cd]azulen-7-one;
9-hydrazino-2-(2'-methyl-5'-diphospho-β-D-ribofuranosyl)-2,6-dihydro-2,3,5,6-tetraaza-benzo[cd]azulen-7-one;
9-fluoro-2-(2'-methyl-5'-diphospho-β-D-ribofuranosyl)-2,6-dihydro-2,3,5,6-tetraaza-benzo[cd]azulen-7-one;
9-formamido-2-(2'-methyl-5'-diphospho-β-D-ribofuranosyl)-2,6-dihydro-2,3,5,6-tetraaza-benzo[cd]azulen-7-one;
9-methoxyamino-2-(2'-methyl-5'-diphospho-β-D-ribofuranosyl)-2,6-dihydro-2,3,5,6-tetraaza-benzo[cd]azulen-7-one;
9-amino-2-(2'-methyl-5'-diphospho-β-D-ribofuranosyl)-2,6-dihydro-2,3,5,6-tetraaza-benzo[cd]azulen-7-one;
9-hydroxyamino-2-(2'-methyl-5'-diphospho-β-D-ribofuranosyl)-2,6-dihydro-2,3,5,6-tetraaza-benzo[cd]azulen-7-one;
8-fluoro-2-(2'-methyl-5'-diphospho-β-D-ribofuranosyl)-2,6-dihydro-2,3,5,6-tetraaza-benzo[cd]azulen-7-one;
9-amino-2-(2'-methyl-5'-diphospho-β-D-ribofuranosyl)-2,6-dihydro-2,3,5,6,8-pentaaza-benzo[cd]azulen-7-one;
9-chloro-2-(2'-methyl-5'-diphospho-β-D-ribofuranosyl)-2,6-dihydro-2,3,5,6-tetraaza-benzo[cd]azulen-7-one;
9-iodo-2-(2'-methyl-5'-diphospho-β-D-ribofuranosyl)-2,6-dihydro-2,3,5,6-tetraaza-benzo[cd]azulen-7-one;
9-amino-2-(2'-O-methyl-5'-diphospho-β-D-ribofuranosyl)-2,6-dihydro-2,3,5,6-tetraaza-benzo[cd]azulen-7-one; and
2-(2'-methyl-5'-diphospho-β-D-ribofuranosyl)-2,6-dihydro-2,3,5,6,-trtraaza-benzo[cd]azulene-7,9-dione.

In one embodiment, the 5' tri-phosphates are selected from the group consisting of
9-amino-2-(5'-triphospho-β-D-ribofuranosyl)-2,6-dihydro-2,3,5,6-tetraaza-benzo[cd]azulen-7-one;
2-(2'-methyl-5'-triphospho-β-D-ribofuranosyl)-9-methylamino-2,6-dihydro-2,3,5,6-tetraaza-benzo[cd]azulen-7-one;
2-(2'-methyl-5'-triphospho-β-D-ribofuranosyl)-2,6,7,9-tetrahydro-2,3,5,6,9-pentaaza-benzo[cd]azulen-8-one;
9-acetamido-2-(2'-methyl-5'-triphospho-β-D-ribofuranosyl)-2,6-dihydro-2,3,5,6-tetraaza-benzo[cd]azulen-7-one;
9-hydrazino-2-(2'-methyl-5'-triphospho-β-D-ribofuranosyl)-2,6-dihydro-2,3,5,6-tetraaza-benzo[cd]azulen-7-one;
9-fluoro-2-(2'-methyl-5'-triphospho-β-D-ribofuranosyl)-2,6-dihydro-2,3,5,6-tetraaza-benzo[cd]azulen-7-one;
9-formamido-2-(2'-methyl-5'-triphospho-β-D-ribofuranosyl)-2,6-dihydro-2,3,5,6-tetraaza-benzo[cd]azulen-7-one;
9-methoxyamino-2-(2'-methyl-5'-triphospho-β-D-ribofuranosyl)-2,6-dihydro-2,3,5,6-tetraaza-benzo[cd]azulen-7-one;
9-amino-2-(2'-methyl-5'-triphospho-β-D-ribofuranosyl)-2,6-dihydro-2,3,5,6-tetraaza-benzo[cd]azulen-7-one;
9-hydroxyamino-2-(2'-methyl-5'-triphospho-β-D-ribofuranosyl)-2,6-dihydro-2,3,5,6-tetraaza-benzo[cd]azulen-7-one;
8-fluoro-2-(2'-methyl-5'-triphospho-β-D-ribofuranosyl)-2,6-dihydro-2,3,5,6-tetraaza-benzo[cd]azulen-7-one;
9-amino-2-(2'-methyl-5'-triphospho-β-D-ribofuranosyl)-2,6-dihydro-2,3,5,6,8-pentaaza-benzo[cd]azulen-7-one;
9-chloro-2-(2'-methyl-5'-triphospho-β-D-ribofuranosyl)-2,6-dihydro-2,3,5,6-tetraaza-benzo[cd]azulen-7-one;
9-iodo-2-(2'-methyl-5'-triphospho-β-D-ribofuranosyl)-2,6-dihydro-2,3,5,6-tetraaza-benzo[cd]azulen-7-one;
9-amino-2-(2'-O-methyl-5'-triphospho-β-D-ribofuranosyl)-2,6-dihydro-2,3,5,6-tetraaza-benzo[cd]azulen-7-one; and
2-(2'-methyl-5'-triphospho-β-D-ribofuranosyl)-2,6-dihydro-2,3,5,6,-trtraaza-benzo[cd]azulene-7,9-dione.

In another embodiment, the present invention encompasses a pharmaceutical composition comprising a pharmaceutically acceptable carrier and a therapeutically effective amount of a compound or a pharmaceutically acceptable salt, a tautomer, or a pharmaceutically acceptable salt of a tautomer thereof, represented by formula I, Ia, Ib, Ic, II, IIa, or III or a mixture of two or more of such compounds.

In another embodiment, the present invention encompasses a method for treating or preventing a viral infection in a mammal mediated at least in part by a virus in the Flaviviridae family of viruses, comprising administering to said mammal a encompasses a pharmaceutical composition comprising a pharmaceutically acceptable carrier and a therapeutically effective amount of a compound or a pharmaceutically acceptable salt, a tautomer, or a pharmaceutically acceptable salt of a tautomer thereof, represented by formula I, Ia, Ib, Ic, II, IIa, or III or a mixture of two or more of such compounds.

In other embodiments, the present invention encompasses use of a compound or a pharmaceutically acceptable salt, a tautomer, or a pharmaceutically acceptable salt of a tautomer thereof, represented by formula I, Ia, Ib, Ic, II, IIa, or III in the preparation of a medicament for treating or preventing a viral infection in a mammal mediated at least in part by a virus in the Flaviviridae family of viruses.

In some aspects, the mammal is a human.

in some aspects, the viral infection is a hepatitis C mediated viral infection.

In other aspects, the administration of a therapeutically effective amount of the compounds of the invention are used in combination with one or more agents active against hepatitis C virus.

In some embodiments, the agent active against hepatitis C virus is an inhibitor of HCV proteases, HCV polymerase, HCV helicase, HCV NS4B protein, HCV entry, HCV assembly, HCV egress, HCV NS5A protein, or inosine 5'-monophosphate dehydrogenase.

In other embodiments, the active agent against HCV is Ribavirin, levovirin, viramidine, thymosin alpha-1, an inhibitor of NS3 serine protease, an inhibitor of inosine monophosphate dehydrogenase, interferon-alpha, or pegylated interferon-alpha.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of this invention may range from approximately 0.01 to 50 mg per kilogram body weight of the recipient per day; preferably about 0.01-25 mg/kg/day, more preferably about 0.01-10 mg/kg/day, still more preferably from about 0.01 to 5 mg/kg/day. Thus, for administration to a 70 kg person, the dosage range would most preferably be about 0.7-350 mg per day.

In general, compounds of this invention will be administered as pharmaceutical compositions by any one of the following routes: oral, systemic (e.g., transdermal, intranasal or by suppository), parenteral (e.g., intramuscular, intravenous or subcutaneous), or intrathecal administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of this invention is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions may be comprised of a compound of this invention in combination with at least one pharmaceutically acceptable excipient. Acceptable excipients are non-toxic, aid administration, and do not adversely affect the therapeutic benefit of the compound of this invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of this invention based on the total formulation, with the balance being one or more suitable pharmaceutical excipients. Preferably, the compound is present at a level of about 1-80 wt %.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, Ribavirin, levovirin, viramidine, thymosin alpha-1, an inhibitor of HCV NS3 serine protease, or an inhibitor of inosine monophosphate dehydrogenase, interferon-$\alpha$, pegylated interferon-$\alpha$ (peginterferon-$\alpha$), a combination of interferon-$\alpha$ and Ribavirin, a combination of peginterferon-$\alpha$ and Ribavirin, a combination of interferon-$\alpha$ and levovirin, and a combination of peginterferon-$\alpha$ and levovirin. Interferon-$\alpha$ includes, but is not limited to, recombinant interferon-$\alpha$2a (such as ROFERON interferon available from Hoffman-LaRoche, Nutley, N.J.), interferon-$\alpha$2b (such as Intron-A interferon available from Schering Corp., Kenilworth, N.J., USA), a consensus interferon, and a purified interferon-$\alpha$ product. For a discussion of Ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201-210 (2000).

The agents active against hepatitis C virus also include agents that inhibit HCV proteases, HCV polymerase, HCV helicase, HCV NS4B protein, HCV entry, HCV assembly, HCV egress, HCV NS5A protein, and inosine 5'-monophosphate dehydrogenase. Other agents include nucleoside analogs for the treatment of an HCV infection. Still other compounds include those disclosed in WO 2004/014313 and WO 2004/014852 and in the references cited therein. The patent applications WO 2004/014313 and WO 2004/014852 are hereby incorporated by references in their entirety.

Specific antiviral agents include Omega IFN (BioMedicines Inc.), BILN-2061 (Boehringer Ingelheim), Summetrel (Endo Pharmaceuticals Holdings Inc.), Roferon A (F. Hoffman-La Roche), Pegasys (F. Hoffman-La Roche), Pegasys/Ribaravin (F. Hoffman-La Roche), CellCept (F. Hoffman-La Roche), Wellferon (GlaxoSmithKline), Albuferon-$\alpha$ (Human Genome Sciences Inc.), Levovirin (ICN Pharmaceuticals), IDN-6556 (Idun Pharmaceuticals), IP-501 (Indevus Pharmaceuticals), Actimmune (InterMune Inc.), Infergen A (InterMune Inc.), ISIS 14803 (ISIS Pharamceuticals Inc.), JTK-003 (Japan Tobacco Inc.), Pegasys/Ceplene (Maxim Pharmaceuticals), Ceplene (Maxim Pharmaceuticals), Civacir (Nabi Biopharmaceuticals Inc.), Intron A/Zadaxin (RegeneRx), Levovirin (Ribapharm Inc.), Viramidine (Ribapharm Inc.), Heptazyme (Ribozyme Pharmaceuticals), Intron A (Schering-Plough), PEG-Intron (Schering-Plough), Rebetron (Schering-Plough), Ribavirin (Schering-Plough), PEG-Intron/Ribavirin (Schering-Plough), Zadazim (SciClone), Rebif (Serono), IFN-β/EMZ701 (Transition Therapeutics), T67 (Tularik Inc.), VX-497 (Vertex Pharmaceuticals Inc.), VX-950/LY-570310 (Vertex Pharmaceuticals Inc.), Omniferon (Viragen Inc.), XTL-002 (XTL Biopharmaceuticals), SCH 503034 (Schering-Plough), isatoribine and its prodrugs ANA971 and ANA975 (Anadys), R1479 (Roche Biosciences), Valopicitabine (Idenix), NIM811 (Novartis), and Actilon (Coley Pharmaceuticals).

In some embodiments, the active agent against hepatitis C virus is interferon. In some aspects, the interferon is selected from the group consisting of interferon alpha 2B, pegylated interferon alpha, consensus interferon, interferon alpha 2A, and lymphoblastiod interferon tau.

In other embodiments the active agent against hepatitis C virus is a compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'monophospate dehydrogenase inhibitor, amantadine, and rimantadine.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989). Specifically, the compounds of this invention may be prepared by various methods known in the art of organic chemistry in general and nucleoside and nucleotide analogue synthesis in particular. General reviews of the preparation of nucleoside and nucleotide analogues include 1) Michelson A. M. "*The Chemistry of Nucleosides and Nucleotides*," Academic Press, New York, 1963; 2) Goodman L. "*Basic Principles in Nucleic Acid Chemistry*," Academic Press, New York, 1974, vol. 1, Ch. 2; and 3) "*Synthetic Procedures in Nucleic Acid Chemistry*," Eds. Zorbach W. & Tipson R., Wiley, New York, 1973, vol. 1 & 2.

In one embodiment, the synthesis of certain compounds of this invention proceeds via the 7-(2'-methyl-β-D-ribofuranosyl)-4-amino-5-iodopyrrolo[2,3-d]pyrimidine, compound 1, the synthesis of which is described in Scheme 1 below (where DCB is dichlorobenzyl) and is also described in U.S. patent application Ser. No. 10/861,090, filed Jun. 4, 2004 which application is incorporated herein by reference in its entirety.

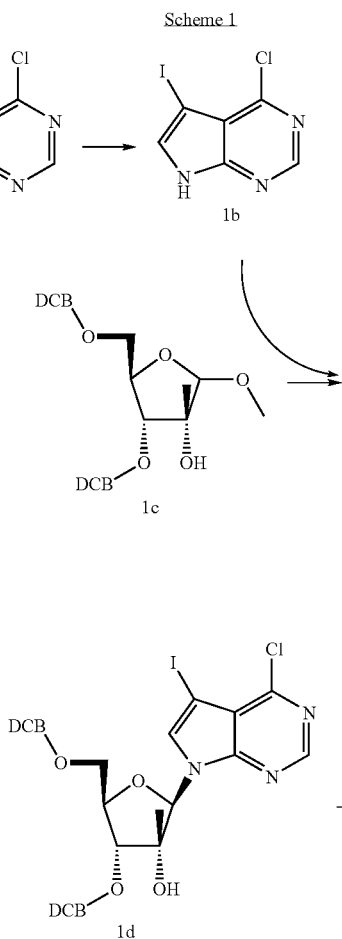

-continued

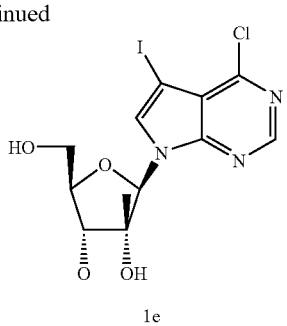

1e

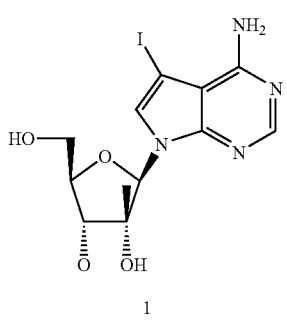

1

Specifically, in Scheme 1, known 4-chloro-1H-pyrrolo[2,3-d]pyrimidine (Example 62, Step D, Carroll, et al.[18]), compound 1a, is converted to the corresponding 4-chloro-5-iodo-1H-pyrrolo[2,3-d]pyrimidine, compound 1b, by iodination with N-iodosuccinimide. Specifically, the reaction is typically conducted by combining a slight stoichiometric excess (about 1.05 to 1.10 equivalents) of N-iodsuccinimide with 4-chloro-1H-pyrrolo[2,3-d]pyrimidine, compound 1a. The reaction is preferably conducted under ambient conditions in the absence of light in a suitable solvent such as N,N-dimethylformamide. The reaction is continued until substantially complete which occurs in about 2 to 24 hours to produce 4-chloro-5-iodo-1H-pyrrolo[2,3-d]pyrimidine, compound 1b. Upon reaction completion, compound 1b is recovered by conventional methods including neutralization, evaporation, extraction, precipitation, chromatography, filtration, and the like, or, alternatively, is used in the next reaction without purification and/or isolation.

4-Chloro-5-iodo-1H-pyrrolo[2,3-d]pyrimidine, compound 1b, is then coupled to a protected 2-methyl substituted sugar the synthesis of which is described, for example, by Carroll, et al.,[17,18] using conditions well known in the art to provide for the 3,5-di-O-protected 7-deazapurine compound. For example, known 1-O-methyl-3,5-di-(O-2,4-dichlorobenzyl)-2-C-methyl-D-ribofuranoside, compound 1c, is dissolved in a dry inert solvent, such as dichloromethane, chloroform, carbon tetrachloride and the like, and then the solution is cooled to about 0° C. Afterwards, an excess of HBr or other appropriate reagent, in acetic acid, is added drop wise. This reaction is typically run about 1 to about 4 hours at temperature at about 0 to about 25° C., or until substantially complete as determined by conventional techniques such as TLC. The resulting brominated sugar mixture (not shown) is isolated and purified using standard techniques such as chromatography, precipitation, crystallization, filtration, and the like. Alternatively this intermediate may be isolated and used in the next step without further purification. The resulting brominated sugar mixture is co-evaporated, preferably with dry toluene, dissolved in a suitable inert diluent such as dry acetonitrile and stirred with the sodium salt of 4-chloro-5-iodo-1H-pyrrolo[2,3-d]pyrimidine (not shown) at room temperature over night. The resulting compound 1d, 7-(2'-methyl-3',5'-di-(O-2,4-dichlorobenzyl)-β-D-ribofuranosyl)-4-chloro-5-iodopyrrolo[2,3-d]pyrimidine, is isolated and purified using standard techniques such as chromatography, precipitation, crystallization, filtration, and the like. Alternatively, this intermediate may be isolated and used in the next step without further purification.

The sodium salt of 4-chloro-5-iodo-1H-pyrrolo[2,3-d]pyrimidine is prepared in an inert atmosphere by suspending compound 1b in a dry inert solvent such as, acetonitrile and the like, with NaH dispersed in oil. The reaction is run for about 2 to about 24 hours at a temperature of about 0 to about 40° C.

The 2,4-dichlorobenzyl protecting groups at the 3,5-positions of compound 1d are removed under conventional conditions such as contact with an excess of boron trichloride in a suitable solvent such as dichloromethane, chloroform, and the like, to provide for 7-(2'-methyl-β-D-ribofuranosyl)-4-chloro-5-iodopyrrolo[2,3-d]pyrimidine, compound 1e. Specifically, the reaction is preferably conducted at a temperature of from about 0 to about −80° C. until the reaction is substantially complete which occurs in about 0.2 to 2 hours to produce compound 1e. Upon reaction completion, compound 1e is recovered by conventional methods including neutralization, evaporation, extraction, precipitation, chromatography, filtration, and the like, or, alternatively, is used in the next reaction without purification and/or isolation.

Conversion of compound 1e to 7-(2'-methyl-β-D-ribofuranosyl)-4-amino-5-iodopyrrolo[2,3-d]pyrimidine, compound 1 is achieved, for example, by contacting compound 1e with an excess of liquid ammonia. In one embodiment, the reaction is conducted at about 85° C. at elevated pressures until the reaction is substantially complete which typically occurs in about 12 to about 48 hours. Compound 1 is then isolated and purified using standard techniques such as chromatography, precipitation, crystallization, filtration, and the like.

Compound 1 can then be used as a key intermediate in the synthesis of compounds of this invention.

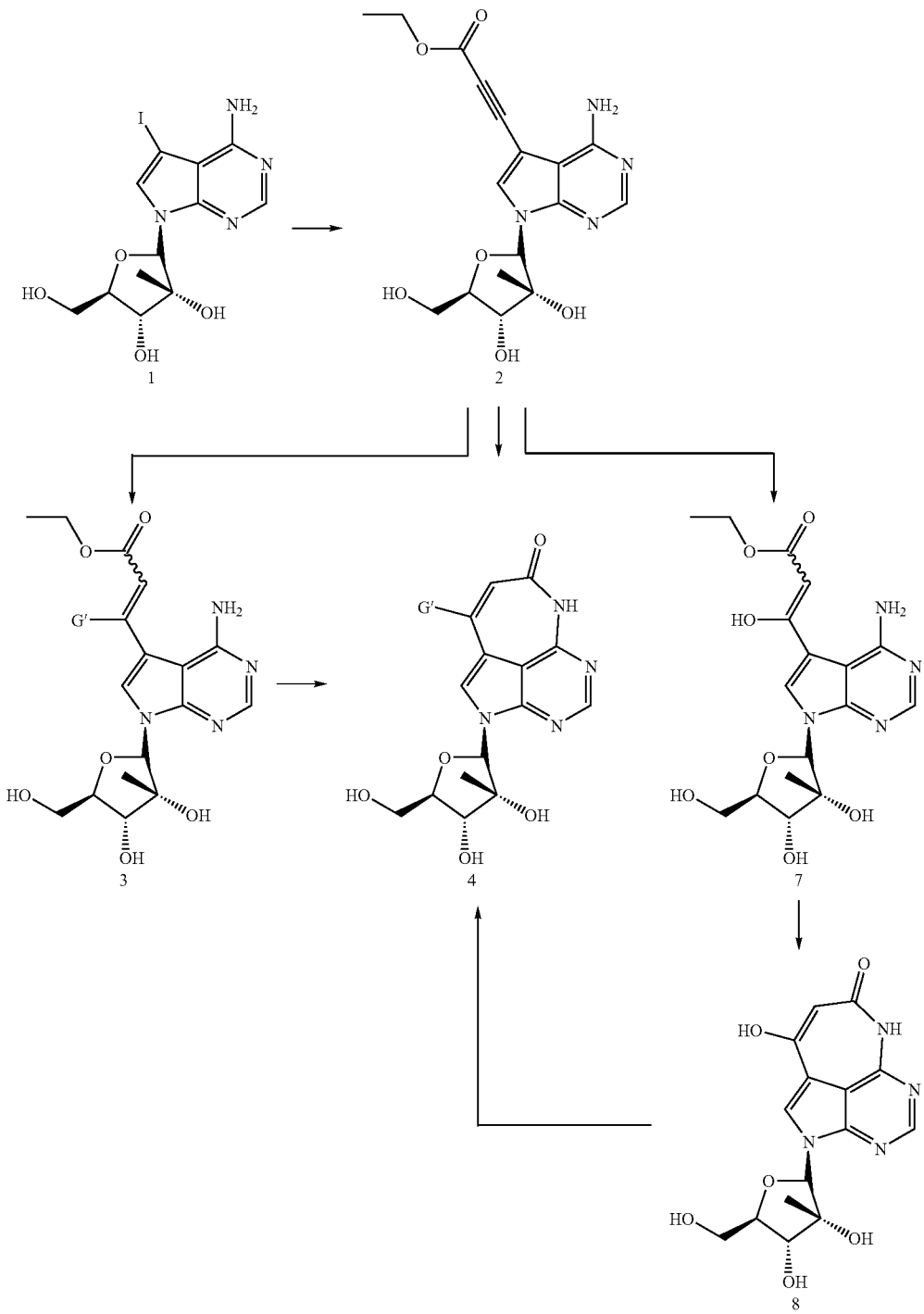

Scheme 2

In Scheme 2, compound 1, described above, is converted first to the 7-(2'-C-methyl-β-D-ribofuranosyl)-4-amino-5-[(2-ethoxycarbonyl)ethyn-1-yl]-pyrrolo[2,3-d]pyrimidine, compound 2, by contacting compound 1 with ethyl propiolate in the presence of CuI, a Pd(0) catalyst, and tertiary amine base in a suitable solvent such as DMF. In one embodiment, compound 2 is converted directly to 9-chloro-2-(2'-methyl-β-D-ribofuranosyl)-2,6-dihydro-2,3,5,6-tetraaza-benzo[cd]azulen-7-one, compound 4, by contact with the lithium chloride in acetic acid at 80° C. Alternatively, the addition of appropriate G' group to compound 2 gives intermediate compound 3 and the cyclization to compound 4 requires heating in an ethanolic solution containing several equivalences of alkoxide base.

Alternatively, when G' is a halogen group, compound 4 can be used as an intermediate. The halogen can be replaced by contacting with a suitable nucleophile via an addition-elimination reaction. For example compounds where G' is alkoxy can be made in this fashion.

In another embodiment, compound 2 is derivatized to compound 7, by reaction with mercury sulfate in aqueous alcoholic solvent at elevated temperatures. In turn, compound 7 is cyclized in the manner described above, for converting compound 3 to compound 4, to give compound 8. Compound 8 has tautomeric forms, one set of its tautomeric forms has the following structures:

Specifically, in Scheme 3, conversion of the 4-methylthio derivative, compound 9 to the corresponding 4-hydrogen derivative, compound 10 proceeds via contact with Raney nickel in boiling alcoholic solvent. Alternatively, the 4-methylthio derivative, compound 9 can be converted to the corresponding compound 11 via contact with a suitable organic peroxyacid in an appropriate solvent followed by treatment with NaSH. Alternatively, the 4-methylthio derivative, compound 9 can be converted to the corresponding oxo compound 12 by contact with a suitable organic peroxyacid in an

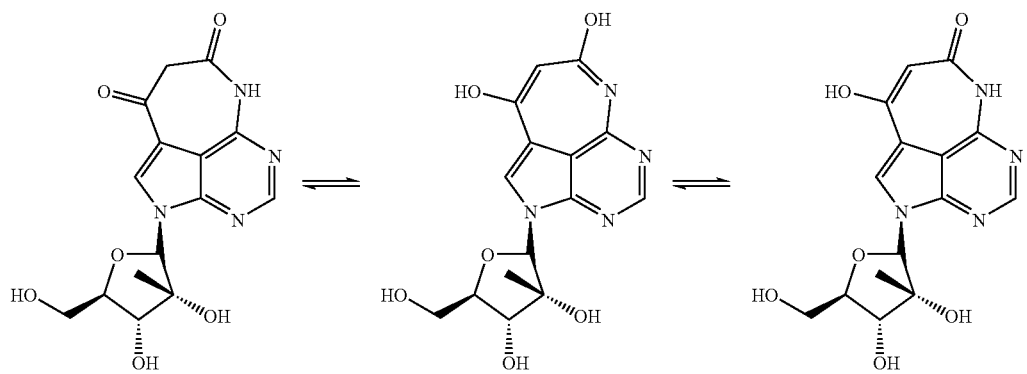

all of which are covered by this invention.

Additionally, certain G' groups of compound 4 can be made from compound 8 with a suitable reagent, as illustrated in the Example section.

Further compounds of formula I can be prepared as shown in Scheme 3 below. Compounds 9 is prepared in a manner described above in Schemes 1 and 2, where 4-chloro-2-methylthio-1H-pyrrolo[2,3-d]pyrimidine is used in place of compound 1a.

appropriate solvent followed by heating in an aqueous hydroxide solution. If an alkoxy solution in alcohol solvent such as sodium methoxide in methanol is used instead of aqueous hydroxide, compound 13 results.

Compounds 11, and 12 have tautomeric forms, one set of its tautomeric forms has the following structures:

Scheme 3

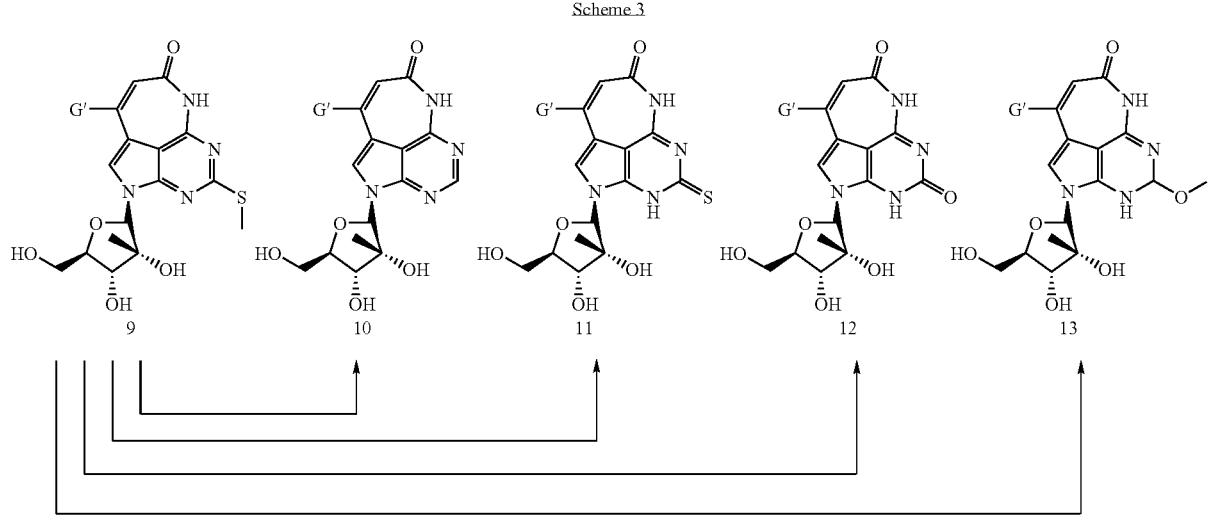

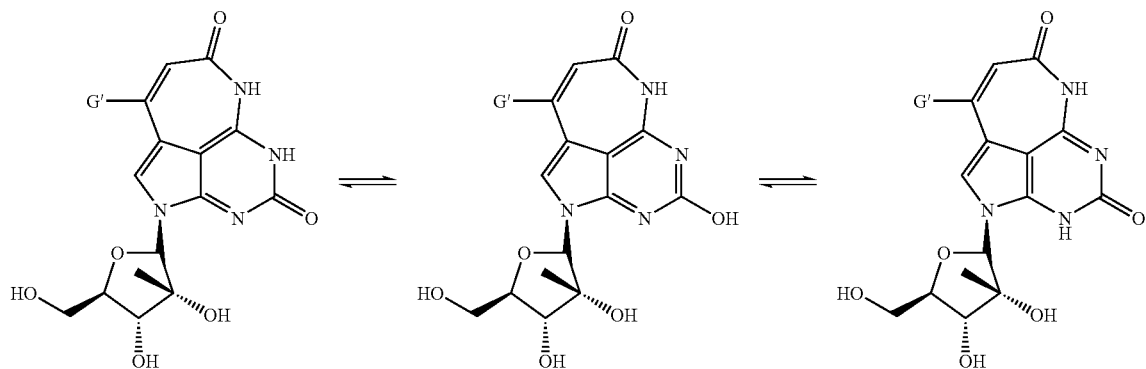
all of which are covered by this invention.
Scheme 4 below illustrates synthetic methods for forming a thiocarbonyl group on the lactam ring.
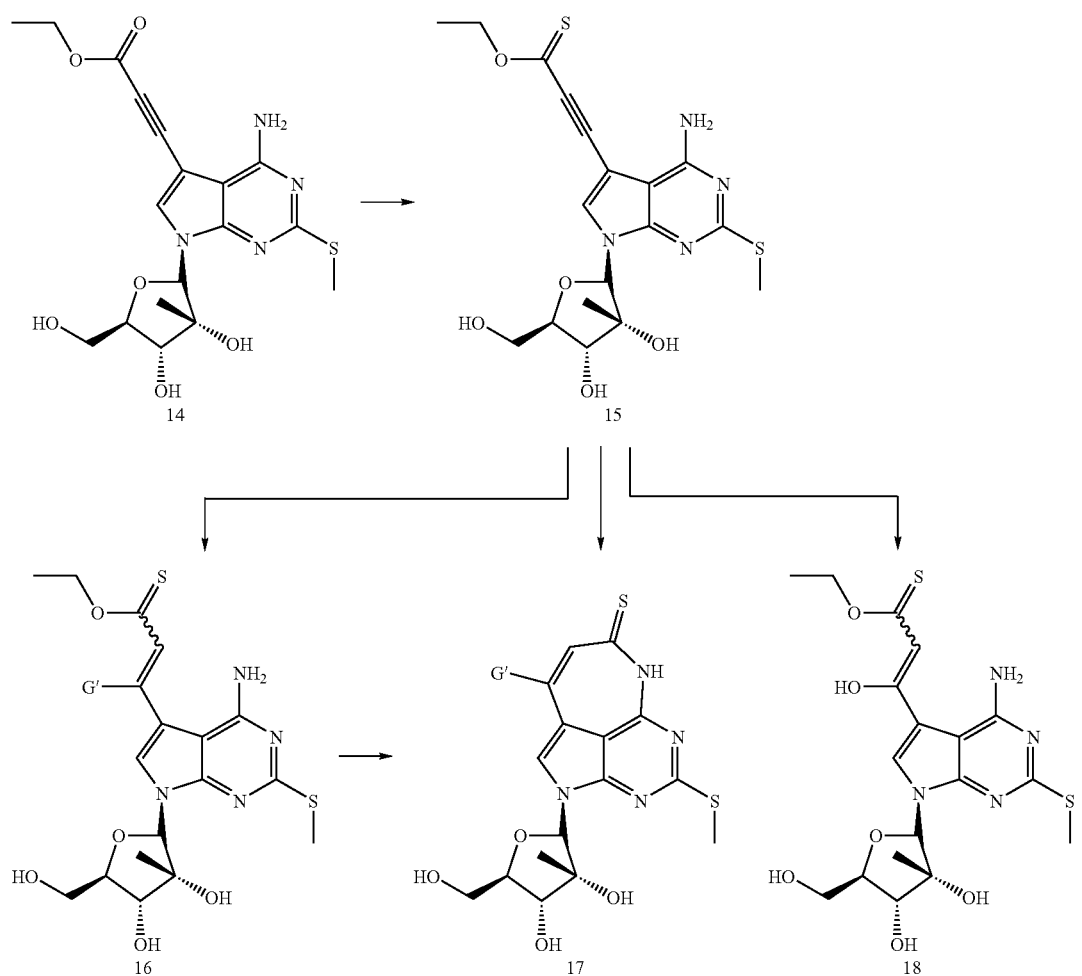

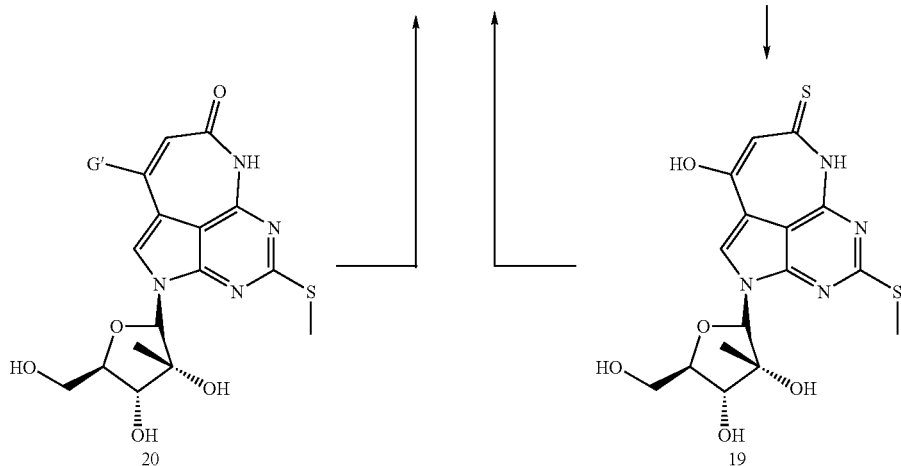

Compound 14 is prepared in a manner described for compound 2 above in Schemes 1 and 2, with the exception that 4-chloro-2-methylthio-1H-pyrrolo[2,3-d]pyrimidine is used in place of compound 1a in scheme 1. Protection of the alcohol moieties of the sugar with appropriate groups then contacting the nucleoside with Lawesson's reagent in a suitable solvent at elevated temperature gives compound 15. Compound 15 is then treated as described for compound 2 in Scheme 2 to yield compound 17, the thiocarbonyl derivative of compound 4.

Alternatively, from compound 9 in Scheme 3, the sugar alcohol moieties and in some cases G' as well, are protected with an appropriate group or groups and the resulting compound is boiled in $P_2S_5$. The removal of the protecting groups provides for compound 17.

Scheme 5 below illustrates the synthesis of diazepine compounds.

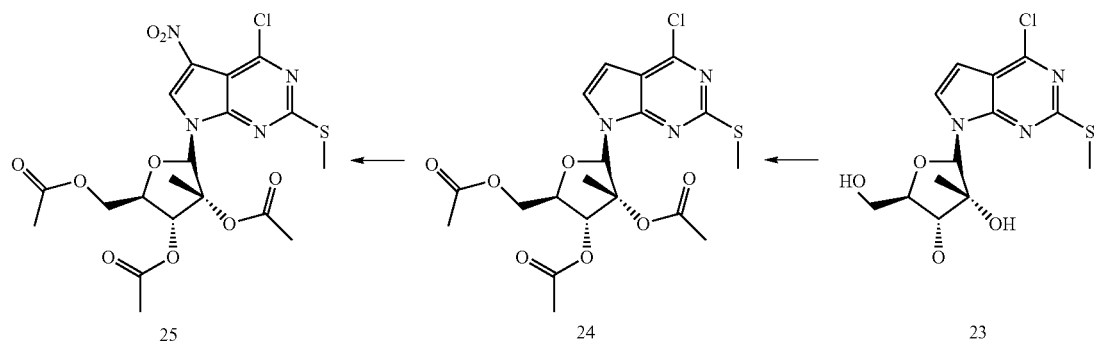

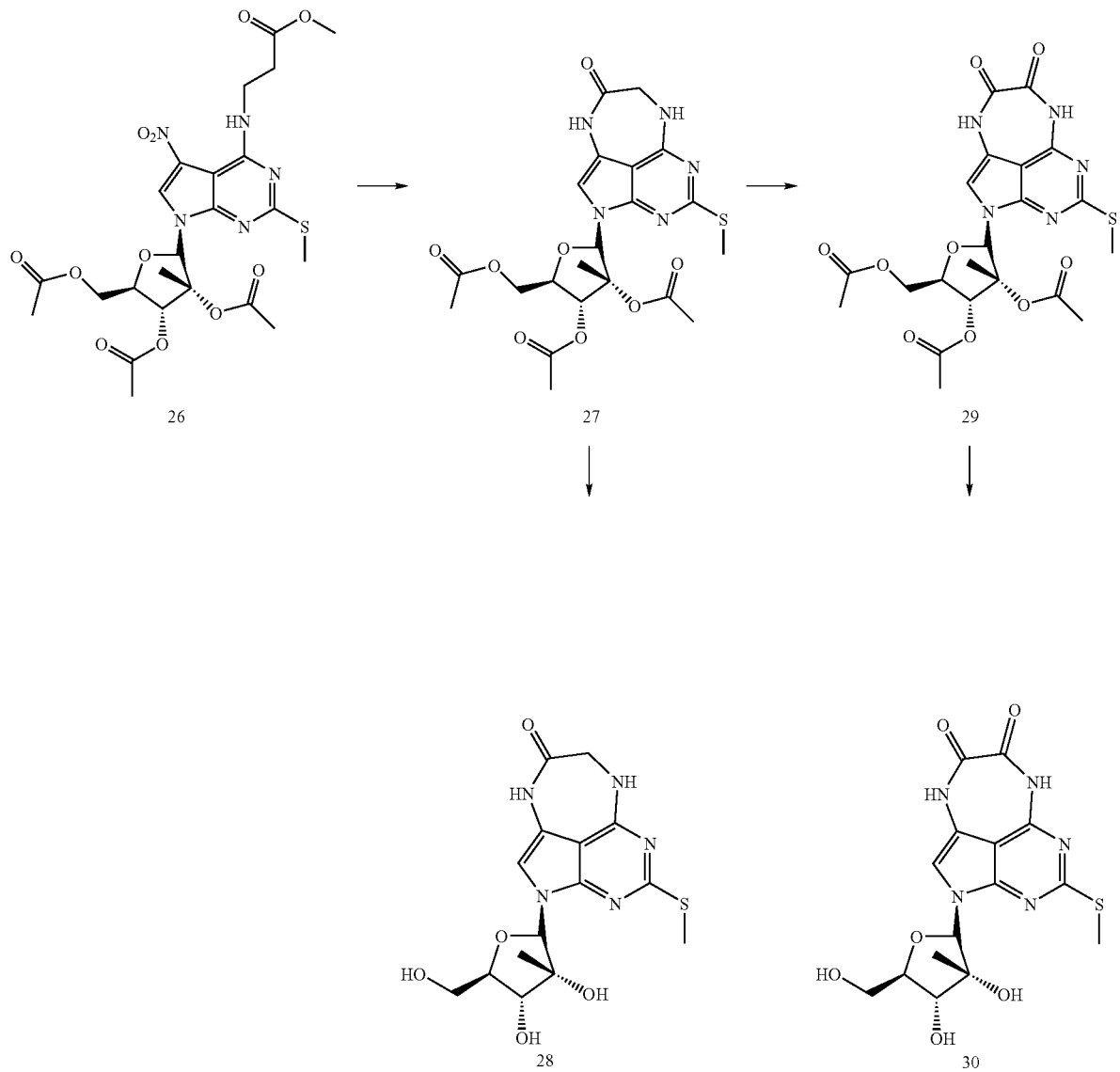

Specifically, in Scheme 5, compound 23, is converted to the corresponding 2,3,5-tri-O-protected sugar, compound 24, by contact with acetyl chloride in acetic acid. In turn, compound 24 is converted to the 5-nitro derivative, compound 25, by contact with a mixture of nitric and sulfuric acid in a suitable solvent such as DCM. Conversion of compound 25 to compound 26 is accomplished by contact with glycine methylester at elevated temperature in a suitable solvent such as ETOH, DMF and the like. Conversion to compound 27 is accomplished via palladium catalyzed hydrogenation in the presence of a tertiary amine at elevated temperature in a suitable solvent such as ETOH, DMF and the like. In one embodiment, compound 27 is deprotected with a nucleophilic base in an appropriate solvent to give compound 28. In another embodiment, compound 27 is oxidized to give compound 29 which is then treated with nucleophilic base to liberate compound 30.

Alternatively, 2-methylthio compound 23 can be replaced with its 2-hydrogen analogue. Under similar reaction conditions described for Scheme 5, the corresponding diazepine compounds without 2-methylthio substituent can be obtained.

Scheme 6 below illustrates further modifications of the compounds prepared in Scheme 4.

Scheme 6
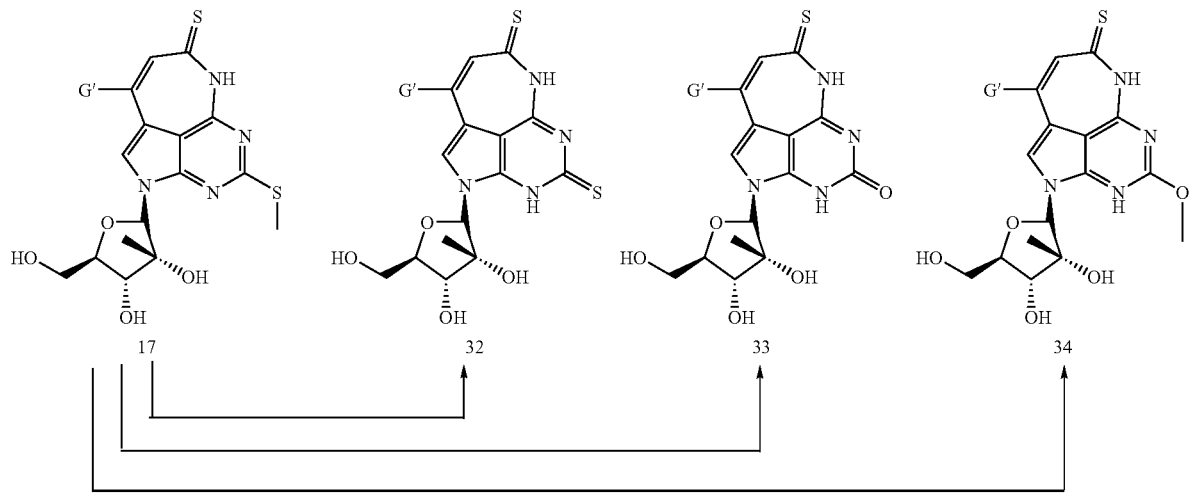
Scheme 6 follows the procedures of the synthetic methods described in Scheme 3 above to provide for compounds 32, 33, and 34.
Scheme 7 below illustrates the synthesis of additional diazepine compounds.
Scheme 7
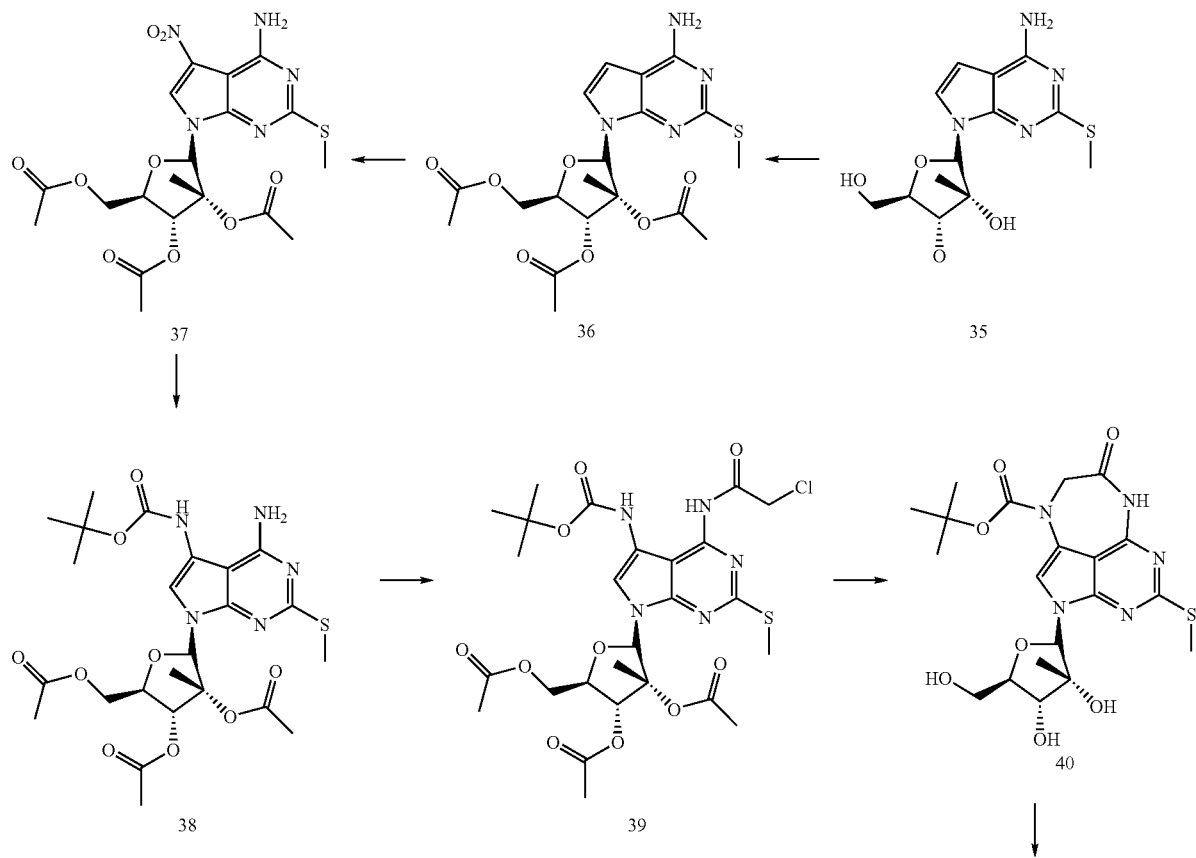

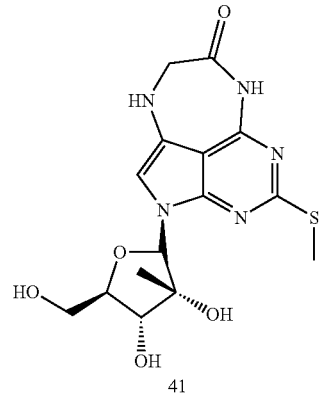

41

In Scheme 7, compound 35 is converted to the corresponding 2,3,5-tri-O-protected sugar, compound 36, by contact with acetyl chloride in acetic acid. In turn, compound 36 is converted to the 5-nitro derivative, compound 37, by contact with a mixture of nitric and sulfuric acid in a suitable solvent such as DCM. Hydrogenation in the presence of ditertbutyl-dicarbonate at elevated temperature in a suitable solvent such as EtOH, DMF and the like gives Compound 38. Contact of this compound with chloroacetyl chloride in the presence of DMAP in DMF, pyridine and the like gives compound 39. Base promoted cyclization of compound 39 gives compound 40 when the base is sufficiently nucleophilic. Acid cleavage of the boc protecting group yields compound 41.

Scheme 8 illustrates modification of the 2-methylthio group of some of the compounds described above and follows the procedure of Schemes 3.

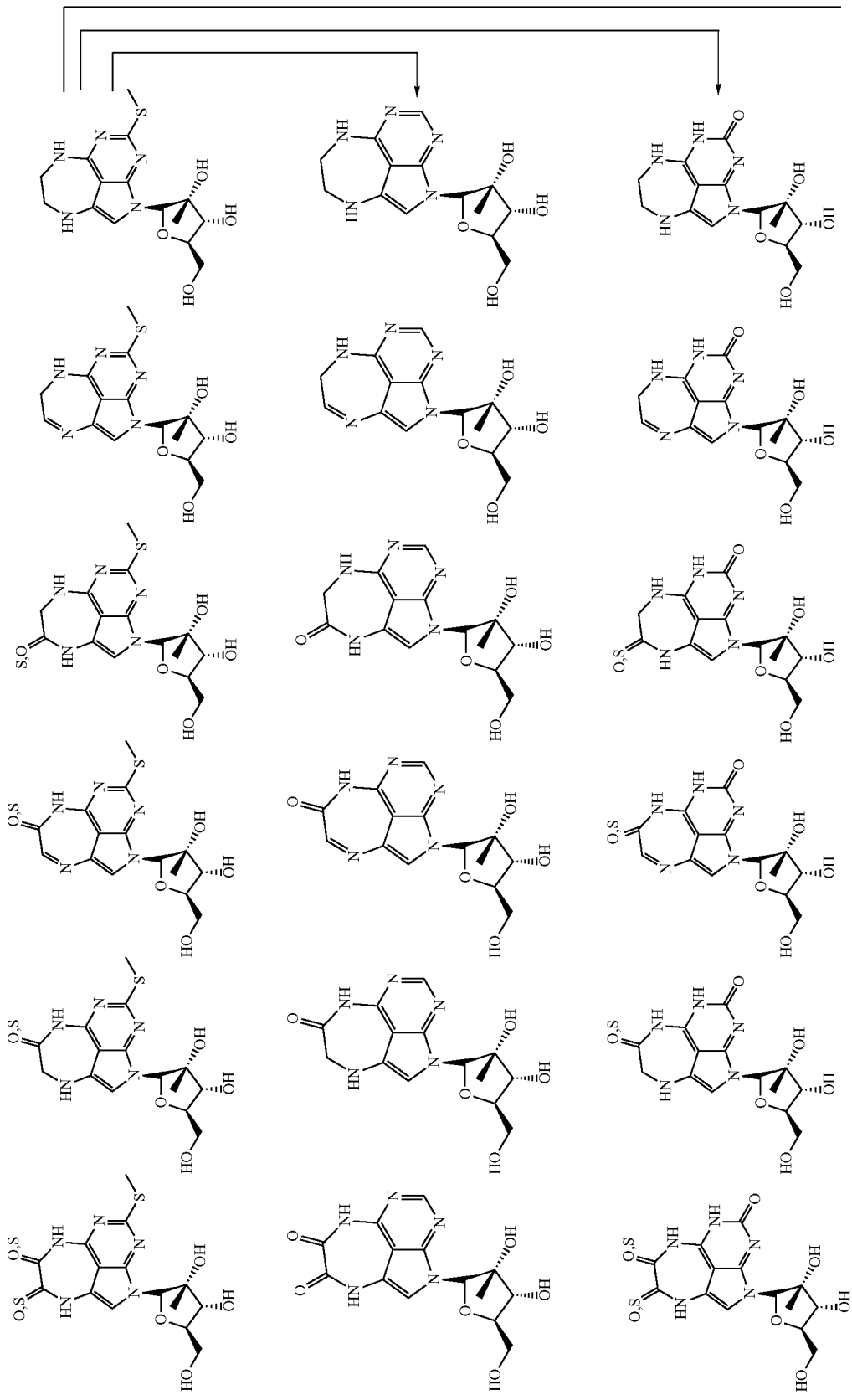

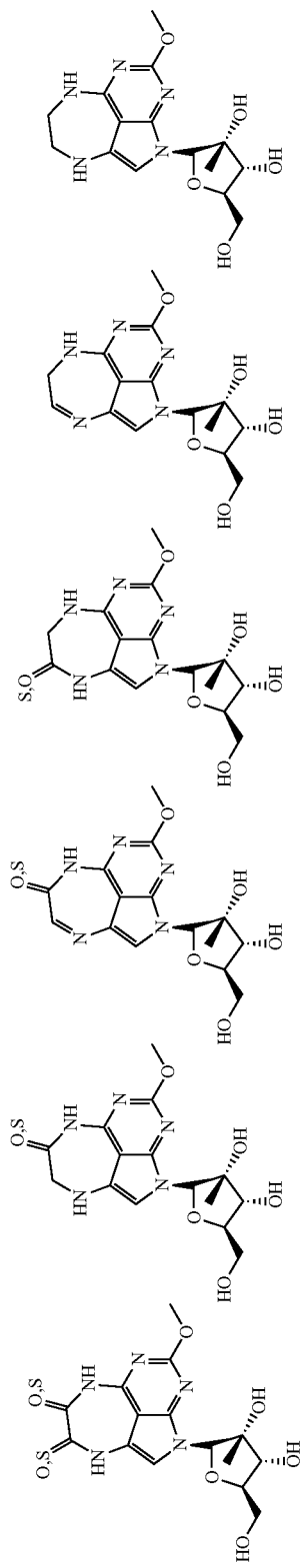

Examples of compounds which can be made by the procedures set forth above include the following:
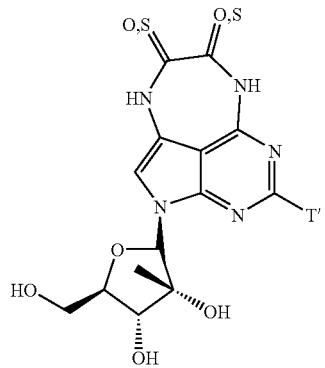
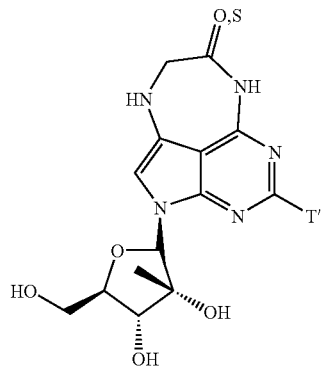
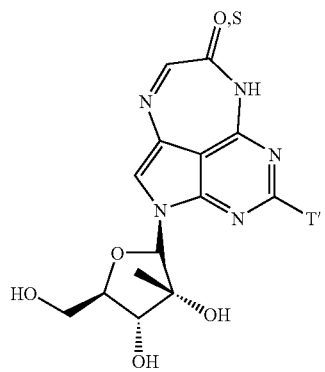
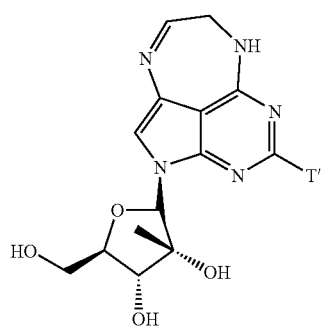
-continued
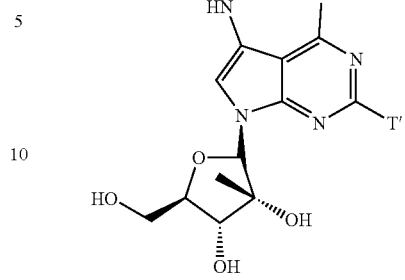
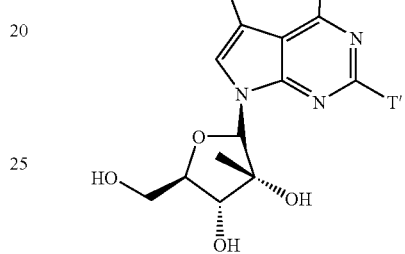
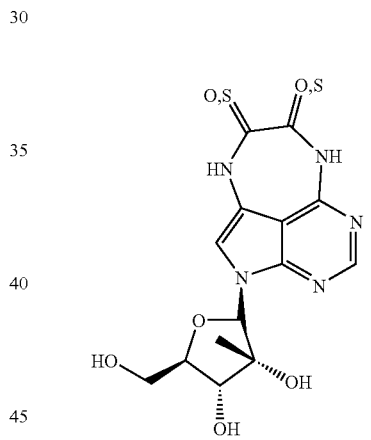
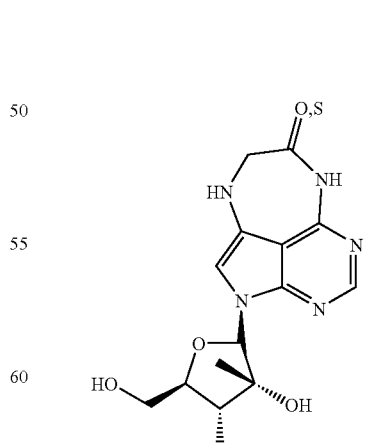

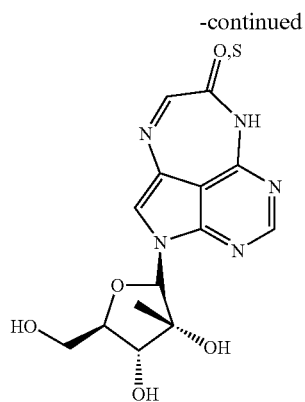
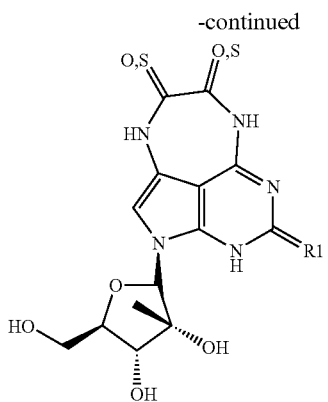
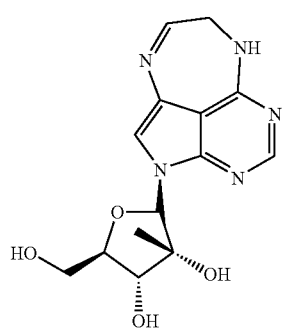
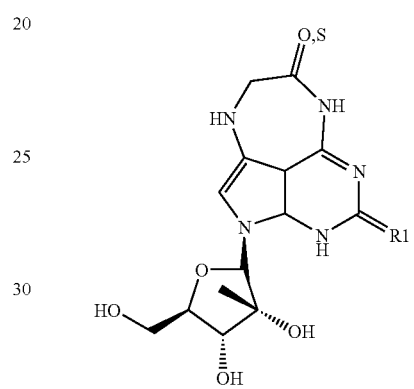
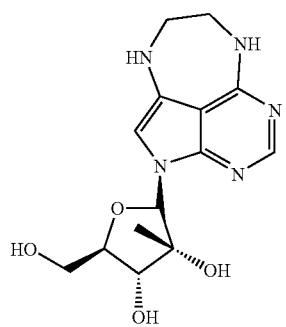
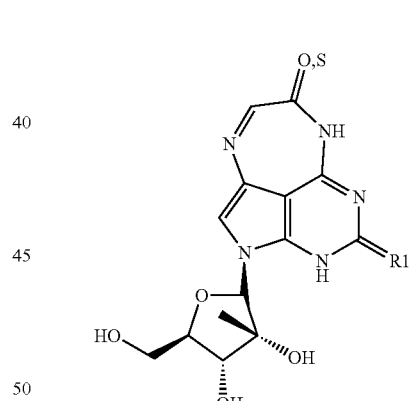
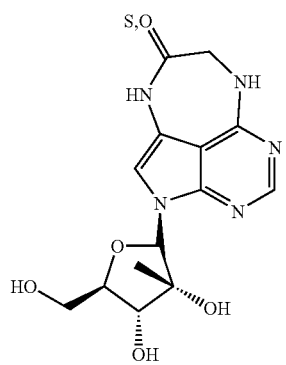
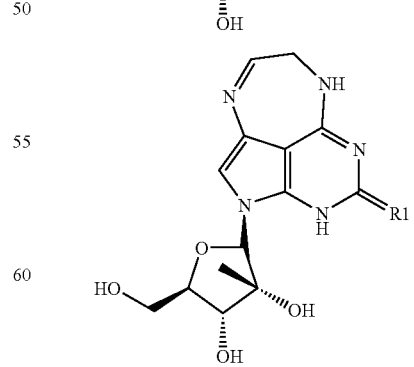

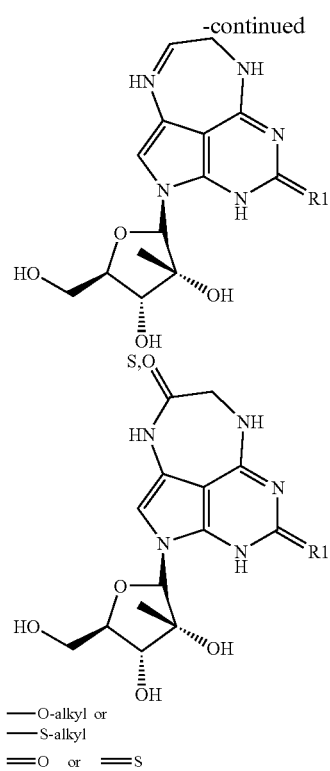

T' = —O-alkyl or
—S-alkyl

R1 = ═O or ═S

The following schemes illustrate methods for preparing the sugars used in the methods described above.

Formation of sugar a in Scheme 9 above where Ph is phenyl and X is a suitable leaving group such as halo, is accomplished as described by Mandal, S. B., et al., *Synth. Commun.*, 1993, 9, page 1239, starting from commercial D-ribose. Protection of the hydroxyl groups to form sugar b is described in Witty, D. R., et al., *Tet. Lett.*, 1990, 31, page 4787. Sugar c and d are prepared using the method of Ning, J. et al., *Carbohydr. Res.*, 2001, 330, page 165, and methods described herein. Sugar e is prepared by using a modification of the Grignard reaction with $CH_3MgBr$ or other appropriate organometallic as described herein (with no titanium/cerium needed). Finally the halogenated sugar (X=halo) used in the subsequent coupling reaction is prepared using the same protection method as used in to make sugar b above. The halogenation is described in Seela.[13]

Subsequently, any of the described nucleosides can be deprotected by methods well known to those skilled in the art, as taught by Greene et al. *Protective Groups in Organic Synthesis*, Jon Wiley and Sons, Second Edition, 1991.

An alternative approach to making protected sugars useful for coupling to heterocyclic bases is detailed in Scheme 10 below.

Scheme 10

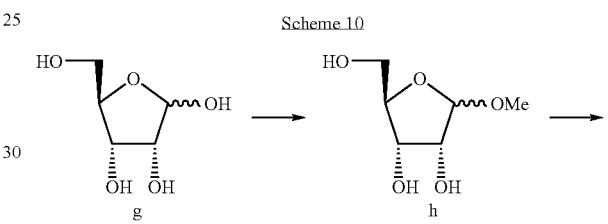

Scheme 9

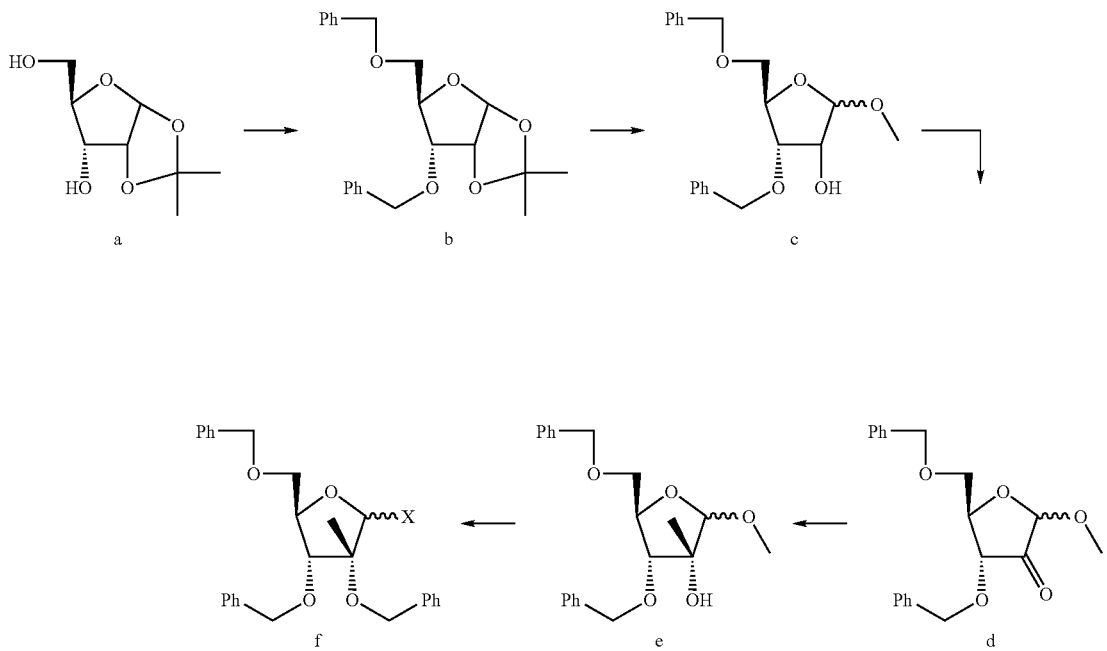

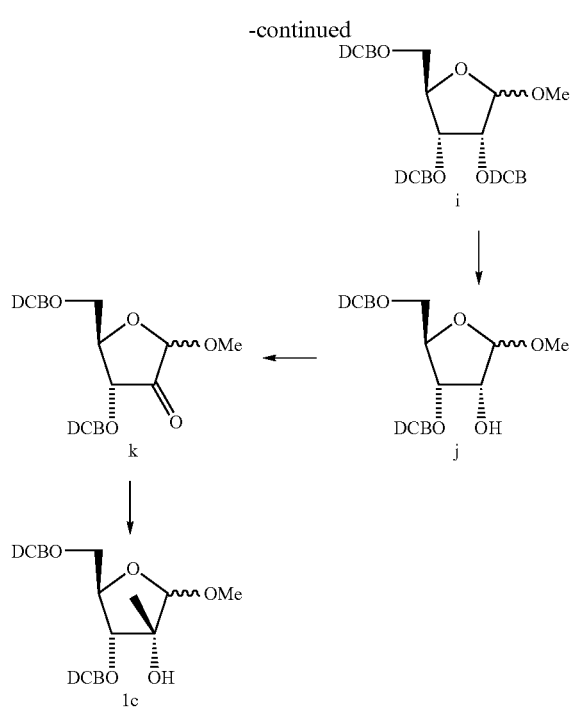

In Scheme 10, methylation of the hydroxyl group of compound g proceeds via conventional methodology to provide for compound h. The 2, 3 and 5 hydroxyl groups of the compound h are each protected with 2,4-dichlorobenzyl groups to provide for compound i. Selective deprotection of the 2-(2',4'-dichlorobenzyl) group on compound i proceeds via contact with stannous chloride in a suitable solvent such as methylene chloride, chloroform, and the like at reduced temperatures, e.g., ~0 to 5° C., until reaction completion, e.g., 24-72 hours, to provide for compound j. Oxidation of the 2-hydroxyl group of compound j proceeds as described herein to provide for compound k. Methylation also proceeds as described herein to provide for compound 1c.

In an alternative approach, an appropriately substituted nucleoside with a 2'-OH and 2'-H can be used as the starting material. This nucleoside can be purchased or can be prepared by any known means including standard coupling techniques. The nucleoside can be optionally protected with suitable protecting groups, preferably with acyl, substituted alkyl or silyl groups, by methods well known to those skilled in the art, as taught by Greene et al. *Protective Groups in Organic Synthesis*, John Wiley and Sons, Second Edition, 1991.

The hydroxyl group at the 2' position of the sugar of an otherwise appropriately protected nucleoside can then be oxidized with the appropriate oxidizing agent in a compatible solvent at a suitable temperature to yield the 2'-modified (oxo) sugar. Possible oxidizing agents are, for example, Dess-Martin periodine reagent, $Ac_2O$+ DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$ ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Coupling of an organometallic carbon nucleophile, such as a Grignard reagent, an organolithium, lithium dialkylcopper or $CH_3SiMe_3$ in TBAF with the ketone with the appropriate non-protic solvent at a suitable temperature, yields the alkyl substituted nucleoside. Isolation of the appropriate isomer is conducted as needed.

Subsequently, the nucleoside can be deprotected by methods well known to those skilled in the art, as taught by Greene et al. *Protective Groups in Organic Synthesis*, John Wiley and Sons, Second Edition, 1991.

The present invention is also directed to compounds where X is halo, preferably fluoro. Preparation of these compounds is accomplished by forming the desired 2'-fluoro-2'methylribofuranosyl derivative which is subsequently coupled to the desired base. The details for preparing 2'-fluoro-2'methylribofuranosyl derivatives is given in International Patent application with publication number WO 2005 003147 at least on pages 73, and 76 to 79.

In one embodiment of the invention, the D-enantiomers are utilized. However, L-enantiomers are also contemplated to be useful herein. The L-enantiomers corresponding to the compounds of the invention can be prepared following the same foregoing general methods, beginning with the corresponding L-sugar or nucleoside as starting material. In a particular embodiment, the 2'-C-branched ribonucleoside is desired.

Preparation of compounds where W, $W^1$ or $W^2$ is other than hydrogen, using the compounds prepared above as the starting materials, can be accomplished using the methods described in the following reviews of prodrug preparation:

1) Cooperwood, J. S. et al., "Nucleoside and Nucleotide prodrugs," in Ed(s) Chu, C. K. Recent Advances in Nucleosides (2002), 92-147.
2) Zemlicka, J. et al., Biochimica et Biophysica Acta (2002), 158(2-3), 276-286.
3) Wagner, C. et al., Medicinal Research Reviews (2002), 20(6), 417-451.
4) Meier, C. et al., Synlett (1998), (3), 233-242.

For example, conversion of the 5'-hydroxyl group can prepared using the methods describe in D. W. Hutchinson, (Ed. Leroy B. Townsend) "The Synthesis, reaction and Properties of Nucleoside Mono-, Di-, and Triphosphates, and Nucleosides with Changes in the Phosphoryl Residue, "Chemistry of Nucleosides and Nucleotides, Plenum Press, (1991) 2.

The foregoing, in connection with the following representative examples, further illustrate the various aspects of the invention.

EXAMPLES

The examples below as well as throughout the application, the following abbreviations have the following meanings. If not defined, the terms have their generally accepted meanings.

| | |
|---|---|
| $Ac_2O$ = | acetic anhydride |
| ACN = | acetonitrile |
| atm = | atmospheres |
| bs = | Broad singlet |
| CAN = | ceric ammonium nitrate |
| cm = | Centimeter |
| d = | doublet |
| dd = | Doublet of doublets |
| DCC = | Dicyclohexylcarbodiimide |
| DCM = | dichloromethane |

| | |
|---|---|
| DMEM = | Delbecco's minimum eagles medium |
| DMAP = | dimethylaminopyridine |
| DMF = | dimethylformamide |
| DMSO = | Dimethylsulfoxide |
| DTT = | Dithiothreitol |
| EDTA = | ethylene diamine tetraacetic acid |
| g = | Gram |
| HCV = | hepatitis C virus |
| Hz = | hertz |
| IPTG = | Isopropyl β-D-1-thiogalactopyranoside |
| IU = | international units |
| m = | Multiplet |
| MCPBA = | meta-chloroperbenzoic acid |
| min = | minute |
| M = | Molar |
| mg = | Milligram |
| mL = | Milliliter |
| mM = | Millimolar |
| mmol = | Millimole |
| MS = | mass spectrum |
| m/z = | Mass to charge ratio |
| ng = | Nanograms |
| nm = | Nanometers |
| nM = | Nanomolar |
| N = | Normal |
| NMR = | nuclear magnetic resonance |
| NTP = | nucleoside triphosphate |
| HATU = | O-(7-Azabenzotriazol-1-yl)-1,1,3,3-tetramethyluronium hexafluorophosphate |
| RP-HPLC = | reverse phase high performance liquid chromatography |
| HPLC = | high performance liquid chromatography |
| Lawesson reagent = | 2,4-Bis-(4-methoxyphenyl)-1,3-dithia-2,4-diphosphetane 2,4-disulfide |
| LC/MS = | liquid chromatography mass spectroscopy |
| s = | Singlet |
| t = | triplet |
| TBAF = | Tetrabutylammonium fluoride |
| TEA = | Triethylamine |
| TFA = | trifluoroacetic acid |
| THF = | Tetrahydrofuran |
| TLC = | thin layer chromatography |
| $T_m$ = | Melting temperature |
| TMS = | trimethylsilyl |
| UTP = | uridine triphosphate |
| μL = | Microliters |
| μg = | Micrograms |
| μM = | Micromolar |
| v/v = | volume to volume |
| wt % = | weight percent |

In addition, all reaction temperatures are in degrees Celsius unless reported otherwise.

In the examples below as well as elsewhere throughout this application, the claimed compounds employ the following numbering system:

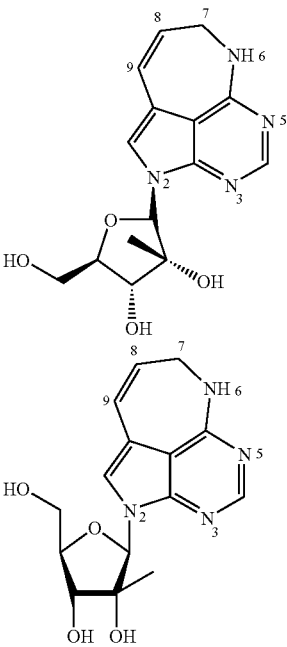

Throughout the application, the stereochemistry of the sugar can also be represented in the equivalent Haworth projection. For example, the above compound on the left is depicted as its Haworth projection on the right.

Example 1

Preparation of 2-(2'-methyl-β-D-ribofuranosyl)-2,6-dihydro-2,3,5,6-tetraaza-benzo[cd]azulen-7-one (Compound 301)

Step 1:

4-Chloro-7H-pyrrolo[2,3-d]pyrimidine 10.75 g (70 mmol) and N-iodosuccinimide (16.8 g, 75 mmol) were dissolved in 400 mL of dry DMF and left at ambient temperature in the darkness over night. The solvent was evaporated. The yellow residue was suspended in hot 10% solution of $Na_2SO_3$, filtered, washed twice with hot water and crystallized from ethanol to yield 14.6 g (74.6%) of the title compound as off-white crystals. The mother liquid was evaporated up to ⅓ volume and crystallized again from ethanol to give 2.47 g (12.3%) of the target compound. The total yield is close to 100%;

$T_m$ 212-214° C. (dec); UV $\lambda_{max}$: 307, 266, 230, 227 nm (methanol); MS: 277.93 (M–H); 313 (M+Cl); $^1$H-NMR (DMSO-$d_6$): 12.94 (s, 1H, NH), 8.58 (s, 1H), 7.94 (s, 1H).

Step 2:

The base, obtained as described above (11.2 g, 40 mmol) was suspended in 500 mL of $CH_3CN$, NaH was added (1.6 g, 40 mmol 60% in oil) and the reaction mixture was stirred at room temperature until NaH was dissolved (about 2 hour). 1-O-Methyl-2-methyl-3,5-bis-O-(2,4-dichlorobenzyl)-β-D-ribofuranose (10 g, 20 mmol) was dissolved in 500 mL of DCM and cooled down to 4° C. in ice/water bath. $HBr_{(g)}$ was bubbled through the solution for about 30 min. The reaction was monitored by TLC and run until the disappearance of the starting sugar (ether/hexane 1:9 v/v). Upon reaction completion, the solvent was evaporated at the temperature not higher that 20° C. and kept for 20 min in deep vacuum to remove the traces of HBr. Solution of Na-salt of the base was fast filtrated and the filtrate was added to the sugar component. The reaction was kept overnight at ambient temperature, neutralized with 0.1 N $H_2SO_4$ and evaporated. The residue was distributed between 700 mL of ethyl acetate and 700 mL of water. Organic fraction was washed with water (150 mL), brine (150 mL), dried over $Na_2SO_4$ and evaporated to give semi crystalline mixture. Toluene (500 mL) was added to form light tan precipitate of nonreacted heterocyclic base 2.5 g (25%). Filtrate was concentrated up to the volume of 50 mL and loaded on the glass filter with silica gel (10×10 cm). The filter was washed with 10% ethyl acetate in toluene collecting 500 mL fractions. Fraction 2-4 contained the target compound; fractions 6-7 contained the heterocyclic base.

Fractions 2-4 were evaporated, ether was added to the colorless oil and the mixture was sonicated for 5 min. The off-white precipitate was formed, yield 7.4 g (50%), mother liquid was evaporated and the described procedure was repeated to yield 0.7 g more of the target nucleoside. Total yield is 8.1 g (54.4%);

$T_m$: 67-70° C.; $^1$H-NMR (DMSO-$d_6$): δ 8.66 (s, 1H), 8.07 (s, 1H), 7.62-7.34 (m, 6H), 6.22 (s, 1H), 5.64 (s, 1H), 4.78-4.55 (m, 4H), 4.20 (s, 2H), 3.97-3.93 (dd, 1H) and 3.78-3.75 (dd, 1H), 0.92 (s, 3H); MS: 743.99 (M+H); Recovered base (total): 4 g as off-white crystals; $T_m$ 228-230° C.

Step 3:

To the solution of the compound from the previous step (8 g, 10.7 mmol) in DCM (200 mL) at −78° C. was added boron trichloride (1M in DCM, 88 mL, 88 mmol) dropwise. The mixture was stirred at −78° C. for 2.5 hours and additionally overnight at −20° C. The reaction was quenched by addition of MeOH/DCM (90 mL, 1:1) and the resulting mixture stirred at −20° C. for 30 min, then neutralized by aqueous ammonia at the same temperature. The solid was filtered and washed with methanol/DCM (250 mL, 1:1). The filtrates were combined with 50 mL of silica gel and evaporated up to dryness. Dry silica was loaded on the glass filter with silica gel (10×10 cm). The filter was washed with ethyl acetate collecting 500 mL fractions. Fraction 2-4 contained the target compound. The solvent was evaporated and the residue crystallized from acetone/hexane to give 3.3 g (72%) of the target nucleoside;

$^1$H-NMR (DMSO-$d_6$): δ 8.84 (s, 1H), 8.20 (s, 1H), 6.21 (s, 1H), 4.00-3.60 (m, 4H), 0.84 (s, 3H); MS: 426.26 (M+H); $T_m$:182-185° C.

Step 4:

The nucleoside (1.5 g, 3.5 mmol) prepared above was treated with liquid ammonia at 85° C. for 24 hours in the metal pressure reactor. After evaporation of ammonia the residue was dissolved in methanol and co-evaporated with silica gel (about 20 mL). Silica gel bearing the product was on the column (5×10 cm) with silica gel in acetone collecting 50 mL fractions. Fractions 2-8 contained the desired compound. Acetone was evaporated and the residue crystallized from methanol/acetonitrile to give 1.2 g (84%) of the target nucleoside;

$T_m$ 220-222° C. (dec); $^1$H-NMR (DMSO-$d_6$): δ 8.20 (s, 1H), 7.80 (s, 1H), 6.80-6.50 (bs, 1H), 6.09 (s, 1H), 5.19 (t, 1H), 5.13-5.11 (m, 2H), 4.00-3.70 (m, 3H), 3.60-3.20 (m, 1H), 0.84 (s, 3H); MS 407.32 (M+H).

Step 5:

To a solution of the product from Example 1, Step 4 (500 mg, 1.232 mmol) was added CuI (46.8 mg, 0.246 mmol), TEA (0.343 mL, 2.464 mmol) and 35 mL of DMF. The mixture was degassed with argon under sonication for 2-3 minutes and Pd(PPh$_3$)$_4$ (142 mg, 0.123 mmol) was added and the reaction mixture was heated to 55° C. for 20 min. Following the 20 min, ethyl propiolate (0.5 mL, 4.9 mL) was added to the reaction mixture every 20 minutes until all the starting material had been consumed, as was monitored by LC/MS. The crude reaction mixture was concentrated and purified on silica gel with methanol/methylene chloride (1:20) as the eluent to afford 600 mg of the target compound.

$^1$H NMR (CD$_3$OD): δ 0.858 (s, 3H), 1.34 (t, 3H), 3.87-4.126 (m, 4H), 4.28 (q, 2H), 6.24 (s, 1H), 8.17 (s, 1H), 8.24 (s, 1H); MS (M+1): 377.1.

Step 6:

To a solution of the product from Example 1, Step 5 (35 mg, 0.093 mmol) in 20 mL ethanol was added 10% palladium on carbon (20 mg). The reaction vessel was flushed with H$_2$ gas and held at 1 atm of H$_2$ via balloon until all starting material had been consumed, as was determined by TLC (24 hours). The palladium catalyst was filtered and the filtrate was concentrated and used directly in Example 1, Step 7.

Step 7:

To the crude material from Example 1, Step 6 (35 mg, 0.093 mmol) was added 0.1M NaOEt (20 mL) and the reaction heated to reflux for 1 hour. The reaction was neutralized with acetic acid, concentrated in vacuo and purified on Phenomenex-C$^{18}$ reverse phase HPLC with a 0-60% B gradient over 20 min at 10 mL/min (Buffer A=H$_2$O, Buffer B=acetonitrile);

$^1$H NMR (CD$_3$OD): δ 0.881 (s, 3H), 3.59-4.085 (m, 4H), 5.73 (d, 1H, J=11.4) 6.22 (s, 1H), 7.03 (d, 1H, J=11.4), 7.84 (s, 1H), 8.31 (s, 1H); MS (M+1): 333.1.

Example 2

Preparation of 2-(2'-methyl-β-D-ribofuranosyl)-2,6,8,9-tetrahydro-2,3,5,6-tetraaza-benzo[cd]azulen-7-one (Compound 302)

To a solution of the title product from Example 1 (10 mg, 0.030 mmol) in ethanol (20 mL) was added 1-2 mg PtO$_2$. The reaction vessel was flushed with H$_2$ gas and held at 1 atm of H$_2$ via balloon for 24 hours. The platinum catalyst was filtered and the filtrate was concentrated and the crude product was purified on silica gel methanol/methylene chloride (1:20) as the eluent to afford 4.0 mg of the title compound;

$^1$H NMR (CD$_3$OD): δ 0.852 (s, 3H), 2.91-3.03 (m, 4H), 3.61-4.14 (m, 4H), 6.22 (s, 1H), 7.53 (s, 1H), 8.44 (s, 1H); MS (M+1): 335.1.

Example 3

Preparation of 2-(2'-methyl-β-D-ribofuranosyl)-6,7-dihydro-2H-2,3,5,6-tetraaza-benzo[cd]azulene (Compound 303)

Step 1:

To a solution of the product from Example 1, Step 4 (200 mg, 0.492 mmol) was added CuI (36.5 mg, 0.192 mmol), TEA (0.064 mL, 0.46 mmol), 3.2 mL of DMF, and 9.6 mL of THF. The mixture was degassed with argon under sonication for 2-3 minutes and Pd(PPh$_3$)$_4$ (56 mg, 0.048 mmol) and 0.4 mL (2.83 mmol) propyne diethylacetal were added to the reaction mixture which was allowed to stir at room temperature overnight. The following morning an additional 0.4 mL of propyne diethylacetal was added and the reaction was stirred at room temperature for an additional 24 hours. The crude reaction mixture was concentrated and purified on silica gel methanol/methylene chloride (1:4) as the eluent to afford 200 mg of the target compound;

$^1$H NMR (CD$_3$OD): δ 0.84 (s, 3H), 1.25 (t, 6H), 3.66-4.15 (m, 8H), 6.22 (s, 1H), 7.90 (s, 1H), 8.12 (s, 1H); MS (M+1): 407.2.

Step 2:

To a solution of the product from Example 3, Step 1 (50 mg, 0.123 mmol) in 20 mL ACN/H$_2$O (1:1) was added Lindlar's catalyst (2-3 mg). The vessel was flushed with H$_2$ gas and held at 1 atm of H$_2$ via balloon. The reaction was allowed to stir at room temperature until all starting material was consumed, as determined by TLC. The catalyst was filtered and the filtrate was concentrated. The crude product was taken up in acetic acid (1 mL) and was stirred at room temperature for 15 min to liberate the aldehyde. This material was then concentrated in vacuo and MgSO$_4$ (160 mg, 1.33 mmol), NaCNBH$_3$ 1M in THF (0.025 mL, 0.025 mmol) were added and the mixture was heated to 55° C. for 15 min. The MgSO$_4$ was filtered and the filtrate concentrated and purified on Phenomenex-C$^{18}$ reverse phase HPLC with a 0-40% B gradient over 30 min at 10 mL/min (Buffer A=H$_2$O, Buffer B=acetonitrile) to yield the title compound;

$^1$H NMR (CD$_3$OD): δ 0.87 (s, 3H), 3.8-4.13 (m, 6H), 5.76 (dt, 1H, J=11.1 Hz, J=5.4 Hz) 6.20 (s, 1H), 6.66 (dt, 1H, J=11.1, J=1.2), 7.48 (s, 1H), 8.10 (s, 1H); MS (M+1): 319.15.

Example 4

Preparation of 2-(2'-methyl-β-D-ribofuranosyl)-6,9-dihydro-2H-2,3,5,6-tetraaza-benzo[cd]azulene (Compound 304)

To a solution of the product from Example 3, Step 1 (50 mg, 0.123 mmol) in ethanol (10 mL) was added PtO$_2$ (2-3 mg). The vessel was flushed with H$_2$ gas and held at 1 atm H$_2$ via balloon for 2 hours. The catalyst was filtered and the filtrate was concentrated and the product was purified on Phenomenex-C$^{18}$ reverse phase HPLC with a 0-80% B gradient over 30 min at 10 mL/min (Buffer A=H$_2$O, Buffer B=acetonitrile). The appropriate fractions were concentrated and taken up in 2 mL 70% TFA-water mixture and stirred at 0° C. for 20 min to liberate the aldehyde. The crude product was concentrated and was taken up in acetonitrile (30 mL) and heated to 55° C. for 2 hours. The reaction mixture was concentrated and purified on Phenomenex-C$^{18}$ reverse phase HPLC with a 0-60% B gradient over 30 min at 10 mL/min (Buffer A=H$_2$O, Buffer B=acetonitrile) to yield the title compound;

$^1$H NMR (DMSO-d$_6$): δ 0.68 (s, 3H), 3.48 (m, 2H), 3.63-3.97 (m, 4H), 4.79 (dt, 1H, J=10.8 Hz, J=4.5 Hz) 5.1 (s, 3H), 6.10 (m, 1H), 6.22 (s, 1H), 7.45 (s, 1H), 8.26 (s, 1H), 9.36 (d, 1H, J=6.3 Hz); MS (M+1): 319.15.

Example 5

Preparation of 2-(2'-methyl-β-D-ribofuranosyl)-6,7,8,9-tetrahydro-2H-2,3,5,6-tetraaza-benzo[cd]azulene (Compound 305)

Step 1:

N-trifluoroacetyl propargylamine was synthesized as described in Tetrahedron Lett. 1988, Vol. 29, No. 41 pp. 5221-5224.

Step 2:

To a solution of the product from Example 1, Step 3 (125 mg, 0.294 mmol) in DMF (1.7 mL) and THF (5 mL) was added CuI (4.4 mg, 0.0231 mmol) and TEA (0.25 mL, 1.46 mmol). The mixture was degassed with argon under sonication for 2-3 minutes followed by the addition of Pd(PPh$_3$)$_2$Cl$_2$ (4.4 mg, 0.00627 mmol) and 0.6 mL (6.86 mmol) of n-trifluoroacetyl propargylamine. The reaction was allowed to stir at room temperature overnight. The following day, the reaction mixture was concentrated and purified on Phenomenex-C$^{18}$ reverse phase HPLC with a 0-80% B gradient over 30 min at 10 mL/min (Buffer A=H$_2$O, Buffer B=acetonitrile) to afford 100 mg of the target compound;

MS (M+1): 449.09.

Step 3:

To a solution of the product from Example 5, Step 2 (30 mg, 0.0668) in THF (10 mL) was added 1-2 mg PtO$_2$. The vessel was flushed with H$_2$ gas and held at 1 atm of H$_2$ via balloon for 1 hour at room temperature. The catalyst was filtered and the filtrate was concentrated. The residue was taken up in concentrated ammonium (3 mL), stirred at room temperature for 1 hour, and concentrated. The residue was co-evaporated with pyridine (5 mL) 3 times followed by toluene (5 mL) 2 times and taken up in acetonitrile in the presence of molecular sieves. TEA (30 µl) was added and the reaction was heated to 75° C. for 3 hours. The molecular sieves were filtered and the filtrate was concentrated and purified on Phenomenex-C$^{18}$ reverse phase HPLC with a 0-40% B gradient over 30 min at 10 mL/min (Buffer A=H$_2$O, Buffer B=acetonitrile) to afford 8 mg of the title compound;

$^1$H NMR (CD$_3$OD): δ 0.83 (s, 3H), 2.02 (m, 2H), 2.89 (m, 2H), 3.50 (m, 2H), 3.80-4.1 (m, 4H), 6.19 (s, 1H), 7.23 (s, 1H), 8.0 (s, 1H); MS (M+1): 321.17.

Example 6

Preparation of 9-amino-2-(β-D-ribofuranosyl)-2,6-dihydro-7H-2,3,5,6-tetraazabenzo[cd]azulen-7-one (Compound 306)

Step 1. 2,3-O-isopropylidene-D-ribofuranose

Into a suspension of D-ribose (50 g, 0.33 mol) in acetone (1500 mL) was added sulfuric acid (1 mL) dropwise. Reaction mixture was stirred overnight at room temperature and then neutralized with sat. aq. NaHCO$_3$. Solution was decanted and concentrated. Oily residue was dissolved in EtOAc (1000 mL) and washed with water (300 mL). Aqueous layer was re-extracted with EtOAc (2×500 mL). Combined extracts were dried over Na$_2$SO$_4$ and concentrated to yield the target compound (42.3 g, 67.3%) as oil which was used as such for the next step.

Step 2. 5-O-tert-Butyldimethylsily-2,3-O-isopropylidene-D-ribofuranose 2,3-O-isopropylidene-D-ribofuranose, obtained as described above (21.7 g, 0.114 mol) was dissolved in anhydrous CH$_2$Cl$_2$ (600 mL) and imidazole (15.53 g, 0.228 mol) and TBDMSCl (18.90 g, 0.125 mol) were added under argon. After stirring for 3 h at room temperature reaction mixture was neutralized with 1N aq. HCl. Two layers were separated. Organic layer was washed with water and saturated brine, dried (Na$_2$SO$_4$) and evaporated. Residue was purified on silica gel column with hexanes/EtOAc (11/1, 1800 mL; 10/1, 1540 mL; 8/1, 1800 mL) as the eluents to yield 23.89 g (69%)

of the target compound (as mixture of α/β isomers 88/12) as a thick oil (which slowly crystallized in the freezer).

$^1$H NMR (DMSO-d$_6$): δ 6.39 (d, 1H, J=4.4 Hz), 5.11 (d, 1H, J=4.4 Hz), 4.56 (d, 1H, J=6.2 Hz), 4.39 (d, 1H, J=6.7 Hz), 3.89 (t, 1H, J=6.7 Hz), 3.52 (m, 2H), 1.31 (s, 3H), 1.19 (s, 3H), 0.82 (s, 9H), 0.00 (s, 6H).

Step 3. 7-(5'-O-tert-Butyldimethylsily-2',3'-O-isopropylidene-D-ribofuranosyl)-4-chloro-5-iodo-7H-pyrrolo[2,3-d]pyrimidine 4-Chloro-5-iodo-7H-pyrrolo[2,3-d]pyrimidine, obtained as described in Example 1, Step 1 (14.80 g, 53 mmol) was suspended in anhydrous CH$_3$CN (500 mL). NaH (2.12 g, 53 mmol 60% in oil) was added then and the reaction mixture was stirred at room temperature for 2 h. 5-O-tert-Butyldimethylsily-2,3-O-isopropylidene-D-ribofuranose (15.22 g, 50 mmol), obtained as described in Step 2 was dissolved in anhydrous THF (100 mL), CCl4 (6.27 mL, 65 mmol) was added and the resulting mixture cooled down to −78° C. At this point HMPT (9.54 mL, 62.5 mmol) was added dropwise. Reaction mixture was allowed to warm slowly (in 0.5 h) to −30° C. and stirred at −30° C. to −20° C. for 1 h and then transferred via canula into the solution of Na-salt of the base. The combined mixture was stirred overnight at room temperature, then filtered and filtrate evaporated. The residue was purified on silica gel with hexanes/EtOAc (15/1) as the eluent to yield the target compound as off-white crisp foam (8.49 g, 30%).

$^1$H NMR (DMSO-d$_6$): δ 8.66 (s, 1H), 8.05 (s, 1H), 6.31 (d, 1H, J=2.6 Hz), 5.16 (dd, 1H, J=6.2, 2.3 Hz), 4.88 (dd, 1H, J=6.2, 2.9 Hz), 4.23 (m, 1H), 3.76 (dd, 2H, J=11.4, 4.1 Hz), 3.67 (dd, 1H, J=11.3, 4.8 Hz), 1.52 (s, 3H), 1.30 (s, 3H), 0.81 (s, 9H), 0.00 (s, 6H).

Step 4. 4-chloro-5-iodo-7-(β-D-ribofuranosyl)-7H-pyrrolo[2,3-d]pyrimidine

To the mixture of the compound from the previous step (5.5 g, 9.7 mmol) in methanol (250 mL) was added Dowex H$_+$ (~20 mL; previously washed with Me.OH). The mixture was stirred at room temperature for 3 h. The resin was filtered and washed with methanol (500 mL). The combined filtrates were evaporated and solid residue treated with MeOH (100 mL) to yield after filtration 2.88 g (72%) of the target compound.

$^1$H NMR (DMSO-d$_6$): δ 8.65 (s, 1H), 8.23 (s, 1H), 6.18 (d, 1H, J=6.2 Hz), 5.43 (br, 1H), 5.0-5.3 (br, 2H), 4.36 (m, 1H), 4.08 (dd, 1H, J=5.0, 3.2 Hz), 3.92 (m, 1H), 3.64 (dd, 1H, J=12.0, 3.8 Hz), 3.55 (dd, 1H, J=11.9, 3.7 Hz).

Step 5. 4-amino-5-iodo-7-(β-D-ribofuranosyl)-7H-pyrrolo[2,3-d]pyrimidine

The nucleoside prepared as described above (155 mg, 0.38 mmol) was treated with liquid ammonia at 120° C. for 20 hours in the high pressure metal reactor. After evaporation of ammonia the residue was purified on silica gel with CH$_2$Cl$_2$/MeOH (30/1, 20/1, 15/1) as the eluents to yield the target compound as white powder (115 mg, 79%).

$^1$H NMR (Acetone-d$_6$): δ 8.10 (s, 1H), 7.59 (s, 1H), 6.37 (br s, 2H), 5.98 (d, 1H, J=6.5 Hz), 5.29 (br, 1H), 4.76 (m, 1H), 4.62 (br, 1H), 4.33 (br, 1H), 4.11 (m, 1H), 3.74 (m, 1H).

Step 6. [4-amino-7-(β-D-ribofuranosyl)-7H-pyrrolo[2,3-d]pyrimidin-5-yl]-propynoic acid ethyl ester To a solution of the product from Step 5 (61 mg, 0.156 mmol) in DMF (2 mL) were added CuI (6 mg, 0.032 mmol) and TEA (45 μL, 0.323 mmol). The mixture was degassed with argon under sonication for 2-3 minutes and Pd(PPh$_3$)$_4$ (18 mg, 0.016 mmol) was added and the resulting mixture was heated at 55° C. for 15 min. Ethyl propiolate (4×5 μL, 0.197 mmol) was added to the reaction mixture at 55° C. in 30 minutes intervals. The crude mixture was concentrated and purified on silica gel with CH$_2$Cl$_2$/MeOH (100/1, 50/1, 25/1) as the eluents to afford 36 mg (64%) of the target compound.

$^1$H NMR (Acetone-d$_6$): δ 8.18 (s, 1H), 8.06 (s, 1H), 6.4 (br, 2H), 6.05 (d, 1H, J=6.2 Hz), 5.27 (br, 1H), 4.77 (m, 1H), 4.38 (m, 1H), 4.27 (q, 2H, J=7.1 Hz), 4.15 (m, 1H), 3.79 (m, 2H), 1.32 (t, 3H, J=7.0 Hz). MS: m/z=363.7 (M+1).

Step 7. [4-amino-7-(β-D-ribofuranosyl)-7H-pyrrolo[2,3-d]pyrimidin-5-yl]-acrylic acid ethyl ester The nucleoside, prepared as described above (36 mg, 0.1 mmol) was treated with liquid ammonia at 75° C. for 1.5 h in the high pressure metal reactor. After evaporation of ammonia the residue was purified on a silica gel column with CH$_2$Cl$_2$/MeOH (40/1, 20/1, 10/1) as the eluents to yield 15 mg (40%) of the target compound.

$^1$H NMR (CD$_3$OD): δ 8.12 (s, 1H), 7.70 (s, 1H), 6.06 (d,1H, J=6.2 Hz), 4.86 (s, 1H), 4.60 (m, 1H), 4.28 (q, 2H, J=7.1 Hz), 4.11 (m, 1), 3.86 (dd, 1H, J=12.3, 2.6 Hz), 3.74 (dd, 1H, J=12.3, 2.9 Hz), 1.27 (t, 3H, J=7.2 Hz). MS: m/z=380.7 (M+1).

Step 8. 9-amino-2-(β-D-ribofuranosyl)-2,6-dihydro-7H-2,3,5,6-tetraazabenzo[cd]-azulen-7-one (Compound 306)

A solution of the compound from Step 7 (10 mg, 0.026 mmol) in 0.1M NaOMe (3 mL) was heated at reflux temperature for 2 hour then concentrated in vacuo and purified on Phenomenex-C$^{18}$ reverse phase HPLC with a 0-40% B gradient over 30 min at 10 mL/min (Solvent A=H$_2$O, Solvent B=MeCN). The title compound was isolated as a white solid in 4 mg (46%) yield.

$^1$H NMR (CD$_3$OD+D$_2$O): δ 8.31 (s, 1H), 7.91 (s, 1H), 6.15 (d, 1H, J=6.5 Hz) 5.14 (s, 1H), 4.64 (m, 1H), 4.35 (dd, 1H, J=5.3, 3.2 Hz), 4.24 (m, 1H), 3.86 (m, 1H); MS: m/z=334.1 (M+1).

Example 7

Preparation of 2-(2'-methyl-β-D-ribofuranosyl)-9-methylamino-2,6-dihydro-2,3,5,6-tetraaza-benzo[cd]azulen-7-one (Compound 307)

The product from Example 1, Step 5 (225 mg, 0.598 mmol) in methylamine (9 mL, 1 M in THF) was sealed in an autoclave bomb and heated to 80° C. for 1 hour. The reaction mixture was concentrated and the residue was taken up in 11.6 mL of 0.5 M NaOEt and heated to 80° C. for 1 hour. The reaction mixture was concentrated and purified on Phenomenex-C$^{18}$ reverse phase HPLC with a 0-40% B gradient over 20 min at 10 mL/min (Buffer A=H$_2$O, Buffer B=acetonitrile) to afford 110 mg of the title compound;

$^1$H NMR (DMSO-d$_6$): δ 0.76 (s, 3H), 2.82 (d, 3H, J=4.2) 3.72-3.98 (m, 4H), 4.81 (d, 1H), 4.88 (t, 1H) 5.24 (d, 1H,

J=8.1), 5.25(s, 1H), 6.20 (s, 1H), 7.08 (d, 1H, J=4.8), 7.80 (s, 1H), 8.32 (s, 1H), 10.16 (s, 1H); MS (M+1): 362.15.

Example 8

Preparation of 2-(2'-methyl-β-D-ribofuranosyl)-2,6, 7,9-tetrahydro-2,3,5,6,9-pentaaza-benzo[cd]azulen-8-one (Compound 308)

Step 1. 4-Chloro-7-(2'-methyl-β-D-ribofuranosyl)-7H-pyrrolo[2,3-d]pyrimidine

The target compound was synthesized according to the procedure in U.S. Pat. No. 6,777,395.

Step 2. 4-Chloro-7-(2'-methyl-2',3',5'-tris-O-acetyl-β-D-ribofuranosyl)-7H-pyrrolo[2,3-d]pyrimidine To a solution of the product from Step 1 (1.0 g, 3.34 mmol) in glacial acetic acid (14 mL) was added acetyl chloride (4 mL) and the mixture was stirred at room temperature overnight. The reaction was then concentrated in vacuo, co-evaporated with toluene, and purified by Isco CombiFlash purification system with a 40 g silica gel column and 0-35% MeOH gradient in DCM over 30 minutes to afford 1.4 g (99%).

MS (M+1): 471.0

Step 3. 4-Chloro-7-(2'-methyl-2',3',5'-tris-O-acetyl-β-D-ribofuranosyl)-5-nitro-7H-pyrrolo[2,3-d]pyrimidine A solution of the product from Step 2 (700 mg, 1.64 mmol) in DCM was cooled to 0° C. in ice/water bath. Meanwhile fuming $HNO_3$ (1 mL) and $H_2SO_4$ (1 mL) were premixed and added dropwise to a vigorously stirred DCM solution containing the protected nucleoside and the mixture. The solution was stirred at 0° C. for 1.5 hours then quenched by pouring into an ice cold saturated $Na_2CO_3$ solution (125 mL). The product was extracted with DCM and the organic layers were dried over $Na_2SO_4$ and concentrated in vacuo. The crude purified by Isco CombiFlash purification system with a 40 g silica gel column and 0-35% MeOH gradient in DCM over 30 minutes to afford 440 mg (52%).

$^1$H NMR (DMSO-$d_6$): δ 9.12 (s, 1H), 8.91 (s, 1H), 6.81 (s, 1H), 5.44 (m, 1H), 4.5-4.3 (m, 3H), 2.10 (m, 9H), 1.38 (s, 3H). MS (M+1): 471.0

Step 4. 4-(2-methoxy-2-oxoethylamino)-7-(2'-methyl-2',3',5'-tris-O-acetyl-β-D-ribofuranosyl)-5-nitro-7H-pyrrolo[2,3-d]pyrimidine The compound from Step 3 (150 mg, 0.319 mmol) was dissolved in anhydrous MeOH (3 mL). Meanwhile glycine methylester mono hydrochloride (48 mg, 0.383 mmol) was neutralized with a 0.5M solution NaOMe (766 µl, 0.383 mmol) and this mixture was added to the methanolic solution containing nucleoside and the mixture was heated to 75° C. for 1.5 hours. Concentrated reaction in vacuo and purified on flash silica gel chromatography with a 0-5.0% MeOH gradient in DCM to afford 100 mg (60%).

$^1$H NMR (DMSO-$d_6$): δ 8.74 (s, 1H), 8.35 (s, 1H), 8.14 (t, 1H, J=5.4 Hz), 6.68 (s, 1H), 5.47 (m, 1H), 4.5-4.3 (m, 5H), 3.68 (s, 3H), 2.10 (m, 9H), 1.37 (s, 3H). MS (M+1): 524.1

Step 5. 2-(2'-methyl-β-D-ribofuranosyl)-2,6,7,9-tetrahydro-2,3,5,6,9-pentaaza-benzo[cd]azulen-8-one (Compound 308)

To the compound from Step 4 (20 mg, 0.038 mmol) was added MeOH (5 mL), Pd (10% on Carbon), and TEA (0.5 mL) and the mixture was purged with $H_2$ gas for 5 minutes then heated to 50° C. overnight under 1 atmosphere of $H_2$ via balloon. The catalyst was then filtered and the mixture concentrated in vacuo. The crude product was purified on Phenomenex-$C^{18}$ reverse phase HPLC with a 0-50% B gradient over 20 min at 10 mL/min (Buffer A=$H_2O$, Buffer B=acetonitrile) to afford 8.5 mg (66%) of the title compound.

$^1$H NMR (DMSO-$d_6$): δ 10.27 (s, 1H), 8.1 (s, 1H), 7.51 (t, 1H, J=3.6 Hz), 7.03 (s, 1H), 6.10 (s, 1H), 5.13-5.03 (m, 3H), 3.94-3.74 (m, 5H), 3.64-3.54 (m, 1H), 0.71 (s, 3H). MS (M+1): 336.12

Example 9

Preparation of 9-acetamido-2-(2'-methyl-β-D-ribofuranosyl)-2,6-dihydro-2,3,5,6-tetraaza-benzo[cd]azulen-7-one (Compound 309)

Step 1. 9-Amino-2-[2'-methyl-3',5'-O-(1",1",3",3"-tetraisopropyl-disiloxane-1",3"-diyl)-β-D-ribofuranosyl]-2,6-dihydro-7H-2,3,5,6-tetraazabenzo[cd]azulen-7-one To the product from Example 14, (250 mg, 0.720 mmol) in DMF (6.4 mL) was added imidazole (293 mg, 4.30 mmol) followed by the dropwise addition of 1,3-dichloro-1,1,3,3-tetraisopropyldisiloxane (285 µl, 0.894 mmol) under rapid stirring. The mixture was stirred under argon for 4 hours then quenched with methanol (1 ml) and concentrated in vacuo. The crude material was purified by flash silica gel chromatography with a 0.1-5.0% MeOH gradient in DCM to afford 290 mg (68%) of the target compound.

$^1$H NMR (DMSO-$d_6$): δ 10.13 (1H, d, J=1.2 Hz), 8.29 (1H, s), 7.66 (1H, s), 6.64 (2H, br s), 6.07 (1H, s), 5.26 (s, 1H), 5.06 (d, 1H, J=1.8 Hz), 4.3-4.15 (m, 2H), 4.05-3.95 (m, 2H), 1.15-0.90 (m, 28H), 0.85 (s, 3H). MS (M+1): 590.3

Step 2. 9-Acetamido-2-[2'-methyl-3',5'-O-(1",1",3",3"-tetraisopropyl-disiloxane-1",3"-diyl)-β-D-ribofuranosyl]-2,6-dihydro-7H-2,3,5,6-tetraazabenzo[cd]azulen-7-one To the product from Step 1 (50 mg, 0.085 mmol) in pyridine (1 mL) was added DMAP (20.7 mg, 0.170 mmol), 10 molecular sieves, and acetic anhydride (401 µl, 0.424 mmol). The mixture was allowed to stir at ambient temperature overnight then concentrated in vacuo. The crude material was purified on Isco CombiFlash purification system with a 4 g silica gel column and 0.1-5.0% MeOH gradient in DCM over 30 minutes to afford 25 mg (47%) of the target compound.

$^1$H NMR (DMSO-$d_6$): δ 10.75 (d, 1H, J=1.5 Hz), 9.71 (s, 1H), 8.34 (s, 1H), 7.65 (s, 1H), 6.56 (d, 1H, J=1.5 Hz), 6.09 (s, 1H), 5.32 (s, 1H), 4.25-3.95 (m, 4H), 2.12 (s, 3H), 1.15-1.0 (m, 28H), 0.82 (s, 3H). MS (M+1): 632.2

Step 3. 9-Acetamido-2-(2'-methyl-β-D-ribofuranosyl)-2,6-dihydro-2,3,5,6-tetraaza-benzo[cd]azulen-7-one (Compound 309)

The product from Step 2 (25 mg, 0.040 mmol) in anhydrous THF (0.6 mL) was cooled in an ice/water bath to 0° C.

and a 1 Molar solution of TBAF in THF (158 μl, 0.158 mmol) was added dropwise to the rapidly stirred solution. The mixture was allowed to stir at 0° C. for 15 minutes then allowed to warm to room temperature over an additional 30 minutes. The crude reaction was concentrated in vacuo and purified on Phenomenex-C$^{18}$ reverse phase HPLC with a 0-40% B gradient over 30 min at 10 mL/min (Buffer A=H$_2$O, Buffer B=acetonitrile) to afford 5.0 mg (32%) of the title compound.

$^1$H NMR (DMSO-d$_6$): δ 10.70 (br s, 1H), 9.43 (s, 1H) 8.35 (s, 1H), 7.96 (s, 1H), 6.64 (s, 1H), 6.15 (s, 1H), 5.29 (br s, 1H), 5.18 (d, 1H, J=4.5 Hz), 4.99 (dd, 1H, J=5.1 Hz), 3.95-3.65 (m, 4H), 2.15 (s, 3H), 0.78 (s, 3H). MS (M+1): 390.1

Example 10

Preparation of 9-hydrazino-2-(2'-methyl-β-D-ribofuranosyl)-2,6-dihydro-2,3,5,6-tetraaza-benzo[cd]azulen-7-one (Compound 310)

To a solution of the product from Example 35 (17 mg, 0.0488 mmol) was treated with 1 mL of neat hydrazine at room temperature for overnight and checked by LC-MS. The reaction then was concentrated. The crude product was purified by HPLC to afford 10 mg of the title compound as a mixture of tautomers;

$^1$H NMR (DMSO-d$_6$, 300 MHz): δ 12.005 (s, 1H), 10.772 (s, 1H), 9.253 (s, 1H), 7.941 (s, 1H), 7.811 (s, 1H), 7.116 (s, 1H), 6.056 (s, 1H), 5.50 (d, 1H), 5.20 (m, 1H), 5.50 (d, 1H), 5.01 (d, 1H, J=9 Hz), 3.964-3.580 (m, 4H), 0.627 (s, 3H); MS (M+1): 363.1.

Example 11

Preparation of 9-fluoro-2-(2'-methyl-β-D-ribofuranosyl)-2,6-dihydro-2,3,5,6-tetraaza-benzo[cd]azulen-7-one (Compound 311)

To a solution of the product from Example 1, Step 5 (37 mg, 0.106 mmol) was added 2.5 g of tetrabutylammoniumdihydrogentrifluoride (50% solution in dichloroethane. The reaction was heated to 100° C. for 4 days and monitored by HPLC. The reaction mixture was then neutralized with ammonium hydroxide to pH=6. The product was isolated by reverse phase HPLC separation.

$^1$H NMR (DMSO-d$_6$): δ 10.976 (s, 1H), 8.417 (s, 1H), 8.269 (s, 1H), 6.111 (s, 1H), 5.727-5.652 (d, 1H, J=22.5 Hz) 4.00-3.68 (m, 4H), 0.74 (s, 3H); $^{19}$F NMR (DMSO-d$_6$): δ-101.89 (d, 1H, J=22.2 Hz); MS (M+1): 351.1.

Example 12

Preparation of 9-formamido-2-(2'-methyl-β-D-ribofuranosyl)-2,6-dihydro-2,3,5,6-tetraaza-benzo[cd]azulen-7-one (Compound 312)

Step 1. 9-Formamido-2-[2'-methyl-3',5'-O-(1",1",3",3"-tetraisopropyl-disiloxane-1",3"-diyl)-β-D-ribofuranosyl]-2,6-dihydro-7H-2,3,5,6-tetraazabenzo[cd]azulen-7-one To the compound from Example 9, Step 1 (100 mg, 0.170 mmol) was added DMAP (41.5 mg, 0.340 mmol) and a 1:1 (v/v) mixture of formic acid and acetic anhydride (1.6 mL). The mixture was allowed to stir at ambient temp for 15 minutes then cooled to 0° C. in an ice/water bath and quenched with TEA (1.5 mL). The mixture was then poured over ice water and the crude product extracted with DCM (50 mL, 2×). The organic layers were combined, dried over Na$_2$SO$_4$, and concentrated in vacuo. The crude material was purified on Isco CombiFlash purification system with a 4 g silica gel column and 0.1-5.0% MeOH gradient in DCM over 30 minutes to afford 47 mg (45%) of the target compound.

$^1$H NMR (DMSO-d$_6$): δ 11.53 (br s, 1H), 10.68 (br s, 1H), 10.08 (s, 1H), 8.23 (br s, 1H), 8.42 (s, 1H), 8.30 (s, 1H), 6.10 (s, 1H), 5.33 (s, 1H), 4.3-4.0 (m, 4H), 1.15-0.95 (m, 28H), 0.86 (s, 3H). MS (M+1): 618.3

Step 2. 9-Formamido-2-(2'-methyl-β-D-ribofuranosyl)-2,6-dihydro-2,3,5,6-tetraaza-benzo[cd]azulen-7-one (Compound 312)

The product from Step 1 (47 mg, 0.076 mmol) in anhydrous THF (1.2 mL) was cooled in an ice/water bath to 0° C. and a 1 Molar solution of TBAF in THF (190 μl, 0.190 mmol) was added dropwise to the rapidly stirred solution. The mixture was allowed to stir at 0° C. for 30 minutes. The crude reaction was concentrated in vacuo and purified on Phenomenex-C$^{18}$ reverse phase HPLC with a 0-40% B gradient over 30 min at 10 mL/min (Buffer A=H$_2$O, Buffer B=acetonitrile) to afford 26.5 mg (93%) of the title compound.

$^1$H NMR (DMSO-d$_6$): δ 11.53 (br s, 1H), 10.66 (s, 1H), 10.09 (s, 1H), 8.85 (br s, 1H), 8.45 (s, 1H), 8.42 (s, 1H) 6.24 (s, 1H), 5.34 (s, 1H), 5.29 (d, 1H, J=6.6 Hz), 4.91 (dd, 1H, J=5.4 Hz), 4.0-3.9 (m, 1H), 3.85-3.75 (m, 3H), 0.79 (s, 3H). MS (M+1): 376.1

Example 13

Preparation of 9-methoxyamino-2-(2'-methyl-β-D-ribofuranosyl)-2,6-dihydro-2,3,5,6-tetraaza-benzo[cd]azulen-7-one (Compound 313)

To a solution of the product from Example 35 (20 mg, 0.0575 mmol) in pyridine (3 mL) was added 60 mg of methoxylamine.HCl salt. The reaction was stirred at RT for overnight and checked by LC-MS. The reaction then was concentrated. The crude product was purified by HPLC to afford 12 mg of the title compound as a mixture of tautomers;

$^1$H NMR (DMSO-d$_6$, 300 MHz): δ 11.194 (s, 1H), 8.918 (s, 1H), 8.573 (s, 1H), 6.233 (s, 1H), 5.30-5.20 (m, 3H), 4.04-3.86(m, 4H), 3.91 (s, 1H), 2.50 (s, 2H), 0.689 (s, 3H); MS (M+1): 378.1.

Example 14

Preparation of 9-Amino-2-(2'-methyl-β-D-ribofuranosyl)-2,6-dihydro-2,3,5,6-tetraaza-benzo[cd]azulen-7-one (Compound 314)

To the product from Example 1, Step 5 (100 mg, 0.266 mmol) was added liquid ammonia (3 mL) which was sealed in an autoclave bomb and heated to 85° C. for 1 hour. The ammonia was allowed to evaporate and the residue was taken up in 0.5 M NaOEt (8.4 mL) and heated to 85° C. overnight. The reaction mixture was concentrated and purified on Phenomenex-C$^{18}$ reverse phase HPLC with a 0-35% B gradient over 30 min at 10 mL/min (Buffer A=H$_2$O, Buffer B=acetonitrile) to afford 22 mg of the title compound;

$^1$H NMR (DMSO-d$_6$): δ 0.756 (s, 3H), 3.74-3.9 (m, 4H), 4.88 (t, 1H), 5.04 (s,1H), 5.24 (s, 2H), 6.19 (s, 1H), 6.7 (s, 2H), 7.84 (s, 1H), 8.31 (s, 1H), 10.06 (s,1H); MS (M+1): 348.14.

Example 15

Preparation of 9-hydroxyamino-2-(2'-methyl-β-D-ribofuranosyl)-2,6-dihydro-2,3,5,6-tetraaza-benzo[cd]azulen-7-one (Compound 315)

To a solution of the product from Example 35 (20 mg, 0.0575 mmol) in pyridine (3 mL) was added 20 mg of hydroxylamine HCl salt. The reaction was stirred at RT for overnight and checked by LC-MS. The reaction then was concentrated. The crude product was purified by HPLC to afford 11 mg of the title compound as a mixture of tautomers; $^1$H NMR (DMSO-$d_6$, 300 MHz): δ 9.20 (s, 1H), 8.639 (s, 1H), 8.556 (s, 1H), 7.979 (s, 1H), 7.824 (s, 1H), 6.262 (s, 1H), 6.094 (s, 1H), 4.173 (s, 1H), 4.00-3.60(m, 4H), 2.528 (s, 2H), 0.695 (s, 3H), 0.673 (s, 3H); MS (M+1): 364.1.

Example 16

Preparation of 8-fluoro-2-(2'-methyl-β-D-ribofuranosyl)-2,6-dihydro-2,3,5,6-tetraaza-benzo[cd]azulen-7-one (Compound 316)

Step 1. 4-Amino-5-formyl-7-(2'-methyl-β-D-ribofuranosyl)-7H-pyrrolo[2,3-d]pyrimidine The title product from Example 1, Step 4 (150 mg, 0.37 mmol) was dissolved in dry DMF (10 mL). The solution was degassed with argon and bubbled with carbon monoxide gas at room temperature for 20 minutes. Pd(PPh$_3$)$_4$ (55 mg, 0.048 mmol) was added and the solution turned burgundy. The mixture was heated at 50° C. while more CO gas was bubbling through the reaction. In 20 minutes at 50° C., 0.1 mL of tributyltin hydride in 0.5 mL of THF was added and the reaction turned to yellow from burgundy. Addition of tributyltin hydride was repeated every 15 minutes for 4 times. Then the reaction was checked by HPLC until the starting material disappeared. The mixture was then filtrated and concentrated. The crude product was purified by column chromatography to afford 70 mg of the 7-formyl intermediate; $^1$H NMR (DMSO-$d_6$, 300 MHz): δ 11.182 (s, 1H), 8.333 (s, 1H), 7.799 (s, 1H), 7.207-7.147 (d, 1H, J=18 Hz), 6.072 (s, 1H), 5.239 (s, 2H), 5.126 (m, 1H), 3.870-3.668 (m, 4H), 0.728 (s, 3H); MS (M+1): 309.1.

Step 2. 8-Fluoro-2-(2'-methyl-β-D-ribofuranosyl)-2,6-dihydro-2,3,5,6-tetraaza-benzo[cd]azulen-7-one (Compound 316)

NaH (0.6 mg) was added to 10 mL of DMSO and the solution was stirred for 15 minutes at room temperature then at 75° C. for 40 minutes. This formed the methylsulfonyl carbanion stock solution. Let the solution cooled down to room temperature. This solution (0.43 mL) was added to triethyl 2-fluoro-2-phosphonoacetate (0.143 mL, 0.84 mmol) at 5° C. (ice-bath) and the solution was stirring at RT for an additional 15 minutes. The product from step 1 in 1 mL of DMSO was added to the solution dropwise at 5° C. and let it stir at RT for 1.5 hours. The reaction was quenched with 10 mL of mixed water and DCM (1:1) and the organic layer was extracted twice with water. The combined aqueous layer was concentrated and separated by HPLC to give 8 mg of pure product.
$^1$H NMR (DMSO-$d_6$, 300 MHz): δ 11.182 (s, 1H), 8.333 (s, 1H), 7.799 (s, 1H), 7.207-7.147 (d, 1H, J=18 Hz), 6.072 (s, 1H), 5.239 (s, 2H), 5.126 (m, 1H), 3.870-3.668 (m, 4H), 0.728 (s, 3H); $^{19}$F NMR (DMSO-$d_6$, 300 MHz): 6-119.337 (d, 1F, J=21 Hz); MS (M+1): 351.1.

Example 17

Preparation of 9-amino-2-(2'-methyl-β-D-ribofuranosyl)-2,6-dihydro-2,3,5,6,8-pentaaza-benzo[cd]azulen-7-one (Compound 317)

Step 1. 4-Amino-6-bromo-5-cyano-7-[2'-methyl-2',3',5'-tris-O-(4"-methylbenzoyl)-β-D-ribofuranosyl]-7H-pyrrolo[2,3-d]pyrimidine The target compound was synthesized as described in the literature procedure *Bioorganic and Medicinal Chemistry Letters*, 2005, 15, 725-727.

Step 2. 4-Amino-5-cyano-7-[2'-methyl-2',3',5'-tris-O-(4"-methylbenzoyl)-β-D-ribofuranosyl]-7H-pyrrolo[2,3-d]pyrimidine To the product from Step 1 (1.5 g, 2.03 mmol) in dioxane (200 mL) was added TEA (282 μl, 2.03 mmol) and Pd/C (150 mg, 10% on carbon) and the resulting solution was hydrogenated at 55 psi for 8 hours. The solution was then filtered and the filtrate was concentrated in vacuo and purified on Isco CombiFlash purification system with a 40 g silica gel column and 0.1-15% MeOH gradient in DCM over 30 minutes to afford 750 mg (56%) of the target compound.
MS (M+1): 660.2

Step 3. 4-Amino-7-(2'-methyl-β-D-ribofuranosyl)-7H-pyrrolo[2,3-d]pyrimidine-5-carboximidic acid methyl ester To the product from Step 2 (1.5 g, 2.28 mmol) was added a 0.5 Molar sodium methoxide solution (22.8 mL, 11.4 mmol) and stirred at ambient temperature for 4 hours. Silica gel was then added directly to reaction mixture and concentrated in vacuo. The product was purified on Isco CombiFlash purification system with a 80 g silica gel column and 0.1-40% MeOH gradient in DCM over 30 minutes to afford 450 mg (61%) of the target compound.
MS (M+1): 338.1

Step 4. 4-Amino-7-[2'-methyl-3',5'-O-(1",1",3",3"-tetraisopropyl-disiloxane-1",3"-diyl)-β-D-ribofuranosyl]-7H-pyrrolo[2,3-d]pyrimidine-5-carboximidic acid methyl ester To the product from Step 3 (468, 1.39 mmol) in anhydrous DMF was added imidazole (566 mg, 8.33 mmol) followed by the dropwise addition of 1,3-dichloro-1,1,3,3-tetraisopropyldisiloxane (572 μl, 1.77 mmol) under rapid stirring. The mixture was stirred under argon for 30 minutes then concentrated in vacuo. The crude product was taken up in DCM and silica gel added then re-concentrated. The product was purified on Isco CombiFlash purification system with a 40 g silica gel column and 0.1-5.0% MeOH gradient in DCM over 30 minutes to afford 570 mg (71%) of the target compound.
$^1$H NMR (DMSO-$d_6$): δ 10.0 (d, 1H, J=3.6 Hz), 8.17 (s, 1H), 8.06 (s, 1H), 7.63 (s,1H), 7.27 (d, 1H, J=3.9 Hz), 6.10 (s, 1H), 5.38 (s, 1H), 4.25-3.90 (m, 4H), 3.70 (s, 3H), 1.15-0.95 (m, 28H), 0.79 (s, 3H). MS (M+1): 580.3

Step 5. 9-Methoxy-2-[2'-methyl-3',5'-O-(1",1",3",3"-tetraisopropyldisiloxane-1",3"-diyl)-β-D-ribofuranosyl]-2,6-dihydro-2,3,5,6,8-pentaaza-benzo[cd]azulen-7-one To the product from Step 4 (200 mg, 0.345 mmol) in anhydrous toluene (175 mL) was added DMAP (210 mg, 1.72 mmol), TEA (1.20 ml, 8.63 mmol), 50 molecular sieves and the solution was cooled to 0° C. To this mixture was added a solution of triphosgene (154 mg, 0.518 mmol) in dry toluene (37 mL) dropwise under vigorous stirring. The mixture was allowed to stir an additional 5 minutes at 0° C. then quenched with methanol and concentrated in vacuo. The product was purified on Isco CombiFlash purification system with a 40 g silica gel column and 0.1-5.0% MeOH gradient in DCM over 30 minutes to afford 83 mg (40%) of the target compound.

$^1$H NMR (DMSO-d$_6$): δ 10.77 (s, 1H), 8.43 (s, 1H), 7.86 (s,1H), 6.10 (s, 1H), 5.62 (s, 1H), 4.26-3.96 (m, 4H), 3.87 (s, 3H), 1.15-0.95 (m, 28H), 0.84 (s, 3H). MS (M+1): 606.3

Step 6. 9-Methoxy-2-(2'-methyl-β-D-ribofuranosyl)-2,6-dihydro-2,3,5,6,8-pentaaza-benzo[cd]azulen-7-one The product from Step 5 (20 mg, 0.033 mmol) in THF (588 μL) was cooled to 0° C. and a 1 Molar solution of TBAF was added dropwise under vigorous stirring. The mixture was allowed to stir at 0° C. for 15 minutes then silica gel was added and the mixture was concentrated to dryness in vacuo. The product was purified on Isco CombiFlash purification system with a 4 g silica gel column and 0.1-30% MeOH gradient in DCM over 30 minutes to afford 7 mg (58%) of the target compound.

$^1$H NMR (DMSO-d$_6$): δ 10.71 (s, 1H), 8.41 (s, 2H), 6.13 (s, 1H), 5.33 (dd, 1H, =4.8 Hz), 5.29 (s, 1H), 5.18(d, 1H, J=6.3 Hz), 4.05-3.80 (m, 3H), 3.88 (s, 3H), 3.75-3.60 (m, 1H), 0.71 (s, 3H). MS (M+1): 364.1

Step 7. 9-Amino-2-(2'-methyl-β-D-ribofuranosyl)-2,6-dihydro-2,3,5,6,8-pentaaza-benzo[cd]azulen-7-one (Compound 317)

The product from Step 6 (20 mg, 0.0551 mmol) was dissolved in liquid ammonia (3 mL) at −78° C. then warmed to ambient temperature in a pressure vessel and stirred for 30 minutes. The reaction was then cooled to −78° C. and opened to allow the ammonia to evaporate. The residue was purified on Phenomenex-C$^{18}$ reverse phase HPLC with a 0-50% B gradient over 30 min at 10 mL/min (Buffer A=H$_2$O, Buffer B=acetonitrile) to afford 11 mg (57%) of the title compound.

$^1$H NMR (DMSO-d$_6$): δ 10.13 (s, 1H), 8.36 (s, 1H), 8.07 (s, 1H), 8.03 (br s, 2H), 6.18 (s, 1H) 5.3-5.2 (m, 2H), 4.89 (dd, 1H, J=5.7 Hz), 3.95-3.90 (m, 1H), 3.85-3.70 (m, 3H), 0.74 (s, 3H). MS (M+1): 349.1

Example 18

Preparation of 9-chloro-2-(2'-methyl-β-D-ribofuranosyl)-2,6-dihydro-2,3,5,6-tetraaza-benzo[cd]azulen-7-one (Compound 318)

To a solution of the product from Example 1, Step 5 (25 mg, 0.066 mmol) in acetic acid (3 mL) was added 70 mg LiCl. The reaction was heated at 80° C. for 8 hours and monitored by HPLC. The intermediate α,β-unsaturated chloro-ester was concentrated and the crude product was purified by HPLC. The ester was treated with 75 mg of tetrabutylammoniumdihydrogentrifluoride (50% solution in dichloroethane) and 16 mg of tetrabutylammoniumfluoride (TBAF) in the presence of 50 mg of LiCl at 105° C. for 12 hours. Additional TBAF (16 mg) was added 3 more times every 5 hours. The mixture was purified by HPLC to afford 5 mg of the title compound;

$^1$H NMR (DMSO-d$_6$, 300 MHz): δ 10.963 (s, 1H), 8.339 (s, 1H), 8.281 (s, 1H), 6.042 (s, 1H), 5.937 (s, 1H), 5.312-5.283 (t, 1H) 5.227 (s, 1H), 5.13 (d, 1H, J=6.6 Hz), 3.966-3.58 (m, 4H), 0.669 (s, 3H); MS (M+1): 367.0.

Example 19

Preparation of 9-iodo-2-(2'-methyl-β-D-ribofuranosyl)-2,6-dihydro-2,3,5,6-tetraaza-benzo[cd]azulen-7-one (Compound 319)

To a solution of the title product from Example 6, Step 5 (30 mg, 0.08 mmol) in acetic acid (3 mL) was added 100 mg of sodium iodide and 50 mg of zinc iodide. The reaction was heated at 95° C. for 48 hours and monitored by HPLC. The crude product was concentrated and purified by HPLC to afford 5 mg of the title compound;

$^1$H NMR (DMSO-d$_6$, 300 MHz): δ 10.958 (s, 1H), 8.372 (s, 1H), 8.097 (s, 1H), 6.490 (s, 1H), 6.102 (s, 1H), 4.0 (d, 1H, J=9 Hz), 3.903-3.837 (m, 2H), 3.65 (d, 1H, J=12.3 Hz), 0.709 (s, 3H); MS (M+1): 459.0.

Example 20

Preparation of 9-amino-2-(2-O-methyl-β-D-ribofuranosyl)-2,6-dihydro-7H-2,3,5,6-tetraazabenzo[cd]azulen-7-one (Compound 320)

Step 1. 4-Chloro-5-iodo-7-[3',5'-O-(1",1",3",3"-tetraisopropyl-disiloxane-1",3"-diyl)-β-D-ribofuranosyl]-7H-pyrrolo[2,3-d]pyrimidine To an ice-cold solution of the product from Example 6, Step 4 (0.90 g, 2.2 mmol) in pyridine (20 mL) was added TIPDSCl$_2$ (0.7 mL, 2.2. mmol) and the resulting mixture was stirred overnight at room temperature. The mixture was concentrated in vacuo. The residue was co-evaporated with toluene (2×10 mL) and partitioned between EtOAc (120 mL) and sat. aq. NaHCO$_3$ (20 mL). Organic layer was washed with water, sat. brine and dried (Na$_2$SO$_4$). The crude product was purified on a silica column with hexanes/EtOAc (9/1) as the eluent to yield the target compound (1.13 g, 79%) as off-white crisp foam.

$^1$H NMR (Acetone-d$_6$): δ 8.60 (s, 1H), 7.96 (s, 1H), 6.25 (d, 1H, J=1.2 Hz), 4.76-4.72 (m, 2H), 5.45 (m, 1H), 4.28-4.10 (m, 2H), 4.11 (m, 1H), 1.20-1.04 (m, 28H).

Step 2. 4-Chloro-5-iodo-7-[2'-O-methyl-3',5'-O-(1",1",3",3"-tetraisopropyl-disiloxane-1",3"-diyl)-β-D-ribofuranosyl]-7H-pyrrolo[2,3-d]pyrimidine To an ice-cold solution of the product from Step 1 (1.08 g, 1.64 mmol) in anhydrous DMF (20 mL) and MeI (308 μL, 4.94 mmol) was added NaH (80 mg, 2.0 mmol; 60% in mineral oil) under argon. Reaction mixture was stirred at 0° C. for 30 min and then the reaction quenched with 1N NH$_4$Cl (10 mL). The mixture was extracted with CH$_2$Cl$_2$ (100 mL) and organic layer washed with water, sat. brine and dried (Na$_2$SO$_4$). Purification on a silica gel column with hexanes/EtOAc (13/1) as the eluent yielded 0.76 g (70%) of the target compound.

¹H NMR (Acetone-d₆): δ 8.62 (s, 1H), 7.94 (s, 1H), 6.27 (s, 1H), 4.71 (m, 1H), 4.29-4.09 (m, 4H), 3.69 (s, 3H), 1.19-1.06 (m, 28H).

Step 3. 7-(2'-O-Methyl-β-D-ribofuranosyl)-4-chloro-5-iodo-7H-pyrrolo[2,3-d]pyrimidine Into an ice-cold solution of compound from Step 2 (0.64 g, 0.96 mmol) in THF (10 mL) was added TBAF (1.9 mL, 1.9 mmol; 1M in THF) and the resulting mixture stirred at 0° C. for 1 h. Mixture was diluted with MeOH (5 mL) and concentrated in vacuo. The evaporated residue was purified on a silica gel column with CH2Cl2/MeOH (50/1) as the eluent to yield 410 mg (100%) of the target compound.

¹H NMR (Acetone-d₆): δ 8.62 (s, 1H), 8.22 (s, 1H), 6.41 (d, 1H, J=5.6 Hz), 4.59-4.51 (m, 2H), 4.32 (m, 1H), 4.18 (d, 1H, J=5.3 Hz), 4.12 (m, 1H), 3.85 (m, 2H), 3.42 (s, 3H). MS: m/z=426.7 (M+1)

Step 4. 7-(2'-O-Methyl-β-D-ribofuranosyl)-4-amino-5-iodo-7H-pyrrolo[2,3-d]pyrimidine The nucleoside prepared as described above (410 mg, 0.96 mmol) and 1 mL of dioxane was treated with liquid ammonia at 100° C. for 22 h in the high pressure metal reactor. After evaporation of ammonia the residue was purified on silica gel with $CH_2Cl_2$/MeOH (30/1) as the eluents to yield the target compound as a white solid (310 mg, 80%).

¹H NMR (CD₃CN): δ 8.14 (s, 1H), 7.44 (s, 1H), 6.00 (br s, 2H), 5.94 (d, 1H, J=6.2 Hz), 5.00 (dd, 1H, J=9.1, 3.5 Hz), 4.41 (m, 1H), 4.09 (m, 1H), 3.78 (m, 1H), 3.67 (m, 1H), 3.33 (s, 3H).

Step 5. [7-(2'-O-Methyl-β-D-ribofuranosyl)-4-amino-7H-pyrrolo[2,3-d]pyrimidin-5-yl]-propynoic acid ethyl ester To a solution of the product from Step 4 (177 mg, 0.44 mmol) in DMF (5 mL) were added CuI (17 mg, 0.09 mmol) and TEA (121 μL, 0.88 mmol). The mixture was degassed with argon under sonication for 2-3 minutes. Pd(PPh₃)₄ (50 mg, 0.044 mmol) was added then and the reaction mixture was heated at 55° C. for 15 min. Ethyl propiolate (5×11 μL, 0.54 mmol) was added to the reaction mixture at 55° C. in 30 minutes intervals. After cooling down to room temperature the crude mixture was concentrated and purified on silica gel with $CH_2Cl_2$/MeOH (100/1, 75/1, 50/1) as the eluents to afford 88 mg (53%) of the target compound.

¹H NMR (DMSO-d₆): δ 8.24 (s, 1H), 8.18 (s, 1H), 6.75 (br, 2H), 6.15 (d, 1H, J=5.9 Hz), 5.25-5.21 (m, 2H), 4.27 (m, 1H,), 4.23 (q, 2H, J=7.0 Hz), 4.16 (m, 1H), 3.93 (m, 1H), 3.60 (m, 2H), 3.32 (s, 3H), 1.26 (t, 3H, J=7.0 Hz). MS: m/z=377.7 (M+1)

Step 6. [7-(2'-O-Methyl-β-D-ribofuranosyl)-4-amino-7H-pyrrolo[2,3-d]pyrimidin-5-yl]-acrylic acid ethyl ester The nucleoside, prepared as described above (88 mg, 0.23 mmol) was treated with liquid ammonia at 75° C. for 1.5 h in the high pressure metal reactor. After evaporation of ammonia the residue was purified on a silica gel column with $CH_2Cl_2$/MeOH (40/1, 30/1, 20/1) as the eluents to yield the target compound as off-white foam (68 mg, 74%).

¹H NMR (CD₃OD): δ 8.13 (s, 1H), 7.73 (s, 1H), 6.17 (d, 1H, J=5.9 Hz), 4.86 (s, 1H), 4.44 (dd, 1H, J=5.0, 3.2 Hz), 4.28 (m, 1H), 4.13 (q, 2H, J=7.1 Hz), 4.10 (m, 1H), 3.86 (dd, 1H, J=12.3, 2.6 Hz), 3.75 (dd, 1H, J=12.3, 2.9 Hz), 3.40 (s, 3H), 1.27 (t, 3H, J=7.2 Hz). MS: m/z=394.7 (M+1)

Step 7. 9-Amino-2-(2-O-methyl-β-D-ribofuranosyl)-2,6-dihydro-7H-2,3,5,6-tetraazabenzo[cd]azulen-7-one (Compound 320)

A solution of the product from Step 6 (67 mg, 0.17 mmol) in 0.1M NaOMe (17 mL) was heated at reflux temperature for 2 hour then concentrated in vacuo and purified on Phenomenex-C₁₈ reverse phase HPLC with a 0-40% B gradient over 30 min at 10 mL/min (Solvent A=H₂O, Solvent B=MeCN). The target compound was isolated as a white solid in 24 mg (41%) yield.

¹H NMR (DMSO-d₆): δ 10.07 (br s, 1H), 8.30 (s, 1H), 7.99 (s, 1H), 6.69 (br s, 1H), 6.17 (d, 1H, J=6.2 Hz), 5.31 (d, 1H, J=5.6 Hz), 5.05 (m, 2H), 4.27 (m, 1H), 4.08 (m, 1H), 3.94 (m, 1H), 3.59 (m, 2H), 3.30 (s, 3H). MS m/z=348.7 (M+1).

Example 22

Preparation of 2-(2'-methyl-β-D-ribofuranosyl)-2,6,7,9-tetrahydro-2,3,5,6,7,9-hexaaza-benzo[cd]azulen-8-one (Compound 322)

Step 1. 5-tert-Butoxycarbonylamino-4-chloro-7-(2'-methyl-2',3',5'-tris-O-acetyl-β-D-ribofuranosyl)-7H-pyrrolo[2,3-d]pyrimidine To 4-Chloro-7-(2'-methyl-2',3',5'-tris-O-acetyl-β-D-ribofuranosyl)-5-nitro-7H-pyrrolo[2,3-d]pyrimidine in DMF in a round bottom flask. 1.2 eq. of di-tert-butyl dicarbonate and 0.1 eq. Pd/C (10%) are added. Hydrogen in a balloon is attached to the flask and 1 is hydrogenated until TLC indicates completion of reaction. The reaction mixture is filtered to remove the catalyst and the filtrate is evaporated. Column chromatography of the crude product yields.

Step 2. 5-tert-Butoxycarbonylamino-4-hydrazino-7-(2'-methyl-2',3',5'-tris-O-acetyl-β-D-ribofuranosyl)-7H-pyrrolo[2,3-d]pyrimidine To the product from Step 2 in THF is added 5 eq. of hydrazine. The reaction is warmed 50° C. and stirred until TLC indicates completion of reaction. Evaporation of the reaction mixture followed by column chromatography purification yields a mixture of deactylated products. Reactylation of the hydroxyl groups with 10 eq. acetyl chloride in a 0.1M at room temperature followed by evaporation and column chromatography yields the target compound.

Step 3. 5-tert-Butoxycarbonyl-2-(2'-methyl-2',3',5'-tris-O-acetyl-β-D-ribofuranosyl)-2,6,7,9-tetrahydro-2,3,5,6,7,9-hexaaza-benzo[cd]azulen-8-one The product from Step 3 is stirred with 0.2 eq. of DMAP, 2 eq. of triethyl amine as a 0.1M solution in toluene. Triphosgene is added gradually until TLC or LC-MS indicates consumption of starting material. At this point the reaction mixture is separated between water and ethyl acetate, and the aqueous layer is extracted two more times with ethyl acetate. The organic fractions are combined washed with brine, dried over sodium sulfate and evaporated. Subsequent purification via column chromatography yields the target compound.

Step 4. 2-(2'-Methyl-β-D-ribofuranosyl)-2,6,7,9-tetrahydro-2,3,5,6,7,9-hexaaza-benzo[cd]azulen-8-one (Compound 322)

The product from Step 4 is dissolved in 50% TFA/methylene chloride containing 2% anisole giving a 0.1M solution. Evaporation of the reaction mixture followed by column chromatography yields the partially deprotected product that is subsequently subjected to a 1:1 mixture of methanol/concentrated aqueous ammonia and stirred until complete TLC indicates complete deacetylation. Evaporation of the reaction mixture and column chromatography yields the title compound.

Example 23

Preparation of 2-(2'-methyl-β-D-ribofuranosyl)-2,9-dihydro-6H-2,3,5,6,9-pentaaza-benzo[cd]azulene-7,8-dione (Compound 323)

Step 1. 4-Chloro-7-(2'-methyl-3',5'-bis-O-2,4-dichlorobenzyl-β-D-ribofuranosyl)-7H-pyrrolo[2,3-d]pyrimidine 4-Chloro-7H-pyrrolo[2,3-d]pyrimidine (10.0 g, 65.11 mmol) (Toronto Research) was suspended in 1.3 liters of dry acetonitrile and NaH (2.6 g, 65.11 mmol, 60% dispersion in oil) was added and the mixture was stirred for 4 hours at ambient temperature under argon. Meanwhile, 1-O-methyl-3,5-bis-O-(2,4-dichlorobenzyl)-2'-methyl-D-ribofuranoside (12.8 g, 25.79 mmol) was dissolved in 284 mL of dry dichloromethane, cooled down to 0° C. and HBr (28 mL, 30% w/w in AcOH) was added drop wise over 30 minutes. The reaction was kept for 1 hour at 0° C. and 3.0 hours more at ambient temperature then evaporated. The mixture was 3 times co-evaporated with dry toluene, dissolved in dry acetonitrile (200 mL) and added to the sodium salt of the base. The reaction mixture was kept at room temperature over night and evaporated to dryness. The residue was taken up in ethyl acetate (500 mL) and washed with water (3×100 mL). The organic fraction was dried over sodium sulfate, evaporated, and the crude material was purified by flash chromatography on silica gel (ethyl acetate/dichloromethane 5:100 v/v) to yield 10.0 g (63%) of protected nucleoside;

MS: 617.75 (M+1); $^1$H NMR (CDCl$_3$): δ 8.64 (s, 1H), 7.68 (d, 1H, J=3.6 Hz), 7.5-7.1 (m, 6H), 6.56 (d, 1H, 3.6 Hz), 6.4 (s, 1H), 4.8-4.5 (m, 4H), 4.3-3.65 (m, 4H), 0.93 (s, 3H).

Step 2. 4-Chloro-7-(2'-methyl-β-D-ribofuranosyl)-7H-pyrrolo[2,3-d]pyrimidine To the solution of the product from Step 1 (10.0 g, 16.19 mmol) in dichloromethane (440 mL) at −78° C. was added boron trichloride (1M in dichloromethane) (157 mL, 157.0 mmol) dropwise over 30 minutes. The mixture was stirred at −78° C. for 2 hours then at −20° C. overnight. The reaction was quenched with dichloromethane/methanol 1:1 (420 mL) and neutralized at 0° C. with aqueous ammonia. The solid was filtered, washed with dichloromethane/methanol 1:1 and the combined extracts evaporated in vacuo. The residue was purified on silica gel column with dichloromethane/methanol (10:1 v/v) as eluent. Fractions containing product were combined and concentrated to yield 4.1 g (84%) of the deprotected nucleoside;

MS: 300.08 (M+1); $^1$H NMR (D$_2$O): δ 8.32 (s, 1H), 7.57 (d, 1H, J=3.6 Hz), 6.56 (d, 1H, J=3.6 Hz), 6.17 (s, 1H), 4.0-3.5 (m, 4H), 6.65 (s, 3H).

Step 3. 4-Amino-7-(2'-methyl-β-D-ribofuranosyl)-7H-pyrrolo[2,3-d]pyrimidine

The product from Step 2 (1.1 g, 3.68 mmol) was placed in an autoclave pressure bomb and liquid ammonia was added (10 mL) at −78° C. The vessel was sealed and heated to 85° C. for 24 hours. The vessel was cooled back to −78° C., opened and the ammonia was allowed to evaporate. The residue was taken up in a small amount of methanol and plated onto a glass filter column containing a small pad of silica gel. The methanol was allowed to evaporate under vacuum and the product was eluded by ramping to 20% methanol in dichloromethane to give 1.0 g (97%) of a light yellow powder;

$^1$H NMR (CD$_3$OD): δ 8.06 (s, 1H), 7.48 (d, 1H, J=3.6 Hz), 6.60 (d, 1H, J=3.6 Hz), 6.21 (s, 1H), 4.13-3.85 (m, 4H), 0.81 (s, 3H); MS: 281.14 (M+1).

Step 4. 4-Amino-7-(2'-methyl-2',3',5'-tris-O-acetyl-β-D-ribofuranosyl)-7H-pyrrolo[2,3-d]pyrimidine To a solution of the product from Step 3 (1.10 g, 3.92 mmol) in glacial acetic acid (8 mL) was added acetyl chloride (3 mL) and the mixture stirred at room temp overnight. The reaction was concentrated in vacuo and the residue was plated onto silica gel column with dichloromethane and eluded by ramping to 5% methanol in dichloromethane to give 1.5 g (94%);

MS 407.18 (M+1).

Step 5. 4-Amino-7-(2'-methyl-2',3',5'-tris-O-acetyl-β-D-ribofuranosyl)-5-nitro-7H-pyrrolo[2,3-d]pyrimidine A solution of the product from Step 4 (1.5 g, 3.69 mmol) in dichloromethane (25 mL) was cooled to 0° C. and a 1:1 mixture of fuming nitric acid and sulfuric acid (4 mL) was added dropwise and the reaction was vigorously stirred at 0° C. for 20 min. The reaction was quenched with ice cold saturated sodium bicarbonate solution. The quenched reaction was diluted with water and extracted with dichloromethane. The organic layer was dried over sodium sulfate and concentrated in vacuo. The residue was purified by plating on silica gel with dichloromethane and eluded by ramping to 5% methanol in dichloromethane to give 600 mg (36%);

MS: 452.16 (M+1).

Step 6. 4-Amino-5-tert-butoxycarbonylamino-7-(2'-methyl-2',3',5'-tris-O-acetyl-β-D-ribofuranosyl)-7H-pyrrolo[2,3-d]pyrimidine To a solution of the compound from Step 5 (200 mg, 0.443 mmol) in DMF was added 10% Pd/C (100 mg) and di-tert-butyl dicarbonate (384 mg, 1.761 mmol). The solution was purged with H$_2$ gas for 5 minutes then heated to 85° C. for 4 hours under 1 atmosphere of H$_2$ via balloon. The catalyst was then filtered and the mixture concentrated in vacuo. The crude mixture was purified on Isco CombiFlash purification system with a 4 g silica gel column and 0.1-5.0% MeOH gradient in DCM over 30 minutes to afford 150 mg (65%).

Step 7. 9-tert-Butoxycarbonyl-2-(2'-methyl-2',3',5'-tris-O-acetyl-β-D-ribofuranosyl)-2,9-dihydro-6H-2,3,5,6,9-pentaaza-benzo[cd]azulene-7,8-dione To the product from Step 6 in anhydrous toluene (0.002M) is added DMAP (5 eq), TEA (20 eq), molecular sieves and the solution is cooled to 0° C. To this mixture is added a solution of oxalyl chloride (1.5 eq) in dry toluene (0.015M) dropwise under vigorous stirring. The mixture is allowed to stir until sufficiently complete as determined by TLC then the reaction is quenched with methanol and concentrated in vacuo. The product is purified on Isco CombiFlash purification system to afford the target compound.

Step 8. 2-(2'-Methyl-2',3',5'-tris-O-acetyl-β-D-ribofuranosyl)-2,9-dihydro-6H-2,3,5,6,9-pentaaza-benzo[cd]azulene-7,8-dione The product from Step 7 in DCM is cooled to 0° C., and TFA is added to the vigorously stirred mixture. The mixture is allowed to stir until product is sufficiently deboc'd as determined by TLC. The crude material is concentrated in vacuo and purified by flash chromatography to give the target compound.

Step 9. 2-(2'-Methyl-β-D-ribofuranosyl)-2,9-dihydro-6H-2,3,5,6,9-pentaaza-benzo[cd]azulene-7,8-dione (Compound 323)

To the product from Step 8 is added 7N $NH_3$ in MeOH and the mixture is stirred at ambient temperature until deacetylation is sufficiently complete as determined by TLC. The mixture is concentrated in vacuo and the crude material is taken up and purified by Phenomenex-$C^{18}$ reverse phase HPLC (Buffer A=$H_2O$, Buffer B=acetonitrile) to afford the title compound.

Example 24

Preparation of 9-cyano-2-(2'-methyl-β-D-ribofuranosyl)-2,6-dihydro-2,3,5,6-tetraaza-benzo[cd]azulen-7-one (Compound 324)

To a solution of the title product from Example 19 in DMF is added CuCN/$Bu_4$NCN and the mixture is stirred at 65° C. overnight to form the title compound.

Example 25

Preparation of 9-amino-8-fluoro-2-(2'-methyl-β-D-ribofuranosyl)-2,6-dihydro-2,3,5,6-tetraaza-benzo[cd]azulen-7-one (Compound 325)

The product from Example 34 is mixed with liquid ammonia at −78° C. in Parr Bomb. The sealed bomb is heated to 85° C. for overnight. The reaction is cooled and ammonia is evaporated. The crude product is purified by HPLC to yield the title compound.

Example 27

Preparation of 9-amino-2-(2'-methyl-β-D-ribofuranosyl)-2,6-dihydro-2,3,5,6-tetraaza-benzo[cd]azulene-7-thione (Compound 327)

Step 1. 9-Amino-2-(2'-methyl-2',3',5'-tris-O-acetyl-β-D-ribofuranosyl)-2,6-dihydro-2,3,5,6-tetraaza-benzo[cd]azulene-7-one To a mixture of the product from Example 14 (100 mg, 0.28 mmol) in acetyl chloride/glacial acetic acid (3 mL, 1:2, v/v) is stirred at room temperature until disappearance of the starting nucleoside, as judged by TLC. The mixture is evaporated in vacuo to dryness and purified on silica gel column.

Step 2. 9-Amino-2-(2'-methyl-2',3',5'-tris-O-acetyl-β-D-ribofuranosyl)-2,6-dihydro-2,3,5,6-tetraaza-benzo[cd]azulene-7-thione To a solution of the compound from Step 1 (75 mg, 0.16 mmol) in dioxane (2 mL) is added pyridine (2.5 mL) followed by phosphorus pentasulfide (2 equiv). The reaction mixture is heated at reflux for 24 h. The solvent is evaporated then and the residue washed with pyridine. The combined washings are evaporated and the residue is dissolved in $CHCl_3$ and washed with 10% aq. $NaHCO_3$ and water and dried ($Na_2SO_4$). The evaporated residue is used as such for the next step.

Step 3. 9-Amino-2-(2'-methyl-β-D-ribofuranosyl)-2,6-dihydro-2,3,5,6-tetraaza-benzo[cd]azulene-7-thione (Compound 327)

To a suspension of the compound from the Step 2 (50 mg, 0.1 mmol) in EtOH (2 mL) is added 1N aq. NaOH (0.1 mL). The reaction mixture is stirred at room temperature for 1 h. At this point the pH is brought to 7 with acetic acid and the solvent is evaporated in vacuo. The residue is purified by RP HPLC to yield the tile product.

Example 29

Preparation of 9-carbamoyl-2-(2'-methyl-β-D-ribofuranosyl)-2,6-dihydro-2,3,5,6-tetraaza-benzo[cd]azulen-7-one (Compound 329)

To the compound from Example 24 is added a $NH_4OH$ and $H_2O_2$ in alcoholic solution to yield the titled compound.

Example 32

Preparation of 2-(2'-methyl-β-D-ribofuranosyl)-6,7-Dihydro-2,3,5,6,7-pentaaza-benzo[cd]azulene (Compound 332)

Step 1. 4-Hydrazino-5-iodo-7-(2'-methyl-β-D-ribofuranosyl)-7H-pyrrolo[2,3-d]pyrimidine The compound of Example 1, Step 3 is dissolved in methanol to form a 0.1M solution. This solution is heated to 50° C. Hydrazine (5 eq.) is added. The reaction is monitored via TLC. Upon completion the reaction mixture is evaporated and separated via column chromatography to give the target compound.

Step 2. 5-Formyl-4-hydrazino-7-(2'-methyl-β-D-ribofuranosyl)-7H-pyrrolo[2,3-d]pyrimidine The compound from Step 1 is dissolved as a 0.1M solution in THF and 0.2 eq. of tetrakis(triphenylphosphine)palladium (0) are added. While bubbling carbon monoxide gas into the solution, 1 eq. of tributyltin hydride is added over the period of 6 hours. The reaction is then evaporated and subjected to silica gel chromatography, to give the target compound.

Step 3. 4-Hydrazino-5-methoxyvinyl-7-(2'-methyl-β-D-ribofuranosyl)-7H-pyrrolo[2,3-d]pyrimidine To a solution of THF at 0° C., diisopropyl ethyl amine (10 eq.), and n-butyl-lithium (10 eq.), is ($Ph_3P$)$ClCH_2OCH_3$ (10 eq.). After stirring this mixture at room temperature for 1.5 hours, one cools to −78° C. and adds the compound from Step 2. After stirring at –78 C overnight one warms to room temperature, separates the reaction mixture between water and chloroform, extracts the aqueous layer two more times with chloroform, and combines the organic layers. They are dried over sodium sulfate, evaporated and purified via column chromatography to give the target compound.

Step 4. [4-Hydrazino-7-(2'-methyl-β-D-ribofuranosyl)-7H-pyrrolo[2,3-d]pyrimidin-5-yl]-acetaldehyde The compound from Step 3 is stirred in an 80% TFA/methylene chloride solution until TLC indicates complete hydrolysis. Toluene is added and the solution is evaporated. Column chromatography yields the target compound.

Step 5. 2-(2'-Methyl-β-D-ribofuranosyl)-6,7-Dihydro-2,3,5,6,7-pentaaza-benzo[cd]azulene (Compound 332)

A round bottom flask equipped with a Dean-Stark trap and a reflux condenser is charged with the compound from Step 4 and toluene. A catalytic amount of toluene sulfonic acid is added. The mixture is then refluxed overnight. Upon cooling the reaction mixture is evaporated and then separated via column chromatography and heated until isomerization yields the title compound.

Example 33

Preparation of 2-(2'-methyl-β-D-ribofuranosyl)-6,7-Dihydro-2,3,5,6,7,9-hexaaza-benzo[cd]azulene (Compound 333)

Step 1. 5-tert-Butoxycarbonyl-2-(2'-methyl-2',3',5'-tris-O-acetyl-β-D-ribofuranosyl)-6,7-Dihydro-2,3,5,6,7,9-hexaaza-benzo[cd]azulene To the product from Example 22, Step 3 is added 0.2 eq. of DMAP, 2 eq. of triethyl amine as a 0.1M solution in toluene. Trimethylorthoformate is added gradually until TLC or LC-MS indicates consumption of starting material. At this point the reaction mixture is separated between water and ethyl acetate, and the aqueous layer is extracted two more times with ethyl acetate. The organic fractions are combined washed with brine, dried over sodium sulfate and evaporated. Subsequent purification via column chromatography yields the target compound.

Step 2. 2-(2'-Methyl-β-D-ribofuranosyl)-6,7-Dihydro-2,3,5,6,7,9-hexaaza-benzo[cd]azulene (Compound 333)

To a solution of Step 1 is dissolved in 50% TFA/methylene chloride containing 2% anisole giving a 0.1M solution. Evaporation of the reaction mixture followed by column chromatography yields the partially deprotected product that is subsequently subjected to a 1:1 mixture of methanol/concentrated aqueous ammonia and stirred until complete TLC indicates complete deacetylation. Evaporation of the reaction mixture and column chromatography yields the title compound.

Example 34

Preparation of 8-fluoro-2-(2'-methyl-β-D-ribofuranosyl)-2,6-dihydro-2,3,5,6,-trtraaza-benzo[cd]azulene-7,9-dione (Compound 334)

To the title compound of Example 35 in acetonitrile (3 mL) is added 1.5 equivalence of Selectfluor (1-chloromethyl-4-fluoro-1,4-diazoniabicyclo[2.2.2]octane bis-tetrafluoroborate). The reaction is stirred at RT for overnight and monitored by LC-MS until sufficiently complete. The reaction then is then concentrated and the crude product is purified by HPLC to give the title compound.

Example 35

Preparation of 2-(2'-methyl-β-D-ribofuranosyl)-2,6-dihydro-2,3,5,6,-trtraaza-benzo[cd]azulen-7,9-dione (Compound 335)

Step 1. 3-[4-Amino-7-(2'-methyl-β-D-ribofuranosyl)-7H-pyrrolo[2,3-d]pyrimidin-5-yl]-3-oxo-propionic acid ethyl ester To the product from Example 1, Step 5 (150 mg, 0.399 mmol) in 70% aqueous MeOH (15 mL) was added $H_2SO_4$ (51.9 μl) and $HgSO_4$ (29.5 mg, 0.100 mmol) and the mixture was heated to 55° C. for 4 hours. The mixture was then concentrated and purified on Phenomenex-$C^{18}$ reverse phase HPLC with a 0-60% B gradient over 20 min at 10 mL/min (Buffer A=$H_2O$, Buffer B=acetonitrile) to afford 50 mg (32%) of the title compound.

$^1$H NMR (DMSO-$d_6$): δ 8.75 (s, 1H), 8.16 (s, 1H), 7.94 (br s, 1H), 7.53 (br s, 1H), 6.13 (s, 1H), 5.36 (dd, 1H, J=5.1 Hz), 5.30 (s, 1H), 5.16 (d, 1H, 6.6 Hz), 4.11 (q, 2H, J=7.2 Hz), 4.05-3.85 (m, 3H), 3.75-3.65 (m, 1H), 1.20 (t, 3H, J=6.9 Hz), 0.751 (s,3H). MS (M+1): 395.1

Step 2. 2-(2'-methyl-β-D-ribofuranosyl)-2,6-dihydro-2,3,5,6,-trtraaza-benzo[cd]azulen-7,9-dione (Compound 335)

To the product from Step 1 (25 mg, 0.0635 mmol) in EtOH (12.5 mL) was added NaOEt (21 wt. %) solution in ethanol (440 μl, 1.18 mmol) and the mixture was heated to 85° C. for 4 hours. The mixture was neutralized with glacial acetic acid, concentrated in vacuo and purified on Phenomenex-$C^{18}$ reverse phase HPLC with a 0-40% B gradient over 30 min at 10 mL/min (Buffer A=$H_2O$, Buffer B=acetonitrile) to afford 10 mg (45%) of the title compound.

$^1$H NMR (DMSO-$d_6$): [mixture of keto-enol tautomers] Enol-δ 11.38 (s, 1H), 10.45 (s, 1H), 8.72 (s, 1H), 8.64 (s, 1H), 6.23 (s, 1H), 5.45-5.15 (m, 3H), 5.29 (s, 1H), 4.02-3.60 (m, 4H), 0.74 (s, 3H); Keto-δ 11.08 (s, 1H), 8.34 (s, 1H), 8.06 (s, 1H), 6.13 (s, 1H), 5.45-5.15 (m, 3H), 4.09 (s, 2H), 4.02-3.60 (m, 4H), 0.71 (s, 3H). MS (M+1): 349.0

Example 40

General Procedure for Preparing Triphosphates

To a solution of nucleoside (0.05 mmol) in trimethyl phosphate (0.5 mL) under argon was added 4 Angstrom molecular sieves. The mixture was stirred overnight at room temperature and then cooled to 0° C. Phosphorus oxychloride (0.1 mmol) was added and the resulting mixture was stirred at 0° C. for 1 h. Then tributylamine (0.15 mmol), acetonitrile (0.1 mL), and tributylammonium pyrophosphate (0.2 mmol) were added and the mixture was stirred for an additional 30 min at 0° C. The reaction was quenched by addition of TEAB (tetraethylammonium bicarbonate) buffer (1M, 1 mL) and diluted with water (4 mL). The mixture was purified by ion exchange HPLC and desalted by RP-HPLC. Mass and purity was confirmed by MS and $^1$H- and $_{31}$P-NMR.

BIOLOGICAL EXAMPLES

Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture was disclosed in U.S. Pat. No. 5,738,985 to Miles et al. In vitro assays have been reported in Ferrari et al. *J. of Vir.*, 73:1649-1654, 1999; Ishii et al., *Hepatology*, 29:1227-1235, 1999; Lohmann et al., *J. Bio. Chem.*, 274:10807-10815, 1999; and Yamashita et al., *J. of Bio. Chem.*, 273:15479-15486, 1998.

WO 97/12033, filed on Sep. 27, 1996, by Emory University, listing C. Hagedorn and A. Reinoldus as inventors, which claims priority to U.S. Provisional Patent Application Ser. No. 60/004,383, filed on September 1995, described an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996:1 (Supp 4) 18-24.

Screens that measure reductions in kinase activity from HCV drugs were disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs were disclosed in U.S. Pat. No. 5,861,267 to Su et al., U.S. Pat. No. 5,739,002 to De Francesco et al., and U.S. Pat. No. 5,597,691 to Houghton et al.

Example 2

Replicon Assay

A cell line, ET (Huh-lucubineo-ET) was used for screening of compounds for inhibiting HCV RNA dependent RNA polymerase. The ET cell line was stably transfected with RNA transcripts harboring a $I_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells were grown in DMEM, supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). They were all available through Life Technologies (Bethesda, Md.). The cells were plated at $0.5\text{-}1.0\times10_4$ cells/well in the 96 well plates and incubated for 24 hrs before adding test compound. The compounds were added to the cells to achieve a final concentration of 0.1 nM to 50 µm and a final DMSO concentration of 0.5%. Luciferase activity was measured 48-72 hours later by adding a lysis buffer and the substrate (Catalog number Glo-lysis buffer E2661 and Bright-Glo luciferase system E2620 Promega, Madison, Wis.). Cells should not be too confluent during the assay. Percent inhibition of replication data was plotted relative to no compound control. Under the same condition, cytotoxicity of the compounds was determined using cell proliferation reagent, WST-1 (Roche, Germany). The compounds showing antiviral activities, but no significant cytotoxicities were chosen to determine $IC_{50}$ and $TC_{50}$. For these determinations, a 10 point, 2-fold serial dilution for each compound was used, which spans a concentration range of 1000 fold. $IC_{50}$ and $TC_{50}$ values were calculated by fitting % inhibition at each concentration to the following equation:

% inhibition=$100\%/[(IC50/[I])_b+1]$ where b is Hill's coefficient.

The % inhibition at a particular concentration was determined using the following equation:

% Inhibition=$100-[100*(Lum$ with inhibitor$-bg)/$ $(Lum$ with no inhibitor$-bg)]$ where bg was the background with no replicon cell, and Lum was the luminescence intensity of the reporter luciferase gene. In this assay, when tested at different concentrations in the range of 0.1-50 µM, compounds 306, 307, 308, 310, 311, 313, 314, 316, 317, 318, and 320 exhibited percent inhibitions that ranged from 8% to 97%.

Example 3

Cloning and Expression of Recombinant HCV-NS5b

The coding sequence of NS5b protein was cloned by PCR from pFKI$_{389}$luc/NS3-3'/ET as described by Lohmann, V., et al. (1999) *Science* 285, 110-113 using the primers shown on page 266 of WO 2005/012288.

The cloned fragment was missing the C terminus 21 amino acid residues. The cloned fragment was inserted into an IPTG-inducible expression plasmid that provides an epitope tag (His)$_6$ at the carboxy terminus of the protein.

The recombinant enzyme was expressed in XL-1 cells and after induction of expression, the protein was purified using affinity chromatography on a nickel-NTA column. Storage condition was 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity was assayed by measuring incorporation of radiolabeled UTP into a RNA product using a biotinylated, heteropolymeric template, which includes a portion of the HCV genome. Typically, the assay mixture (34 µL) contains 10 mM Tris-HCl (pH 7.5), 5 mM MgCl$_2$, 0.2 mM EDTA, 10 mM KCl, 1 unit/µL RNAsin, 1 mM DTT, 10 µM each of NTP, including [$_3$H]-UTP, and 10 ng/µL biotinylated heteropolymeric template. 20× test compound in 2 µl's was then added as a 100% DMSO solution to achieve a final DMSO concentration of 5%. For IC50 determination a 10-point dose response was used. The compounds were serial diluted 2-fold thus covering a range of 1000 fold. Typically for IC50's, compounds were tested starting at 50 uM or 2 µM depending on the potency. Reactions were started with addition of 10×NS5B in 4 µl's and allowed to incubate at 37° C. for 2 hours. Reactions were quenched with 8 µL of 100 mM EDTA and reaction mixtures (30 μL) were transferred to streptavidin-coated scintillation proximity microtiter plates (FlashPlates) and incubated at 4° C. overnight. Incorporation of radioactivity was determined by scintillation counting (cpm). The % Inhibition at a particular concentration was determined using the following equation, % Inhibition=100−[100*(cpm with inhibitor−$bg$)/(cpm with no inhibitor−$bg$)]

where bg was the background with no enzyme.

FORMULATION EXAMPLES

The following are representative pharmaceutical formulations containing a compound of the present invention.

Example 1

Tablet Formulation

The following ingredients are mixed intimately and pressed into single scored tablets.

| Ingredient | Quantity per tablet, mg |
|---|---|
| Compound of the invention | 400 |
| Cornstarch | 50 |
| Croscarmellose sodium | 25 |
| Lactose | 120 |
| Magnesium stearate | 5 |

Example 2

Capsule Formulation

The following ingredients are mixed intimately and loaded into a hard-shell gelatin capsule.

| Ingredient | Quantity per tablet, mg |
|---|---|
| Compound of the invention | 200 |
| Lactose, spray-dried | 148 |
| Magnesium stearate | 2 |

Example 3

Suspension Formulation

The following ingredients are mixed to form a suspension for oral administration (q.s.=sufficient amount).

| Ingredient | Amount |
|---|---|
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co.) | 1.0 g |
| flavoring | 0.035 mL |

| Ingredient | Amount |
|---|---|
| colorings | 0.5 mg |
| distilled water | q.s. to 100 mL |

Example 4

Injectable Formulation

The following ingredients are mixed to form an injectable formulation.

| Ingredient | Quantity per tablet, mg |
|---|---|
| Compound of the invention | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
|---|---|
| Compound of the invention | 500 mg |
| Witepsol ® H-15 | balance |

What is claimed is:

1. A compound that is 9-amino-2-(2'-methyl-β-D-ribofuranosyl)-2,6-dihydro-2,3,5,6-tetraaza-benzo[cd]azulen-7-one or a pharmaceutically acceptable salt thereof:

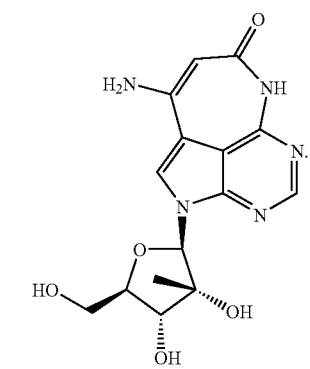

2. A pharmaceutical composition comprising a pharmaceutically acceptable carrier and a therapeutically effective amount of 9-amino-2-(2'-methyl-β-D-ribofuranosyl)-2,6-dihydro-2,3,5,6-tetraaza-benzo[cd]azulen-7-one or a pharmaceutically acceptable salt thereof.

3. A method for treating a viral infection in a mammal mediated at least in part by a virus in the Flaviviridae family of viruses, comprising administering to said mammal 9-amino-2-(2'-methyl-β-D-ribofuranosyl)-2,6-dihydro-2,3,5,6-tetraaza-benzo[cd]azulen-7-one or a pharmaceutically acceptable salt thereof.

4. The method of claim 3, wherein the viral infection is a hepatitis C mediated viral infection.

5. The method of claim 4 in combination with a therapeutically effective amount of one or more agents active against hepatitis C virus.

6. The method of claim 5 wherein said agent active against hepatitis C virus is an inhibitor of one or more of HCV proteases, HCV polymerase, HCV helicase, HCV NS4B protein, HCV entry, HCV assembly, HCV egress, HCV NS5A protein, or inosine 5'-monophosphate dehydrogenase.

7. The method of claim 6 wherein said active agent against HCV is Ribavirin, levovirin, viramidine, thymosin alpha-1, an inhibitor of NS3 serine protease, an inhibitor of inosine monophosphate dehydrogenase, interferon-alpha, or pegylated interferon-alpha.

8. The method of claim 3 wherein said mammal is a human.

\* \* \* \* \*